United States Patent
Pettersson et al.

(10) Patent No.: US 8,697,673 B2
(45) Date of Patent: Apr. 15, 2014

(54) BICYCLIC PYRIDINONES

(75) Inventors: Martin Youngjin Pettersson, Waterford, CT (US); Douglas Scott Johnson, Mystic, CT (US); Chakrapani Subramanyam, South Glastonbury, CT (US); Christopher John O'Donnell, Mystic, CT (US); Christopher William am Ende, Mystic, CT (US); Benjamin Adam Fish, Groton, CT (US); Michael Eric Green, Mystic, CT (US); Patrick Bradley Mullins, East Lyme, CT (US); Cory Michael Stiff, Salem, CT (US); Tuan Phong Tran, Ledyard, CT (US); Thayalan Navaratnam, Ledyard, CT (US)

(73) Assignee: Pfizer Inc., New York, NY (US)

(*) Notice: Subject to any disclaimer, the term of this patent is extended or adjusted under 35 U.S.C. 154(b) by 59 days.

(21) Appl. No.: 13/433,452

(22) Filed: Mar. 29, 2012

(65) Prior Publication Data

US 2012/0252758 A1     Oct. 4, 2012

Related U.S. Application Data

(60) Provisional application No. 61/599,022, filed on Feb. 15, 2012, provisional application No. 61/470,076, filed on Mar. 31, 2011.

(51) Int. Cl.
| | |
|---|---|
| *A61K 31/551* | (2006.01) |
| *A61K 31/695* | (2006.01) |
| *A61K 31/4985* | (2006.01) |
| *A61P 25/00* | (2006.01) |
| *A61P 25/18* | (2006.01) |
| *A61P 25/28* | (2006.01) |
| *C07D 401/04* | (2006.01) |
| *C07D 471/04* | (2006.01) |
| *C07F 7/10* | (2006.01) |

(52) U.S. Cl.
USPC ............. 514/63; 514/249; 514/221; 544/229; 544/349; 540/567; 546/274.1

(58) Field of Classification Search
USPC .................... 514/63, 249, 221; 544/229, 349; 540/567; 546/274.1
See application file for complete search history.

(56) References Cited

U.S. PATENT DOCUMENTS

| | | | |
|---|---|---|---|
| 5,700,810 A | 12/1997 | Natsugari et al. | 514/307 |
| 6,489,315 B1 | 12/2002 | Natsugari et al. | 514/185 |
| 7,253,180 B2 | 8/2007 | Chen et al. | 514/292 |
| 7,517,532 B2 | 4/2009 | Wai et al. | 424/208.1 |
| 7,638,629 B2 | 12/2009 | Hannam et al. | 546/124 |
| 7,741,315 B2 | 6/2010 | Vacca et al. | 514/183 |
| 7,812,040 B2 | 10/2010 | Wager | 514/364 |
| 7,897,632 B2 | 3/2011 | Kimura et al. | 514/397 |
| 7,902,195 B2 | 3/2011 | Hughes et al. | 514/249 |
| 7,923,450 B2 | 4/2011 | Baumann et al. | 514/264.11 |
| 8,097,621 B2 | 1/2012 | Bell et al. | 514/234.2 |
| 2002/0132817 A1 | 9/2002 | Natsugari et al. | 514/259.41 |
| 2003/0195205 A1 | 10/2003 | DeNinno et al. | 514/228.5 |
| 2004/0220186 A1 | 11/2004 | Bell et al. | 514/242 |
| 2006/0106035 A1 | 5/2006 | Hendrix et al. | 514/262.1 |
| 2006/0111372 A1 | 5/2006 | Hendrix et al. | 514/262.1 |
| 2007/0031416 A1 | 2/2007 | Shoji et al. | 424/146.1 |
| 2007/0117798 A1 | 5/2007 | Kimura et al. | 514/230.5 |
| 2007/0117839 A1 | 5/2007 | Kimura et al. | 514/306 |
| 2007/0155731 A1 | 7/2007 | Butora et al. | 514/222.8 |
| 2007/0197581 A1 | 8/2007 | Asberom et al. | 514/291 |
| 2008/0009490 A1 | 1/2008 | Williams et al. | 514/233.2 |
| 2008/0076738 A1 | 3/2008 | Cai et al. | 514/80 |
| 2008/0194591 A1 | 8/2008 | Entwistle et al. | 514/262.1 |
| 2008/0207900 A1 | 8/2008 | Kimura et al. | 544/74 |
| 2008/0280948 A1 | 11/2008 | Baumann et al. | 514/301 |
| 2009/0062529 A1 | 3/2009 | Kimura et al. | 540/568 |
| 2009/0163482 A1 | 6/2009 | McHardy et al. | 514/227.8 |
| 2009/0215759 A1 | 8/2009 | Baumann et al. | 514/227.8 |
| 2009/0306054 A1 | 12/2009 | Cai et al. | 514/218 |
| 2010/0016373 A1 | 1/2010 | Khilevich et al. | 514/341 |
| 2010/0041680 A1 | 2/2010 | Rivkin | 514/264.11 |
| 2010/0093731 A1 | 4/2010 | Goetschi et al. | 514/236.2 |

(Continued)

FOREIGN PATENT DOCUMENTS

| | | | |
|---|---|---|---|
| GB | 1419789 | 12/1975 | ........ C07D 215/22 |
| WO | WO 9944955 | 10/1999 | |

(Continued)

OTHER PUBLICATIONS

International application No. PCT/IB2012/051348, filed Mar. 21, 2012, Search Report mailed May 11, 2012, 4 pages.

(Continued)

*Primary Examiner* — San-Ming Hui
*Assistant Examiner* — Kathrien Cruz
(74) *Attorney, Agent, or Firm* — J. Michael Dixon

(57) ABSTRACT

Compounds and pharmaceutically acceptable salts of the compounds are disclosed, wherein the compounds have the structure of Formula I

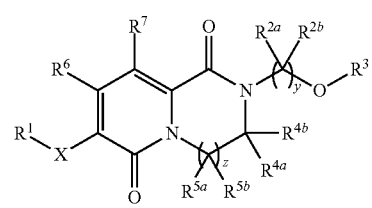

as defined herein. Corresponding pharmaceutical compositions, methods of treatment, methods of synthesis, and intermediates are also disclosed.

12 Claims, No Drawings

(56) References Cited

U.S. PATENT DOCUMENTS

| | | | |
|---|---|---|---|
| 2010/0105904 A1 | 4/2010 | Kimura et al. | 544/316 |
| 2010/0120874 A1 | 5/2010 | Baumann et al. | 514/364 |
| 2010/0130495 A1 | 5/2010 | Forsblom et al. | 514/235.5 |
| 2010/0137320 A1 | 6/2010 | Huang et al. | 514/248 |
| 2010/0204230 A1 | 8/2010 | Blurton et al. | 514/235.8 |
| 2010/0222320 A1 | 9/2010 | Fischer et al. | 514/210.18 |
| 2010/0247514 A1 | 9/2010 | Zhu et al. | 424/130.1 |
| 2010/0255005 A1 | 10/2010 | Zhu et al. | 424/172.1 |
| 2010/0256128 A1 | 10/2010 | Zhu et al. | 514/229.2 |
| 2010/0297128 A1 | 11/2010 | Huang et al. | 424/137.1 |
| 2010/0298359 A1 | 11/2010 | Huang et al. | 514/266.23 |
| 2010/0298372 A1 | 11/2010 | Huang et al. | 514/306 |
| 2010/0298381 A1 | 11/2010 | Zhu et al. | 514/326 |
| 2011/0009392 A1 | 1/2011 | Zhu et al. | 514/221 |
| 2011/0009619 A1 | 1/2011 | Kimura et al. | 540/568 |
| 2011/0015175 A1 | 1/2011 | Marcin et al. | 514/210.21 |
| 2011/0027264 A1 | 2/2011 | Huang et al. | 424/130.1 |
| 2011/0053918 A1 | 3/2011 | Zhu et al. | 514/222.2 |
| 2011/0070297 A1 | 3/2011 | Cao et al. | 424/450 |
| 2011/0082153 A1 | 4/2011 | Aslanian et al. | 514/252.05 |
| 2011/0118234 A1 | 5/2011 | Biswas et al. | 514/212.07 |
| 2011/0166132 A1 | 7/2011 | Hitchcock et al. | 514/230.5 |
| 2011/0172427 A1 | 7/2011 | Nakamura et al. | 546/119 |
| 2011/0207733 A1 | 8/2011 | Rivkin et al. | 514/235.8 |
| 2011/0237580 A1 | 9/2011 | Gijsen et al. | 514/232.5 |
| 2011/0251172 A1 | 10/2011 | Rivkin et al. | 514/210.18 |
| 2011/0257156 A1 | 10/2011 | Zhu et al. | 514/210.21 |
| 2011/0263529 A1 | 10/2011 | Xu et al. | 514/63 |
| 2011/0275822 A1 | 11/2011 | Minamisono et al. | 546/119 |
| 2011/0281881 A1 | 11/2011 | Gijsen et al. | 514/249 |
| 2011/0294784 A1 | 12/2011 | Asberom et al. | 514/211.09 |
| 2011/0313001 A1 | 12/2011 | Fischer et al. | 514/338 |
| 2012/0022044 A1 | 1/2012 | Fischer et al. | 514/212.07 |
| 2012/0022090 A1 | 1/2012 | Gijsen et al. | 514/275 |
| 2012/0053165 A1 | 3/2012 | Allen et al. | 514/210.18 |

FOREIGN PATENT DOCUMENTS

| | | | | |
|---|---|---|---|---|
| WO | WO 0032192 | 6/2000 | | A61K 31/4375 |
| WO | WO 2004024078 | 3/2004 | | |
| WO | WO 2006126081 | 11/2006 | | C07D 471/04 |
| WO | WO 2006126082 | 11/2006 | | C07D 471/04 |
| WO | WO 2006126083 | 11/2006 | | C07D 471/04 |
| WO | WO 2007063385 | 6/2007 | | |
| WO | WO 2007088450 | 8/2007 | | C07D 311/04 |
| WO | WO 2007088462 | 8/2007 | | C07D 491/10 |
| WO | WO 2007099423 | 9/2007 | | C07D 295/08 |
| WO | WO 2007138431 | 12/2007 | | |
| WO | WO 2008137102 | 11/2008 | | C07D 403/02 |
| WO | WO 2009050227 | 4/2009 | | C07D 403/10 |
| WO | WO 2009061699 | 5/2009 | | C07D 487/10 |
| WO | WO 2010075204 | 7/2010 | | C07D 513/14 |
| WO | WO 2010098332 | 9/2010 | | C07D 471/04 |
| WO | WO 2010098488 | 9/2010 | | C07D 401/14 |
| WO | WO 2010098495 | 9/2010 | | C07D 471/04 |
| WO | WO 2010098496 | 9/2010 | | C07D 401/04 |

OTHER PUBLICATIONS

International application No. PCT/IB2012/051348, filed Mar. 21, 2012, Written Opinion of International Searching Authority, mailed May 11, 2912, 7 pages.

Caldwell, J.P., et al., "Iminoheterocycles as γ-secretase modulators", Bioorganic & Medicinal Chemistry Letters, Sep. 15, 2010, pp. 5380-5384, 20(18).

Eiden, F., et al., "1-Pyrono-und 1-Pyridono-[3,4-b]chinoxaline. 33. Mitt. über Untersuchungen an 4-Pyronen", Archiv der Pharmazie, 1972, pp. 2-9, 305(1).

Eiden, F., et al., Pyrono-Chinoxaline AUS 3-Hydroxy-4-Pyronen[1]), Tetrahedron Letters, 1968, pp. 2903-2904, 9(24).

Garbaccio, R.M., et al., "Discovery of Oxazolobenzimidazoles as Positive Allosteric Modulators for the mGluR2 Receptors", ACS Medicinal Chemistry Letters, 2010, pp. 406-410, 1(8).

Gillman, K., et al., "Discovery and Evaluation of BMS-708163, a Potent Selective and Orally Bioavailable γ-Secretase Inhibitor", ACS Medicinal Chemistry Letters, Mar. 22, 2010, pp. 120-124; 1(3).

Goel, A., et al., "Amberlyst 15-Catalyzed Efficient synthesis of 5-Acetyl-4-hydroxy-coumarone and 5-Acetyl-6-hydroxy-coumarone: Crucial Precursors for Several Naturally Occurring Furanoflavones[1]", Synlett, 2004, pp. 1990-1994, vol. 11.

Grunewald, G.L., et al., "Binding Requirements of Phenolic Phenylethanolamines in the Benzonorbornene skeleton at the Active site of Phenylethanolamine N-Methyltransferase[1a,b]", Journal Medical Chemistry, Sep. 1986, pp. 1972-1982, 29(10).

Haleblian, et al., "Characterization of Habits and Crystalline Modification of Solids and Their Pharmaceutical Applications", Journal of Pharmaceutical Science, Aug. 1975, pp. 1269-1288, 64(8).

Hashimoto, T., et al., "A Novel Gamma-secretase Modulator-Pharmacology Part", Journal of Alzheimer's & Dementia, Jul. 2010, Supplemental, pp. S242 (PI-236), 6(4).

Huang, X, et al., "The Discovery of Pyridone and Pyridazone Heterocycles as γ-Secretase Modulators", ACS Medicinal Chemistry Letters, 2010, pp. 184-187, 1(4).

Hughes, J.D., et al., "Physiochemical drug properties associated with in vivo toxicological outcomes", Bioorganic & Medicinal Chemistry Letters, Sep. 1, 2008, pp. 4872-4875, 18(17).

Inamoto, K., et al., "Palladium-Catalyzed Synthesis of 2-Substituted Benzothiazoles via a C—H Functionalization/Intramolecular C—S Bond Formation Process", Organic Letters, 2008, pp. 5147-5150, 10(22).

Kato, D., et al.,"Microbial Deracemization of α-Substituted Carboxylic Acids: Substrate Specificity and Mechanistic Investigation", Journal Organic Chemistry, Sep. 19, 2003, pp. 7234-7242, 68(19).

Kawahara, N., et al., "A simple synthesis of dimethyl 2-pyridone-4,5-dicarboxylate derivatives", Journal of Heterocyclic Chemistry, 1989, pp. 847-852, 26(3).

Kawahara, N., et al., "Synthesis and Thermal Cyclization Reactions of Methyl Isocrotonate Derivatives", Chemical & Pharmaceutical Bulletin, Feb. 1987, pp. 457-467, 35(2).

Kounnas, Maria Z., et al., "Modulation of γ-Secretase Reduces β-Amyloid Deposition in a Transgenic Mouse Model of Alzheimer's Disease", Neuron, Sep. 9, 2010, pp. 769-780, 67(5).

Lee, J.C., et al., "Facile Synthesis of Oxazoles Starting from Ketones", Synthetic Communications 2003, pp. 1611-1614, 33(9).

Lin, Y., et al., "New Synthesis of Isoxazoles and Isothiazoles. A Convenient Synthesis of Thioenaminones from Enaminones", Journal of Organic Chemistry, Nov. 1980, pp. 4857-4860, 45(24).

Liu, J., et al., "Synthesis and Photophysical Properties of New Fluorinated Benzo[c]xanthene Dyes as Intracellular pH Indicators", Bioorganic & Medicinal Chemistry Letters, 2001, pp. 2903-2905, 11(22).

Liu, W., et al., "Total synthesis of Isoprekinamycin: Structural Evidence for Enhanced Diazonium Ion Character and Growth Inhibitory Activity toward Cancer Cells", Organic Letters, 2007, pp. 2915-2918, 9(15).

Morphy, Richard, "The Influence of Target Family and Functional Activity on the Physicochemical Properties of Pre-Clinical Compounds", Journal of Medicinal Chemistry, 2006, pp. 2969-2978, 49(10).

Narender, N., et al., "Highly Efficient, Para-selective Oxychlorination of Aromatic Compound Using Potassium Chloride and Oxone", Synthetic Communication 2002, pp. 279-286, 32(2).

Oliveira, M.M., et al., "Synthesis and photochromic behavior under flash photolysis and continuous irradiation of novel 2H-chromenes derived from hydroxydibenzothiophenes", Tetrahedron, Feb. 25, 2002, pp. 1709-1718, 58(9).

Olsen, R., et al., "Secretase Inhibitors and Modulators for the Treatment of Alzheimer's Disease", Annual Report in Medicinal Chemistry, 2007, pp. 27-47, vol. 42.

Platonov, D., et al., "Synthesis of substituted 2-alkyl-5-hydroxy-1-oxo-1,2-dihydroisoquinolines and their new condensed structures", Mendeleev Communications, 2010, pp. 83-85, vol. 20.

Rivkin, A. et al., "Piperazinyl Pyrimidine Derivatives as Potent γ-Secretase Modulators", Bioorganic & Medicinal Chemistry Letters, Feb. 1, 2010, pp. 1269-1271, 20(3).

(56) References Cited

OTHER PUBLICATIONS

Rivkin, X., et al., "Purine Derivatives as Potent γ-Secretase Modulators", Bioorganic & Medicinal Chemistry Letters, Apr. 1, 2010, pp. 2279-2282, 20(7).

Sanz, R., et al., "Regioselective Synthesis of 4- and 7-Alkoxyindoles from 2,3-Dihalophenols: Application to the Preparation of Indole Inhibitors of Phospholipase $A_2$" Journal Organic Chemistry, Jun. 6, 2007, pp. 5113-5118, 72(14).

Shen, L., et al., "Synthesis and structure-activity relationships of thiadiazole-derivatives as potent and orally active peroxisome proliferator-activated receptors α/δ dual agonists", Bioorganic Medicinal Chemistry, Mar. 15, 2008, pp. 3321-3341, 16(6).

Shtarev, A.B., et al., "Partially Bridge-Fluorinated Dimethyl Bicyclo[1.1.1.]pentane-1,3-dicarboxylates: Preparation and NMR Spectra", Journal American Chemical Society, 2001, pp. 3484-3492,123(15).

Shultz, D.A., et al., "Design, Synthesis, and Properties of Conformationally Fixed Semiquinone Monoradical Species", Journal Organic Chemistry, Nov. 24, 2006, pp. 9104-9113, 71(24).

Tsunoda, T., et al., "1,1'-(Azodicarbonyl)dipiperidine-Tributylphosphines, A New Reagent System for Mitsunobu Reaction", Tetrahedron Letters, Mar. 5, 1993, pp. 1639-1642,34(10).

Van Camp, J.A., et al., "Preparation of 4-aryl-2-trifluoromethylbenzonitrile derivatives as androgen receptor antagonists for topical suppression of sebum production", Bioorganic & Medicinal Chemistry Letters, 2007, pp. 5529-5532, 17(20).

Wager, T.T., et al., "Defining Desirable Central Nervous System Drug Space through the Alignment of Molecular Properties, in Vitro ADME, and Safety Attributes", ACS Chemical Neuroscience, 2010, pp. 420-434,1(6).

Wai, J.S., et al., "Dihydroxypryridopyrazine-1,6-dione HIV-1 integrase inhibitors", Bioorganic & Medicinal Chemistry Letters, 2007, pp. 5595-5599, 17(20).

Zhang, J., et al., "TiCl4-Catalyzed Friedel-Crafts Reaction of Trifluoroacetaldehyde Ethyl Hemiacetal (TFAE)", Synthetic Communications, 2011, pp. 3045-3052, 41(20).

Zhu, Zhanoning, et al., "Discovery of Cyclic Acylguanidines as Highly Potent and Selective β-Site Amyloid Cleaving Enzyme (BACE) Inhibitors: Part 1-Inhibitor Design and Validation", Journal of Medicinal Chemistry Letters, 2010, pp. 951-965, 53(3).

Zoellinger, M., et al., "Skeleton Diversity by Cyclopropanation of Tricyclic Acylenamines", Journal of Chemical Sciences, 2009, pp. 617-623, 64(b).

Kawahara, N., et al., "A Synthesis of Pyrido[1,2-a]Quinoxalines and Pryrido[1,2-a]-Pyrazines[1]", Heterocycles, 1983, pp. 1721-1725, 20(9).

BICYCLIC PYRIDINONES

This application is a Non-Provisional application under 35 U.S.C. 119(e) which claims the benefit of U.S. Patent Application No. 61/599,022 filed on Feb. 15, 2012 which claims benefit of U.S. Patent Application No. 61/470,076 filed on Mar. 31, 2011.

The present invention relates to the treatment of Alzheimer's disease and other neurodegenerative and/or neurological disorders in mammals, including humans. This invention also relates to the modulation, in mammals, including humans, of the production of A-beta peptides that can contribute to the formation of neurological deposits of amyloid protein. More particularly, this invention relates to novel bicyclic pyridinone compounds useful for the treatment of neurodegenerative and/or neurological disorders, such as Alzheimer's disease and Down's Syndrome, related to A-beta peptide production.

BACKGROUND OF THE INVENTION

Dementia results from a wide variety of distinctive pathological processes. The most common pathological processes causing dementia are Alzheimer's disease (AD), cerebral amyloid angiopathy (CM) and prion-mediated diseases (see, e.g., Haan et al., Clin. Neurol. Neurosurg. 1990, 92(4):305-310; Glenner et al., J. Neurol. Sci. 1989, 94:1-28). AD affects nearly half of all people past the age of 85, the most rapidly growing portion of the United States population. As such, the number of AD patients in the United States is expected to increase from about 4 million to about 14 million by the middle of the next century.

The present invention relates to a group of brain-penetrable γ-secretase modulators useful as γ-secretase modulators for the treatment of neurodegenerative and/or neurological disorders that are related to A-beta peptide production, such as Alzheimer's disease and Down's Syndrome. (see Ann. Rep. Med. Chem. 2007, Olsen et al., 42: 27-47).

SUMMARY OF THE INVENTION

The present invention is directed to a compound of Formula I, including the pharmaceutically acceptable salts thereof,

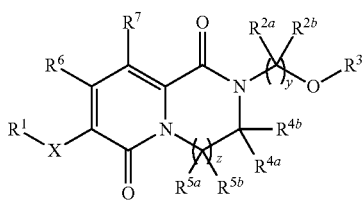

I wherein:

X is a 5- to 14-membered heteroaryl containing 1-3 heteroatoms;

$R^1$ is hydrogen, halogen, $C_{1-6}$alkyl, $C_{3-6}$cycloalkyl, $C_{2-6}$alkenyl or $C_{2-6}$alkynyl; wherein said alkyl, cycloalkyl, alkenyl or alkynyl may be optionally and independently substituted with one to three of fluoro, cyano, —$CF_3$, hydroxyl, or $C_{1-6}$alkoxy groups;

$R^{2a}$ and $R^{2b}$ for each occurrence are each independently hydrogen, fluoro, cyano, —$CF_3$, $C_{1-6}$alkyl, $C_{3-6}$cycloalkyl, $(C_{4-10})$bicycloalkyl, $C_{2-6}$alkenyl, $C_{2-6}$alkylidene, or $C_{2-6}$alkynyl; wherein said alkyl, cycloalkyl, bicycloalkyl, alkenyl, alkylidene or alkynyl may be optionally and independently substituted with cyano, $C_{1-3}$alkyl or one to three fluoro; or $R^{2a}$ and $R^{2b}$ together with the carbon to which they are bonded form a 3- to 5-membered cycloalkyl optionally substituted with one to three $R^8$;

$R^3$ is —$(C(R^{11})_2)_t$—$(C_{6-10}$aryl) or —$(C(R^{11})_2)_t$-(5- to 14-membered heteroaryl); wherein said aryl or heteroaryl moieties may be optionally independently substituted with one to five $R^{10}$;

$R^{4a}$ and $R^{4b}$ are each independently hydrogen, —$CF_3$, or $C_{1-6}$alkyl, wherein said alkyl is optionally substituted with one to three —$CF_3$, cyano or fluoro; or $R^{4a}$ and $R^{4b}$ together with the carbon to which they are bonded form a 3- to 5-membered cycloalkyl, wherein said cycloalkyl is optionally substituted with one to three of —$CF_3$, cyano, fluoro or $C_{1-6}$alkyl;

$R^{5a}$ and $R^{5b}$ for each occurrence are each independently hydrogen, —$CF_3$, or $C_{1-6}$alkyl, wherein said alkyl is optionally substituted with one to three —$CF_3$, cyano or fluoro; or $R^{5a}$ and $R^{5b}$ together with the carbon to which they are bonded form a 3- to 5-membered cycloalkyl, wherein said cycloalkyl is optionally substituted with one to three —$CF_3$, cyano, fluoro or $C_{1-6}$alkyl;

$R^6$, $R^7$ and $R^8$ are independently hydrogen, —$CF_3$, cyano, halogen, $C_{1-6}$alkyl or —$OR^9$; provided that $R^6$ and $R^7$ cannot both be —OH;

$R^9$ is hydrogen, $C_{1-6}$alkyl, $C_{3-6}$cycloalkyl, $C_{3-6}$alkenyl or $C_{3-6}$alkynyl; wherein said alkyl, cycloalkyl, alkenyl or alkynyl may be optionally and independently substituted with cyano, or one to three fluoro;

each $R^{10}$ is independently hydrogen, halogen, cyano, —$CF_3$, $C_{1-6}$alkyl, —$(C(R^{11})_2)_m$—$(C_{3-6}$cycloalkyl), —$(C(R^{11})_2)_m$—$((C_{4-10})$bicycloalkyl), —$(C(R^{11})_2)_m$-(4- to 10-membered heterocycloalkyl), —$(C(R^{11})_2)_m$—$(C_{6-10}$aryl), —$(C(R^{11})_2)_m$-(5- to 10-membered heteroaryl), —$(C(R^{11})_2)_m$—$OR^{12}$, —$C(O)R^{13}$, —$SF_5$ or —$Si(CH_3)_3$; wherein said alkyl, cycloalkyl, bicycloalkyl, heterocycloalkyl, aryl or heteroaryl moieties may be optionally and independently substituted with one to three $R^{14}$;

each $R^{11}$ is independently hydrogen, $C_{1-6}$alkyl, $C_{2-6}$alkenyl, $C_{2-6}$alkynyl, $C_{3-4}$cycloalkyl, fluoro, —$CF_3$, —$CHF_2$ or —$OR^{12}$; wherein said alkyl, alkenyl, alkynyl or cycloalkyl moieties may be optionally independently substituted with one to three fluoro or cyano;

each $R^{12}$ is independently hydrogen, $C_{1-6}$alkyl, —$CF_3$, —$(C(R^{14})_2)_n$—$(C_{3-6}$cycloalkyl), —$(C(R^{14})_2)_n$-(4- to 10-membered heterocycloalkyl), —$(C(R^{14})_2)_n$—$(C_{6-10}$aryl) or —$(C(R^{14})_2)_n$-(5- to 10-membered heteroaryl); wherein said alkyl, cycloalkyl, heterocycloalkyl, aryl or heteroaryl moieties may be optionally independently substituted with one to three $R^{16}$;

each $R^{13}$ is independently $C_{1-6}$alkyl, —$(C(R^{16})_2)_p$—$(C_{3-6}$cycloalkyl), —$(C(R^{16})_2)_p$-(4- to 10-membered heterocycloalkyl), —$(C(R^{16})_2)_p$—$(C_{6-10}$aryl) or —$(C(R^{16})_2)_p$-(5- to 10-membered heteroaryl); wherein said alkyl, cycloalkyl, heterocycloalkyl, aryl or heteroaryl moieties may be optionally independently substituted with one to three $R^{16}$;

each $R^{14}$ is independently hydrogen, $C_{1-6}$alkyl, $C_{2-6}$alkenyl, $C_{2-6}$alkynyl, halogen, cyano, —$CF_3$, —$CHF_2$, —$OR^9$ or —$OCF_3$;

$R^{16}$ is independently hydrogen, —$CF_3$, cyano, halogen, $C_{1-6}$alkyl or —$OR^9$; wherein said alkyl moiety may be optionally substituted with one to three $R^{17}$;

$R^{17}$ is independently hydrogen, hydroxyl, —$CF_3$, cyano, fluoro, $C_{2-6}$alkenyl or $C_{2-6}$alkynyl; wherein said alkenyl or alkynyl moiety may be optionally substituted with one to three hydrogen, fluoro or $C_{1-6}$alkyl; and each t, m, n or p is an integer independently selected from 0, 1, 2, 3, and 4;
z is an integer selected from 1 and 2;
y is an integer selected from 1, 2, 3 and 4
and pharmaceutically acceptable salts thereof.

In one embodiment, X is imidazolyl, pyrazolyl, isothiazolyl, thiazolyl, isoxazolyl, oxazolyl or pyridyl. In a preferred embodiment, X is imidazolyl.

In another embodiment, $R^1$ is $C_{1-6}$alkyl. In a preferred embodiment, $R^1$ is methyl, y is two or three and z is 1.

In one embodiment, $R^3$ is aryl or heteroaryl. In a preferred embodiment, $R^3$ is phenyl, naphthalene, 2,3-dihydro-1H-indene, quinoline, isoquinoline, pyrazole, benzo[b]furan, 2,3-dihydrobenzofuran, 1,2-benzisothiazole, 1,3-benzothiazole, benzofuro[3,2-c]pyridine, pyridine, carbazole, benzo[d]isoxazole, benzocyclobutane, 1,2,3,4-tetrahydronaphthalene, dibenzo[b,d]thiophene, dibenzo[b,d]furan or cinnoline.

In one embodiment, $R^{10}$ is independently hydrogen, halogen, cyano, —$CF_3$, $C_{1-6}$alkyl, ($C_{4-10}$)bicycloalkyl, —$(C(R^{11})_2)_m$—($C_{3-6}$cycloalkyl), —$(C(R^{11})_2)_m$-(4- to 10-membered heterocycloalkyl), —$(C(R^{11})_2)_m$—($C_{6-10}$aryl), —$(C(R^{11})_2)_m$-(5- to 10-membered heteroaryl), —$(C(R^{11})_2)_m$—$OR^{12}$ or —$C(O)R^{13}$; wherein the alkyl, cycloalkyl, heterocycloalkyl, aryl, or heteroaryl moieties may be independently substituted with one to three $R^{14}$. In a preferred embodiment, $R^{10}$ is hydrogen, chloro, fluoro, bromo, cyano, —$CF_3$, —$OCF_3$, methyl, ethyl, propyl, isopropyl, butyl, tert-butyl, cyclopropyl, cyclobutyl, bicycloalkyl, hydroxyl, methoxy, pyrazole, isothiazole, thiazole, 1,3,4-thiadiazole, isoxazole, oxazole, pyridine, piperidine, benzofuran, benzo[d][1,3]dioxole, tetrahydropyrane or phenyl; wherein said $C_{1-6}$alkyl, bicycloalkyl, cycloalkyl, heterocycloalkyl, heteroaryl or aryl moieties may be optionally independently substituted with one to three $R^{14}$.

In a preferred embodiment, $R^3$ is phenyl, naphthalene, 2,3-dihydro-1H-indene, quinoline, isoquinoline, pyrazole, benzo[b]furan, 2,3-dihydrobenzofuran, 1,2-benzisothiazole, 1,3-benzothiazole, benzofuro[3,2-c]pyridine, pyridine, carbazole, benzo[d]isoxazole, 1,2,3,4-tetrahydronaphthalene, dibenzo[b,d]thiophene, dibenzo[b,d]furan, benzoyclobutane or cinnoline;

$R^{4a}$, $R^{4b}$, $R^{5a}$, $R^{5b}$, $R^6$, $R^7$ and $R^8$ are each independently hydrogen or $C_{1-6}$alkyl;

$R^{14}$ is independently hydrogen, $C_{1-6}$alkyl, chloro, bromo or fluoro, —$CF_3$, —$CHF_2$ or —$OR^9$;

and $R^{17}$ is independently hydrogen or —$CF_3$ or phenyl; wherein said phenyl and $C_{1-6}$alkyl moieties may be independently substituted with one to three hydrogen or halogen;

or a pharmaceutically acceptable salt thereof.

In one embodiment, the invention also relates to each of the individual compounds described as Examples 1-116 in the Examples section of the subject application, (including the free bases or pharmaceutically acceptable salts thereof).

In another embodiment the invention relates to a preferred compound selected from the group consisting of:
7-(4-methyl-1H-imidazol-1-yl)-2-(2-{2-[2-(trifluoromethyl)-1,3-thiazol-4-yl]phenoxy}ethyl)-3,4-dihydro-2H-pyrido[1,2-a]pyrazine-1,6-dione;
2-{(1S)-2-[4-fluoro-2-(trifluoromethyl)phenoxy]-1-methylethyl}-7-(4-methyl-1H-imidazol-1-yl)-3,4-dihydro-2H-pyrido[1,2-a]pyrazine-1,6-dione;
7-(4-methyl-1H-imidazol-1-yl)-2-(2-{2-[3-(trifluoromethyl)isoxazol-5-yl]phenoxy}ethyl)-3,4-dihydro-2H-pyrido[1,2-a]pyrazine-1,6-dione;
2-(2-{[4-fluoro-2-(trifluoromethyl)-1,3-benzothiazol-7-yl]oxy}ethyl)-7-(4-methyl-1H-imidazol-1-yl)-3,4-dihydro-2H-pyrido[1,2-a]pyrazine-1,6-dione;
2-{2-[2-(3,3-difluorocyclobutyl)-4-fluorophenoxy]ethyl}-7-(4-methyl-1H-imidazol-1-yl)-3,4-dihydro-2H-pyrido[1,2-a]pyrazine-1,6-dione;
7-(4-methyl-1H-imidazol-1-yl)-2-(2-{[2-(trifluoromethyl)-1,3-benzothiazol-7-yl]oxy}ethyl)-3,4-dihydro-2H-pyrido[1,2-a]pyrazine-1,6-dione, trifluoroacetate salt;
7-(4-methyl-1H-imidazol-1-yl)-2-(2-{2-[3-(trifluoromethyl)-1,2,4-thiadiazol-5-yl]phenoxy}ethyl)-3,4-dihydro-2H-pyrido[1,2-a]pyrazine-1,6-dione;
2-{2-[4-fluoro-2-(1,1,1-trifluoro-2-methylpropan-2-yl)phenoxy]ethyl}-7-(4-methyl-1H-imidazol-1-yl)-3,4-dihydro-2H-pyrido[1,2-a]pyrazine-1,6-dione;
2-{2-[2-(bicyclo[1.1.1]pent-1-yl)phenoxy]ethyl}-7-(4-methyl-1H-imidazol-1-yl)-3,4-dihydro-2H-pyrido[1,2-a]pyrazine-1,6-dione;
2-{(2S)-1-[4-chloro-2-(trifluoromethyl)phenoxy]propan-2-yl}-7-(4-methyl-1H-imidazol-1-yl)-3,4-dihydro-2H-pyrido[1,2-a]pyrazine-1,6-dione;
2-{2-[(2,2-difluoro-2,3-dihydro-1H-inden-4-yl)oxy]ethyl}-7-(4-methyl-1H-imidazol-1-yl)-3,4-dihydro-2H-pyrido[1,2-a]pyrazine-1,6-dione;
2-{2-[(2,2-difluoro-1,3-benzodioxol-4-yl)oxy]ethyl}-7-(4-methyl-1H-imidazol-1-yl)-3,4-dihydro-2H-pyrido[1,2-a]pyrazine-1,6-dione; and
2-{2-[2-(bicyclo[1.1.1]pent-1-yl)-4-chlorophenoxy]ethyl}-7-(4-methyl-1H-imidazol-1-yl)-3,4-dihydro-2H-pyrido[1,2-a]pyrazine-1,6-dione
or a pharmaceutically acceptable salt of any of the above.

Yet another aspect of this invention is directed to a method for treating conditions or diseases of the central nervous system identified to have enhanced gamma secretase activity, such as Niemann Pick type C; neurological disorder (such as migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV associated dementia, Alzheimer's disease, Huntington's disease, Lewy body dementia, vascular dementia, drug related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment); mental deficiency (including spasticity, Down syndrome and fragile X syndrome); sleep disorders (including hypersomnia, circadian rhythm sleep disorder, insomnia, parasomnia, and sleep deprivation) and psychiatric disorders (such as anxiety (including acute stress disorder, generalized anxiety disorder, social anxiety disorder, panic disorder, post-traumatic stress disorder, agoraphobia, and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, seasonal depression, premenstrual syndrome (PMS) premenstrual dysphoric disorder (PDD), and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, obesity, compulsive eating disorders and pagophagia); sexual dysfunction disorders, urinary incontinence; neuronal damage disorders (including ocular damage, retinopathy or macular degeneration of the eye, tinnitus, hearing impairment and loss, and brain edema) and pediatric psychiatric disorders (including attention deficit disorder, attention deficit/hyperactive disorder, conduct disorder, and autism) in a mammal, preferably a human, comprising administering to said mammal a therapeutically effective amount of a compound of Formula I or pharmaceutically acceptable salt thereof.

Compounds of Formula I may also be useful for improving memory (both short term and long term) and learning ability.

The text revision of the fourth edition of the Diagnostic and Statistical Manual of Mental Disorders (DSM-IV-TR) (2000, American Psychiatric Association, Washington D.C.) provides a diagnostic tool for identifying many of the disorders described herein. The skilled artisan will recognize that there are alternative nomenclatures, nosologies, and classification systems for disorders described herein, including those as described in the DMS-IV and that terminology and classification systems evolve with medical scientific progress.

Preferred methods are for treating a neurological disorder (such as migraine; epilepsy; Alzheimer's disease; Parkinson's disease; Niemann Pick type C; brain injury; stroke; cerebrovascular disease; cognitive disorder; sleep disorder) or a psychiatric disorder (such as anxiety; factitious disorder; impulse control disorder; mood disorder; psychomotor disorder; psychotic disorder; drug dependence; eating disorder; and pediatric psychiatric disorder) in a mammal, preferably a human, comprising administering to said mammal a therapeutically effective amount of a compound of Formula I or pharmaceutically acceptable salt thereof.

Also provided herein are compositions comprising a pharmaceutically effective amount of one or more of the compounds described herein and a pharmaceutically acceptable vehicle, carrier or excipient.

The present invention includes the use of a combination of a γ-secretase modulator compound as provided in Formula I and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of Formula I, depending on the disease, disorder, or condition to be treated. Pharmaceutically active agents that may be used in combination with the compositions of the present invention include, without limitation:

(i) acetylcholinesterase inhibitors, such as donepezil hydrochloride (ARICEPT, MEMAC), physostigmine salicylate (ANTILIRIUM), physostigmine sulfate (ESERINE), metrifonate, neostigmine, ganstigmine, pyridostigmine (MESTINON), ambenonium (MYTELASE), demarcarium, Debio 9902 (also known as ZT-1; Debiopharm), rivastigmine (EXELON), ladostigil, NP-0361, galantamine hydrobromide (RAZADYNE, RIMINYL, NIVALIN), tacrine (COGNEX), tolserine, velnacrine maleate, memoquin, huperzine A (HUP-A; NeuroHitech), phenserine, edrophonium (ENLON, TENSILON), and INM-176;

(ii) amyloid-β (or fragments thereof), such as $A\beta_{1-15}$ conjugated to pan HLA DR-binding epitope (PADRE), ACC-001 (Elan/Wyeth), ACI-01, ACI-24, AN-1792, Affitope AD-01, CAD106, and V-950;

(iii) antibodies to amyloid-β (or fragments thereof), such as ponezumab, solanezumab, bapineuzumab (also known as AAB-001), AAB-002 (Wyeth/Elan), ACI-01-Ab7, BAN-2401, intravenous Ig (GAMMAGARD), LY2062430 (humanized m266; Lilly), R1450 (Roche), ACU-5A5, huC091, and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(iv) amyloid-lowering or -inhibiting agents (including those that reduce amyloid production, accumulation and fibrillization) such as dimebon, davunetide, eprodisate, leuprolide, SK-PC-B70M, celecoxib, lovastatin, anapsos, oxiracetam, pramiracetam, varenicline, nicergoline, colostrinin, bisnorcymserine (also known as BNC), NIC5-15 (Humanetics), E-2012 (Eisai), pioglitazone, clioquinol (also known as PBT1), PBT2 (Prana Biotechnology), flurbiprofen (ANSAID, FROBEN) and its R-enantiomer tarenflurbil (FLURIZAN), nitroflurbiprofen, fenoprofen (FENOPRON, NALFON), ibuprofen (ADVIL, MOTRIN, NUROFEN), ibuprofen lysinate, meclofenamic acid, meclofenamate sodium (MECLOMEN), indomethacin (INDOCIN), diclofenac sodium (VOLTAREN), diclofenac potassium, sulindac (CLINORIL), sulindac sulfide, diflunisal (DOLOBID), naproxen (NAPROSYN), naproxen sodium (ANAPROX, ALEVE), ARC031 (Archer Pharmaceuticals), CAD-106 (Cytos), LY450139 (Lilly), insulin-degrading enzyme (also known as insulysin), the gingko biloba extract EGb-761 (ROKAN, TEBONIN), tramiprosate (CEREBRIL, ALZHEMED), eprodisate (FIBRILLEX, KIACTA), compound W (3,5-bis (4-nitrophenoxy)benzoic acid), NGX-96992, neprilysin (also known as neutral endopeptidase (NEP)), scyllo-inositol (also known as scyllitol), atorvastatin (LIPITOR), simvastatin (ZOCOR), KLVFF-(EEX)3, SKF-74652, ibutamoren mesylate, BACE inhibitors such as ASP-1702, SCH-745966, JNJ-715754, AMG-0683, AZ-12304146, BMS-782450, GSK-188909, NB-533, E2609 and TTP-854; Gamma Secretase Modulators such as ELND-007; and RAGE (receptor for advanced glycation end-products) inhibitors, such as TTP488 (Transtech) and TTP4000 (Transtech), and those disclosed in U.S. Pat. No. 7,285,293, including PTI-777;

(v) alpha-adrenergic receptor agonists, such as guanfacine (INTUNIV, TENEX), clonidine (CATAPRES), metaraminol (ARAMINE), methyldopa (ALDOMET, DOPAMET, NOVOMEDOPA), tizanidine (ZANAFLEX), phenylephrine (also known as neosynephrine), methoxamine, cirazoline, guanfacine (INTUNIV), lofexidine, xylazine, modafinil (PROVIGIL), adrafinil, and armodafinil (NUVIGIL);

(vi) beta-adrenergic receptor blocking agents (beta blockers), such as carteolol, esmolol (BREVIBLOC), labetalol (NORMODYNE, TRANDATE), oxprenolol (LARACOR, TRASACOR), pindolol (VISKEN), propanolol (INDERAL), sotalol (BETAPACE, SOTALEX, SOTACOR), timolol (BLOCADREN, TIMOPTIC), acebutolol (SECTRAL, PRENT), nadolol (CORGARD), metoprolol tartrate (LOPRESSOR), metoprolol succinate (TOPROL-XL), atenolol (TENORMIN), butoxamine, and SR 59230A (Sanofi);

(vii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE), tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(viii) anticonvulsants, such as carbamazepine (TEGRETOL, CARBATROL), oxcarbazepine (TRILEPTAL), phenyloin sodium (PHENYTEK), fosphenyloin (CEREBYX, PRODILANTIN), divalproex sodium (DEPAKOTE), gabapentin (NEURONTIN), pregabalin (LYRICA), topirimate (TOPAMAX), valproic acid (DEPAKENE), valproate sodium (DEPACON), 1-benzyl-5-bromouracil, progabide, beclamide, zonisamide (TRERIEF, EXCEGRAN), CP-465022, retigabine, talampanel, and primidone (MYSOLINE);

(ix) antipsychotics, such as lurasidone (LATUDA, also known as SM-13496; Dainippon Sumitomo), aripiprazole (ABILIFY), chlorpromazine (THORAZINE), haloperidol (HALDOL), iloperidone (FANAPTA), flupentixol decanoate (DEPIXOL, FLUANXOL), reserpine (SERPLAN), pimozide (ORAP), fluphenazine decanoate, fluphenazine hydrochloride, prochlorperazine (COMPRO), asenapine (SAPHRIS), loxapine (LOXITANE), molindone (MOBAN), perphenazine, thioridazine, thiothixine, trifluoperazine (STELAZINE), ramelteon, clozapine (CLOZARIL), norclozapine (ACP-104), risperidone (RISPERDAL), paliperidone (INVEGA), melperone, olanzapine (ZYPREXA), quetiapine (SEROQUEL), talnetant, amisulpride, ziprasidone (GEODON), blonanserin (LONASEN), and ACP-103 (Acadia Pharmaceuticals);

(x) calcium channel blockers such as lomerizine, ziconotide, nilvadipine (ESCOR, NIVADIL), diperdipine, amlodipine (NORVASC, ISTIN, AMLODIN), felodipine (PLENDIL), nicardipine (CARDENE), nifedipine (ADALAT, PROCARDIA), MEM 1003 and its parent compound nimodipine (NIMOTOP), nisoldipine (SULAR), nitrendipine, lacidipine (LACIPIL, MOTENS), lercanidipine (ZANIDIP), lifarizine, diltiazem (CARDIZEM), verapamil (CALAN, VERELAN), AR-R 18565 (AstraZeneca), and enecadin;

(xi) catechol O-methyltransferase (COMT) inhibitors, such as nitecapone, tolcapone (TASMAR), entacapone (COMTAN), and tropolone;

(xii) central nervous system stimulants, such as atomoxetine, reboxetine, yohimbine, caffeine, phenmetrazine, phendimetrazine, pemoline, fencamfamine (GLUCOENERGAN, REACTIVAN), fenethylline (CAPTAGON), pipradol (MERETRAN), deanol (also known as dimethylaminoethanol), methylphenidate (DAYTRANA), methylphenidate hydrochloride (RITALIN), dexmethylphenidate (FOCALIN), amphetamine (alone or in combination with other CNS stimulants, e.g. ADDERALL (amphetamine aspartate, amphetamine sulfate, dextroamphetamine saccharate, and dextroamphetamine sulfate)), dextroamphetamine sulfate (DEXEDRINE, DEXTROSTAT), methamphetamine (DESOXYN), lisdexamfetamine (VYVANSE), and benzphetamine (DIDREX);

(xiii) corticosteroids, such as prednisone (STERAPRED, DELTASONE), prednisolone (PRELONE), predisolone acetate (OMNIPRED, PRED MILD, PRED FORTE), prednisolone sodium phosphate (ORAPRED ODT), methylprednisolone (MEDROL); methylprednisolone acetate (DEPO-MEDROL), and methylprednisolone sodium succinate (A-METHAPRED, SOLU-MEDROL);

(xiv) dopamine receptor agonists, such as apomorphine (APOKYN), bromocriptine (PARLODEL), cabergoline (DOSTINEX), dihydrexidine, dihydroergocryptine, fenoldopam (CORLOPAM), lisuride (DOPERGIN), terguride spergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), cariprazine, pardoprunox and sarizotan;

(xv) dopamine receptor antagonists, such as chlorpromazine, fluphenazine, haloperidol, loxpine, resperidone, thioridazine, thiothixene, trifluoperazine, tetrabenazine (NITOMAN, XENAZINE), 7-hydroxyamoxapine, droperidol (INAPSINE, DRIDOL, DROPLETAN), domperidone (MOTILIUM), L-741742, L-745870, raclopride, SB-277011A, SCH-23390, ecopipam, SKF-83566, and metoclopramide (REGLAN);

(xvi) dopamine reuptake inhibitors such as bupropion, safinamide, nomifensine maleate (MERITAL), vanoxerine (also known as GBR-12909) and its decanoate ester DBL-583, and amineptine;

(xvii) gamma-amino-butyric acid (GABA) receptor agonists, such as baclofen (LIORESAL, KEMSTRO), siclofen, pentobarbital (NEMBUTAL), progabide (GABRENE), and clomethiazole;

(xviii) histamine 3 (H3) antagonists such as ciproxifan, tiprolisant, S-38093, irdabisant, pitolisant, GSK-239512, GSK-207040, JNJ-5207852, JNJ-17216498, HPP-404, SAR-110894, trans-3-fluoro-3-(3-fluoro-4-pyrrolidin-1-yl-methyl-phenyl)-cyclobutane carboxylic acid ethylamide (PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xix) immunomodulators such as glatiramer acetate (also known as copolymer-1; COPAXONE), MBP-8298 (synthetic myelin basic protein peptide), dimethyl fumarate, fingolimod (also known as FTY720), roquinimex (LINOMIDE), laquinimod (also known as ABR-215062 and SAIK-MS), ABT-874 (human anti-IL-12 antibody; Abbott), rituximab (RITUXAN), alemtuzumab (CAMPATH), daclizumab (ZENAPAX), and natalizumab (TYSABRI);

(xx) immunosuppressants such as methotrexate (TREXALL, RHEUMATREX), mitoxantrone (NOVANTRONE), mycophenolate mofetil (CELLCEPT), mycophenolate sodium (MYFORTIC), azathioprine (AZASAN, IMURAN), mercaptopurine (PURI-NETHOL), cyclophosphamide (NEOSAR, CYTOXAN), chlorambucil (LEUKERAN), cladribine (LEUSTATIN, MYLINAX), alpha-fetoprotein, etanercept (ENBREL), and 4-benzyloxy-5-((5-undecyl-2H-pyrrol-2-ylidene)methyl)-2,2'-bi-1H-pyrrole (also known as PNU-156804);

(xxi) interferons, including interferon beta-1a (AVONEX, REBIF) and interferon beta-1b (BETASERON, BETAFERON);

(xxii) levodopa (or its methyl or ethyl ester), alone or in combination with a DOPA decarboxylase inhibitor (e.g. carbidopa (SINEMET, CARBILEV, PARCOPA), benserazide (MADOPAR), α-methyldopa, monofluoromethyldopa, difluoromethyldopa, brocresine, or m-hydroxybenzylhydrazine);

(xxiii) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), LY-233536 and LY-235959 (both Lilly), methadone, (DOLOPHINE), neramexane, perzinfotel, phencyclidine, tianeptine (STABLON), dizocilpine (also known as MK-801), EAB-318 (Wyeth), ibogaine, voacangine, tiletamine, riluzole (RILUTEK), aptiganel (CERESOTAT), gavestinel, and remacimide;

(xxiv) monoamine oxidase (MAO) inhibitors, such as selegiline (EMSAM), selegiline hydrochloride (l-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xxv) muscarinic receptor (particularly M1 subtype) agonists, such as cevimeline, levetiracetam, bethanechol chloride (DUVOID, URECHOLINE), itameline, pilocarpine (SALAGEN), NGX267, arecoline, L-687306 (Merck), L-689660 (Merck), furtrethonium iodide (FURAMON, FURANOL), furtrethonium benzensulfonate, furtrethonium p-toluenesulfonate, McN-A-343, oxotremorine, sabcomeline, AC-90222 (Acadia Pharmaceuticals), and carbachol (CARBASTAT, MIOSTAT, CARBOPTIC);

(xxvi) neuroprotective drugs such as bosutinib, condoliase, airmoclomol, lamotrigine, perampanel, aniracetam, minaprime, viluzole 2,3,4,9-tetrahydro-1H-carbazol-3-one oxime, desmoteplase, anatibant, astaxanthin, neuropeptide NAP (e.g. AL-108 and AL-208; both Allon Therapeutics), neurostrol, perampenel, ispronicline, bis(4-β-D-glucopyranosyloxybenzyl)-2-β-D-glucopyranosyl-2-isobutyltartrate (also known as dactylorhin B or DHB), formobactin, xaliproden (XAPRILA), lactacystin, dimeboline hydrochloride (DIMEBON), disufenton (CEROVIVE), arundic acid (ONO-2506, PROGLIA, CEREACT), citicoline (also known as cytidine 5'-diphosphocholine), edaravone (RADICUT), AEOL-10113 and AEOL-10150 (both Aeolus Pharmaceuticals), AGY-94806 (also known as SA-450 and Msc-1), granulocyte-colony stimulating factor (also known as AX-200), BAY-38-7271 (also known as KN-387271; Bayer AG), ancrod (VIPRINEX, ARWIN), DP-b99 (D-Pharm Ltd), HF-0220 (17-β-hydroxyepiandrosterone; Newron Pharmaceuticals), HF-0420 (also known as oligotropin), pyridoxal 5'-phosphate (also known as MC-1), microplasmin, S-18986, piclozotan, NP031112, tacrolimus, L-seryl-L-methionyl-L-alanyl-L-lysyl-L-glutamyl-glycyl-L-valine, AC-184897 (Acadia Pharmaceuticals), ADNF-14 (National Institutes of Health), stilbazulenyl nitrone, SUN-N8075 (Daiichi Suntory Biomedical Research), and zonampanel;

(xxvii) nicotinic receptor agonists, such as epibatidine, bupropion, CP-601927, varenicline, ABT-089 (Abbott), ABT-594, AZD-0328 (AstraZeneca), EVP-6124, R3487 (also known as MEM3454; Roche/Memory Pharmaceuticals), R4996 (also known as MEM63908; Roche/Memory Pharmaceuticals), TC-4959 and TC-5619 (both Targacept), and RJR-2403;

(xxviii) norepinephrine (noradrenaline) reuptake inhibitors, such as atomoxetine (STRATTERA), doxepin (APONAL, ADAPIN, SINEQUAN), nortriptyline (AVENTYL, PAMELOR, NORTRILEN), amoxapine (ASENDIN, DEMOLOX, MOXIDIL), reboxetine (EDRONAX, VESTRA), viloxazine (VIVALAN), maprotiline (DEPRILEPT, LUDIOMIL, PSYMION), bupropion (WELLBUTRIN), and radaxafine;

(xxix) phosphodiesterase (PDE) inhibitors, including (a) PDE1 inhibitors (e.g. vinpocetine (CAVINTON, CERACTIN, INTELECTOL) and those disclosed in U.S. Pat. No. 6,235,742, (b) PDE2 inhibitors (e.g. erythro-9-(2-hydroxy-3-nonyl)adenine (EHNA), BAY 60-7550, and those described in U.S. Pat. No. 6,174,884), (c) PDE3 inhibitors (e.g. anagrelide, cilostazol, milrinone, olprinone, parogrelil, and pimobendan), (d) PDE4 inhibitors (e.g. apremilast, ibudilastrofumilast, rolipram, Ro 20-1724, ibudilast (KETAS), piclamilast (also known as RP73401), CDP840, cilomilast (ARIFLO), roflumilast, tofimilast, oglemilast (also known as GRC 3886), tetomilast (also known as OPC-6535), lirimifast, theophylline (UNIPHYL, THEOLAIR), arofylline (also known as LAS-31025), doxofylline, RPR-122818, or mesembrine), and (e) PDE5 inhibitors (e.g. sildenafil (VIAGRA, REVATIO), tadalafil (CIALIS), vardenafil (LEVITRA, VIVANZA), udenafil, avanafil, dipyridamole (PERSANTINE), E-4010, E-4021, E-8010, zaprinast, iodenafil, mirodenafil, DA-8159, and those disclosed in International Patent Applications WO2002/020521, WO2005/049616, WO2006/120552, WO2006/126081, WO2006/126082, WO2006/126083, and WO2007/122466), (f) PDE9 inhibitors (e.g. BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), and (g) PDE10 inhibitor such as 2-[4-(1-Methyl-4-pyridin-4-yl-1H-pyrazol-3-yl)phenoxymethyl]quinoline (PF-2545920), and SCH-1518291;

(xxx) quinolines, such as quinine (including its hydrochloride, dihydrochloride, sulfate, bisulfate and gluconate salts), chloroquine, sontoquine, hydroxychloroquine (PLAQUENIL), mefloquine (LARIAM), and amodiaquine (CAMOQUIN, FLAVOQUINE);

(xxxi) β-secretase inhibitors, such as ASP-1702, SCH-745966, JNJ-715754, AMG-0683, AZ-12304146, BMS-782450, GSK-188909, NB-533, LY-2886721, E-2609, HPP-854, (+)-phenserine tartrate (POSIPHEN), LSN-2434074 (also known as LY-2434074), KMI-574, SCH-745966, Ac-rER ($N^2$-acetyl-D-arginyl-L-arginine), loxistatin (also known as E64d), and CA074Me;

(xxxii) γ-secretase inhibitors and modulators, such as BMS-708163 (Avagacest), WO20060430064 (Merck), DSP8658 (Dainippon), ITI-009, L-685458 (Merck), ELAN-G, ELAN-Z, 4-chloro-N-[2-ethyl-1(S)-(hydroxymethyl)butyl]benzenesulfonamide;

(xxxiii) serotonin (5-hydroxytryptamine) 1A ($5-HT_{1A}$) receptor antagonists, such as spiperone, levo-pindolol, BMY 7378, NAD-299, S(−)-UH-301, NAN 190, lecozotan;

(xxxiv) serotonin (5-hydroxytryptamine) 2C (5-HT2c) receptor agonists, such as vabicaserin, and zicronapine;

(xxxv) serotonin (5-hydroxytryptamine) 4 ($5-HT_4$) receptor agonists, such as PRX-03140 (Epix);

(xxxvi) serotonin (5-hydroxytryptamine) 6 ($5-HT_6$) receptor antagonists, such as A-964324, AVI-101, AVN-211, mianserin (TORVOL, BOLVIDON, NORVAL), methiothepin (also known as metitepine), ritanserin, ALX-1161, ALX-1175, MS-245, LY-483518 (also known as SGS518; Lilly), MS-245, Ro 04-6790, Ro 43-68544, Ro 63-0563, Ro 65-7199, Ro 65-7674, SB-399885, SB-214111, SB-258510, SB-271046, SB-357134, SB-699929, SB-271046, SB-742457 (GlaxoSmithKline), Lu AE58054 (Lundbeck A/S), and PRX-07034 (Epix);

(xxxvii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine, neuralstem and tesofensine;

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline, idebenone, PYM50028 (COGANE; Phytopharm), and AIT-082 (NEOTROFIN);

(xxxix) Glycine transporter-1 inhibitors such as paliflutine, ORG-25935, JNJ-17305600, and ORG-26041;

(xl) AMPA-type glutamate receptor modulators such as perampanel, mibampator, selurampanel, GSK-729327, and N-((3S,4S)-4-(4-(5-cyanothiophen-2-yl)phenoxy)tetrahydrofuran-3-yl)propane-2-sulfonamide;

and the like.

All patents, patent applications and references referred to herein are hereby incorporated by reference in their entirety.

Other features and advantages of this invention will be apparent from this specification and the appendent claims which describe the invention.

DEFINITIONS

The term "alkyl" refers to a linear or branched-chain saturated hydrocarbyl substituent (i.e., a substituent obtained from a hydrocarbon by removal of a hydrogen) containing from one to twenty carbon atoms; in one embodiment from one to twelve carbon atoms; in another embodiment, from one to ten carbon atoms; in another embodiment, from one to six carbon atoms; and in another embodiment, from one to four carbon atoms. Examples of such substituents include methyl, ethyl, propyl (including n-propyl and isopropyl), butyl (including n-butyl, isobutyl, sec-butyl and tert-butyl), pentyl, isoamyl, hexyl and the like. In some instances, the number of carbon atoms in a hydrocarbyl moiety (i.e., alkyl, cycloalkyl, etc.) is indicated by the prefix "$C_{x-y}$," wherein x is the minimum and y is the maximum number of carbon atoms in the substituent. Thus, for example, "$C_{1-6}$alkyl" refers to an alkyl substituent containing from 1 to 6 carbon atoms.

"Alkenyl" refers to an aliphatic hydrocarbon having at least one carbon-carbon double bond, including straight chain, branched chain or cyclic groups having at least one carbon-carbon double bond. Preferably, it is a medium-size alkenyl having 2 to 6 carbon atoms. For example, as used herein, the term "$C_{2-6}$alkenyl" means straight or branched chain unsaturated radicals of 2 to 6 carbon atoms, including, but not limited to ethenyl, 1-propenyl, 2-propenyl (allyl), isopropenyl, 2-methyl-1-propenyl, 1-butenyl, 2-butenyl, and the like; optionally substituted by 1 to 5 suitable substituents as defined above such as fluoro, chloro, trifluoromethyl, ($C_1$-$C_6$) alkoxy, ($C_6$-$C_{10}$)aryloxy, trifluoromethoxy, difluoromethoxy or ($C_1$-$C_6$)alkyl. When the compounds of the invention contain a $C_{2-6}$alkenyl group, the compound may exist as the pure E (entgegen) form, the pure Z (zusammen) form, or any mixture thereof.

"Alkylidene" refers to a divalent group formed from an alkane by removal of two hydrogen atoms from the same carbon atom, the free valencies of which are part of a double bond.

"Alkynyl" refers to an aliphatic hydrocarbon having at least one carbon-carbon triple bond, including straight chain, branched chain or cyclic groups having at least one carbon-carbon triple bond. Preferably, it is a lower alkynyl having 2 to 6 carbon atoms. For example, as used herein, the term "$C_{2-6}$alkynyl" is used herein to mean a straight or branched hydrocarbon chain alkynyl radical as defined above having 2 to 6 carbon atoms and one triple bond.

The term "cycloalkyl" refers to a carbocyclic substituent obtained by removing a hydrogen from a saturated carbocyclic molecule and having three to fourteen carbon atoms. In one embodiment, a cycloalkyl substituent has three to ten carbon atoms. Examples of cycloalkyl include cyclopropyl, cyclobutyl, cyclopentyl and cyclohexyl.

The term "cycloalkyl" also includes substituents that are fused to a $C_6$-$C_{10}$ aromatic ring or to a 5- to 10-membered heteroaromatic ring, wherein a group having such a fused cycloalkyl group as a substituent is bound to a carbon atom of the cycloalkyl group. When such a fused cycloalkyl group is substituted with one or more substituents, the one or more substituents, unless otherwise specified, are each bound to a carbon atom of the cycloalkyl group. The fused $C_6$-$C_{10}$ aromatic ring or 5- to 10-membered heteroaromatic ring may be optionally substituted with halogen, $C_{1-6}$alkyl, $C_{3-10}$cycloalkyl, or =O.

A cycloalkyl may be a single ring, which typically contains from 3 to 6 ring atoms. Examples include cyclopropyl, cyclobutyl, cyclopentyl, and cyclohexyl. Alternatively, 2 or 3 rings may be fused together, such as bicyclodecanyl and decalinyl. The term "cycloalkyl" also includes bridged bicycloalkyl systems such as, but not limited to, bicyclo[2.2.1]heptane and bicyclo[1.1.1]pentane.

The term "aryl" refers to an aromatic substituent containing one ring or two or three fused rings. The aryl substituent may have six to eighteen carbon atoms. As an example, the aryl substituent may have six to fourteen carbon atoms. The term "aryl" may refer to substituents such as phenyl, naphthyl and anthracenyl. The term "aryl" also includes substituents such as phenyl, naphthyl and anthracenyl that are fused to a $C_{4-10}$ carbocyclic ring, such as a $C_5$ or a $C_6$ carbocyclic ring, or to a 4- to 10-membered heterocyclic ring, wherein a group having such a fused aryl group as a substituent is bound to an aromatic carbon of the aryl group. When such a fused aryl group is substituted with one or more substituents, the one or more substituents, unless otherwise specified, are each bound to an aromatic carbon of the fused aryl group. The fused $C_{4-10}$ carbocyclic or 4- to 10-membered heterocyclic ring may be optionally substituted with halogens, $C_{1-6}$alkyl, $C_{3-10}$cycloalkyl, or =O. Examples of aryl groups include accordingly phenyl, naphthalenyl, tetrahydronaphthalenyl (also known as "tetralinyl"), indenyl, isoindenyl, indanyl, anthracenyl, phenanthrenyl, benzonaphthenyl (also known as "phenalenyl"), and fluorenyl.

The term "hydrogen" refers to a hydrogen substituent, and may be depicted as —H.

The term "hydroxy" or "hydroxyl" refers to —OH. When used in combination with another term(s), the prefix "hydroxy" indicates that the substituent to which the prefix is attached is substituted with one or more hydroxy substituents.

Compounds bearing a carbon to which one or more hydroxy substituents are attached include, for example, alcohols, enols and phenol.

The term "cyano" (also referred to as "nitrile") means —CN, which also may be depicted:

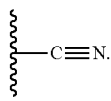

The term "halogen" refers to fluorine (which may be depicted as —F), chlorine (which may be depicted as —Cl), bromine (which may be depicted as —Br), or iodine (which may be depicted as —I). In one embodiment, the halogen is chlorine. In another embodiment, the halogen is fluorine. In another embodiment, the halogen is bromine.

The term "heterocycloalkyl" refers to a substituent obtained by removing a hydrogen from a saturated or partially saturated ring structure containing a total of 4 to 14 ring atoms, wherein at least one of the ring atoms is a heteroatom selected from oxygen, nitrogen, or sulfur. For example, as used herein, the term "4- to 10-membered heterocycloalkyl" means the substituent is a single ring with 4 to 10 total members. A heterocycloalkyl alternatively may comprise 2 or 3 rings fused together, wherein at least one such ring contains a heteroatom as a ring atom (i.e., nitrogen, oxygen, or sulfur). In a group that has a heterocycloalkyl substituent, the ring atom of the heterocycloalkyl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heterocycloalkyl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom.

The term "heterocycloalkyl" also includes substituents that are fused to a $C_6$-$C_{10}$ aromatic ring or to a 5- to 10-membered heteroaromatic ring, wherein a group having such a fused heterocycloalkyl group as a substituent is bound to a heteroatom of the heterocycloalkyl group or to a carbon atom of the heterocycloalkyl group. When such a fused heterocycloalkyl group is substituted with one or more substituents, the one or more substituents, unless otherwise specified, are each bound to a heteroatom of the heterocycloalkyl group or to a carbon atom of the heterocycloalkyl group. The fused $C_6$-$C_{10}$ aromatic ring or 5- to 10-membered heteroaromatic ring may be optionally substituted with halogen, $C_{1-6}$alkyl, $C_{3-10}$-cycloalkyl, $C_{1-6}$alkoxy, or =O.

The term "heteroaryl" refers to an aromatic ring structure containing from 5 to 14 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A heteroaryl may be a single ring or 2 or 3 fused rings. Examples of heteroaryl substituents include but are not limited to: 6-membered ring substituents such as pyridyl, pyrazyl, pyrimidinyl, and pyridazinyl; 5-membered ring substituents such as triazolyl, imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused ring substituents such as quinolinyl, isoquinolinyl, cinnolinyl, quinazolinyl, and 1,4-benzoxazinyl. In a group that has a heteroaryl substituent, the ring atom of the heteroaryl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heteroaryl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom. The term "heteroaryl" also includes pyridyl N-oxides and groups containing a pyridine N-oxide ring.

In some instances, the number of atoms in a cyclic substituent containing one or more heteroatoms (i.e., heteroaryl or heterocycloalkyl) is indicated by the prefix "X- to Y-membered", wherein X is the minimum and Y is the maximum number of atoms forming the cyclic moiety of the substituent. Thus, for example, 5- to 8-membered heterocycloalkyl refers to a heterocycloalkyl containing from 5 to 8 atoms, including one or more heteroatoms, in the cyclic moiety of the heterocycloalkyl.

Examples of single-ring heteroaryls and heterocycloalkyls include but are not limited to furanyl, dihydrofuranyl, tetrahydrofuranyl, thiophenyl (also known as "thiofuranyl"), dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, isoxazolinyl, thiazolyl, isothiazolyl, thiazolinyl, isothiazolinyl, thiazolidinyl, isothiazolidinyl, thiadiazolyl, oxathiazolyl, oxadiazolyl (including oxadiazolyl, 1,2,4-oxadiazolyl (also known as "azoximyl"), 1,2,5-oxadiazolyl (also known as "furazanyl"), or 1,3,4-oxadiazolyl), pyranyl (including 1,2-pyranyl or 1,4-pyranyl), dihydropyranyl, pyridinyl (also known as "azinyl"), piperidinyl, diazinyl (including pyridazinyl (also known as "1,2-diazinyl"), pyrimidinyl (also known as "1,3-diazinyl" or "pyrimidyl"), or pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl")), morpholinyl, azepinyl, oxepinyl, thiepinyl, and diazepinyl.

Examples of 2-fused-ring heteroaryls and heterocycloalkyls include but are not limited to indolizinyl, pyranopyrrolyl, 4H-quinolizinyl, purinyl, naphthyridinyl, pyridopyridinyl (including pyrido[3,4-b]pyridinyl, pyrido[3,2-b]pyridinyl, or pyrido[4,3-b]pyridinyl), and pteridinyl, indolyl, isoindolyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, and tetrahydroisoquinolinyl.

Examples of 3-fused-ring heteroaryls or heterocycloalkyls include but are not limited to 5,6-dihydro-4H-imidazo[4,5,1-ij]quinoline, 4,5-dihydroimidazo[4,5,1-hi]indole, 4,5,6,7-tetrahydroimidazo[4,5,1-jk][1]benzazepine, and dibenzofuranyl.

Other examples of fused-ring heteroaryls include but are not limited to benzo-fused heteroaryls such as indolyl, isoindolyl (also known as "isobenzazolyl" or "pseudoisoindolyl"), indoleninyl (also known as "pseudoindolyl"), isoindazolyl (also known as "benzpyrazolyl"), benzazinyl (including quinolinyl (also known as "1-benzazinyl") or isoquinolinyl (also known as "2-benzazinyl")), phthalazinyl, quinoxalinyl, quinazolinyl, benzodiazinyl (including cinnolinyl (also known as "1,2-benzodiazinyl") or quinazolinyl (also known as "1,3-benzodiazinyl")), benzopyranyl (including "chromanyl" or "isochromanyl"), benzothiopyranyl (also known as "thiochromanyl"), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl," "thionaphthenyl," or "benzothiofuranyl"), isobenzothienyl (also known as "isobenzothiophenyl," "isothionaphthenyl," or "isobenzothiofuranyl"), benzothiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, or 3,1,4-benzoxazinyl), benzisoxazinyl (including 1,2-benzisoxazinyl or 1,4-benzisoxazinyl), tetrahydroisoquinolinyl, carbazolyl, xanthenyl, and acridinyl.

The term "heteroaryl" also includes substituents such as pyridyl and quinolinyl that are fused to a $C_4$-$C_{10}$ carbocyclic ring, such as a $C_5$ or a $C_6$ carbocyclic ring, or to a 4- to 10-membered heterocyclic ring, wherein a group having such a fused heteroaryl group as a substituent is bound to an aromatic carbon of the heteroaryl group or to a heteroatom of the heteroaryl group. When such a fused heteroaryl group is substituted with one or more substituents, the one or more substituents, unless otherwise specified, are each bound to an aromatic carbon of the heteroaryl group or to a heteroatom of the heteroaryl group. The fused $C_4$-$C_{10}$ carbocyclic or 4- to 10-membered heterocyclic ring may be optionally substituted with halogen, $C_{1-6}$alkyl, $C_{3-10}$cycloalkyl, or =O.

Additional examples of heteroaryls and heterocycloalkyls include but are not limited to: 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzo[1,3]dioxine, benzo[1,4]dioxine, benzopyrrolidinyl, benzopiperidinyl, benzoxolanyl, benzothiolanyl, 4,5,6,7-tetrahydropyrazol[1,5-a]pyridine, benzothianyl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-2-yl (C-attached).

A substituent is "substitutable" if it comprises at least one carbon or nitrogen atom that is bonded to one or more hydrogen atoms. Thus, for example, hydrogen, halogen, and cyano do not fall within this definition.

If a substituent is described as being "substituted," a non-hydrogen substituent is in the place of a hydrogen substituent on a carbon or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent. One exemplary substituent may be depicted as —NR'R", wherein R' and R" together with the nitrogen atom to which they are attached may form a heterocyclic ring comprising 1 or 2 heteroatoms independently selected from oxygen, nitrogen, or sulfur, wherein said heterocycloalkyl moiety may be optionally substituted. The heterocyclic ring formed from R' and R" together with the nitrogen atom to which they are attached may be partially or fully saturated, or aromatic. In one embodiment, the heterocyclic ring consists of 4 to 10 atoms. In another embodiment, the heterocyclic ring is selected from the group consisting of piperidinyl, morpholinyl, azetidinyl, pyrrolyl, imidazolyl, pyrazolyl, triazolyl and tetrazolyl.

This specification uses the terms "substituent," "radical," and "group" interchangeably.

If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. To illustrate, tetrazolyl (which has only one substitutable position) would be optionally substituted with up to one non-hydrogen substituent. To illustrate further, if an amino nitrogen is described as being optionally substituted with up to 2 non-hydrogen substituents, then the nitrogen will be optionally substituted with up to 2 non-hydrogen substituents if the amino nitrogen is a primary nitrogen, whereas the amino nitrogen will be optionally substituted with up to only 1 non-hydrogen substituent if the amino nitrogen is a secondary nitrogen.

A prefix attached to a multi-moiety substituent only applies to the first moiety. To illustrate, the term "alkylcycloalkyl" contains two moieties: alkyl and cycloalkyl. Thus, a $C_{1-6}$— prefix on $C_{1-6}$alkylcycloalkyl means that the alkyl moiety of the alkylcycloalkyl contains from 1 to 6 carbon atoms; the $C_{1-6}$— prefix does not describe the cycloalkyl moiety. To illustrate further, the prefix "halo" on haloalkoxyalkyl indicates that only the alkoxy moiety of the alkoxyalkyl substituent is substituted with one or more halogen substituents. If the halogen substitution only occurs on the alkyl moiety, the substituent would be described as "alkoxyhaloalkyl." If the halogen substitution occurs on both the alkyl moiety and the alkoxy moiety, the substituent would be described as "haloalkoxyhaloalkyl."

If substituents are described as being "independently selected" from a group, each substituent is selected independent of the other(s). Each substituent therefore may be identical to or different from the other substituent(s).

It is understood that descriptions of any one substituent, such as $R^1$, may be combined with descriptions of any other substituents, such as $R^2$, such that each and every combination of the first substituent and the second substituent is provided herein the same as if each combination were specifically and individually listed. For example, in one variation, $R^1$ is taken together with $R^2$ to provide an embodiment wherein $R^1$ is methyl and $R^2$ is halogen.

As used herein the term "Formula I" may be hereinafter referred to as a "compound(s) of the invention." Such terms are also defined to include all forms of the compound of Formula I, including hydrates, solvates, isomers, crystalline and non-crystalline forms, isomorphs, polymorphs, and metabolites thereof. For example, the compounds of Formula I, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of Formula I may exist as clathrates or other complexes. Included within the scope of the invention are complexes such as clathrates, drug-host inclusion complexes wherein, in contrast to the aforementioned solvates, the drug and host are present in stoichiometric or non-stoichiometric amounts. Also included are complexes of Formula I containing two or more organic and/or inorganic components which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of Formula I may have asymmetric carbon atoms. The carbon-carbon bonds of the compounds of Formula I may be depicted herein using a solid line (—), a solid wedge (⬛) or a dotted wedge (⸽⸽⸽). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of Formula I, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The present invention also includes isotopically-labeled compounds, which are identical to those recited in Formula I above, but for the fact that one or more atoms are replaced by an atom having an atomic mass or mass number different from the atomic mass or mass number usually found in nature. Examples of isotopes that may be incorporated into compounds of Formula I include isotopes of hydrogen, carbon, nitrogen, oxygen, phosphorus, fluorine and chlorine, such as, but not limited to, $^2$H, $^3$H, $^{13}$C, $^{14}$C, $^{15}$N, $^{18}$O, $^{17}$O, $^{32}$P, $^{35}$S, $^{18}$F, and $^{36}$Cl. Certain isotopically-labeled compounds of Formula I, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labeled compounds of Formula I may generally be prepared by carrying out the procedures disclosed in the Schemes and/or in the Examples and Preparations below, by substituting an isotopically-labeled reagent for a non-isotopically-labeled reagent.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalenesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (i.e., dimethyl, diethyl, dibutyl, and diamyl sulfates), long chain halides (i.e., decyl, lauryl, myristyl, and stearyl chlorides, bromides, and iodides), arylalkyl halides (i.e., benzyl and phenethyl bromides), and others.

In one embodiment, hemisalts of acids and bases may also be formed, for example, hemisulphate and hemicalcium salts.

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts. The term "therapeutically effective amount" as used herein refers to that amount of the compound being administered which will relieve to some extent one or more of the symptoms of the disorder being treated.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

DETAILED DESCRIPTION OF THE INVENTION

The compounds of the invention may be administered orally. Oral administration may involve swallowing, so that the compound enters the gastrointestinal tract, or buccal or sublingual administration may be employed by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compounds of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be Formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled-release Formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (i.e., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (i.e., sterile injectable aqueous or oleaginous suspensions) may be Formulated according to the known art using suitable dispersing, wetting, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical Formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical Formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, Finnin and Morgan, J. Pharm. Sci., 88 (10), 955-958 (1999).

Formulations suitable for topical administration to the eye include, for example, eye drops wherein the compound of this invention is dissolved or suspended in a suitable carrier. A typical Formulation suitable for ocular or aural administration may be in the form of drops of a micronised suspension or solution in isotonic, pH-adjusted, sterile saline. Other Formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed-linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such Formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone; as a mixture, for example, in a dry blend with lactose; or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective Formulation and administration procedures. The above considerations in regard to effective Formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be administered simultaneously (either in the same dosage form or in separate dosage forms) or sequentially. An exemplary therapeutic agent may be, for example, a metabotropic glutamate receptor agonist.

The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

In another embodiment, the invention relates to the novel intermediates useful for preparing the compounds of the invention. For example, the compound of Formula II is useful for preparing the compounds of the invention.

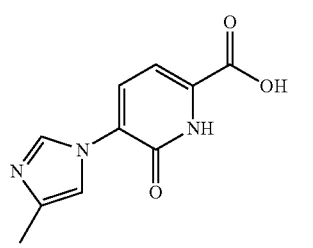

II

The compounds of Formula II may exhibit the phenomenon of tautomerism. For example, the compounds of Formula II may exist in several tautomeric forms, including the pyridone form, IIa, and the hydroxypyridine form, IIb. All such tautomeric forms are included within the scope of compounds of Formula II. Tautomers exist as mixtures of a tautomeric set in solution. In solid form, usually one tautomer predominates. Even though one tautomer may be described, the present invention includes all tautomers of the compounds of Formula II and salts thereof. Examples of tautomers are described by the compounds of Formula IIa and IIb.

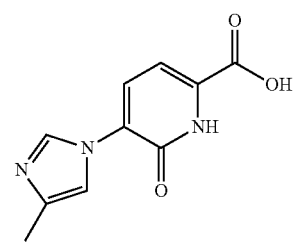

IIa

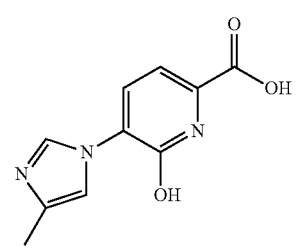

IIb

Examples of the salt forms of the tautomers are described by the compounds of Formula IIai, IIaii, IIbi,

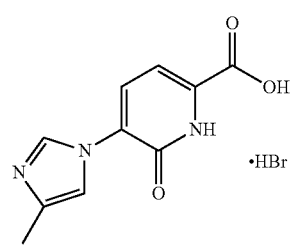

IIai

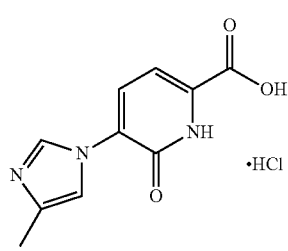

IIaii

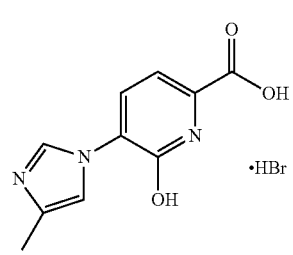

IIbi

IIbii
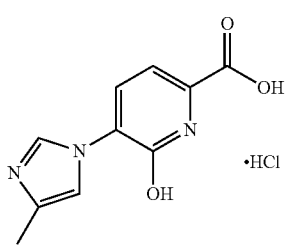

IIb
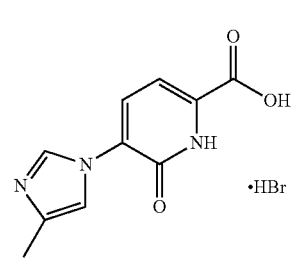

When intermediates used to synthesize compounds of the present invention incorporate a basic center their suitable acid addition salts may be employed in synthetic pathways. Such suitable addition salts include but are not limited to those derived from inorganic acids, such as hydrochloric, hydrobromic, hydrofluoric, hydroiodic, boric, fluoroboric, phosphoric, nitric, carbonic, and sulfuric acids, and organic acids such as acetic, benzenesulfonic, benzoic, ethanesulfonic, fumaric, lactic, maleic, methanesulfonic, trifluoromethanesulfonic, succinic, toluenesulfonic, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, lactate, maleate, fumarate, benzoate, p-hydroxybenzoate, phenylacetate, mandelate, methanesulfonate, ethanesulfonate, benzenesulfonate, toluenesulfonate, adipate, butyrate, camphorate, cyclopentanepropionate, dodecylsulfate, heptanoate, hexanoate, nicotinate, 2-naphthalesulfonate, oxalate, 3-phenylpropionate, pivalate, and undecanoate.

Furthermore, where intermediates used to prepare compounds of the invention carry an acidic moiety, suitable salts thereof may be employed for synthesis. Such salts include alkali metal salts, i.e., lithium, sodium or potassium salts; alkaline earth metal salts, e.g., calcium or magnesium salts; and salts formed with suitable organic ligands such as amines or quaternary ammonium cations. Organic salts of such acidic intermediates may be made from primary, secondary or tertiary amines such as methylamine, diethylamine, ethylenediamine or trimethylamine. Quaternary amines may be prepared by reaction of tertiary amines with agents such as lower alkyl ($C_1$-$C_6$) halides (e.g., methyl, ethyl, propyl, and butyl chlorides, bromides, and iodides), dialkyl sulfates (i.e., dimethyl, diethyl, dibutyl, and diamyl sulfates), arylalkyl halides (i.e., benzyl and phenethyl bromides), and others.

Examples of such compound Formula II intermediate salt forms are depicted below:

IIa
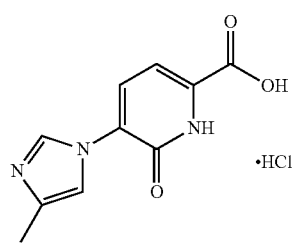

The compounds of Formulas I and II may be prepared by the methods described below, together with synthetic methods known in the art of organic chemistry, or modifications and derivatizations that are familiar to those of ordinary skill in the art. The starting materials used herein are commercially available or may be prepared by routine methods known in the art (such as those methods disclosed in standard reference books such as the COMPENDIUM OF ORGANIC SYNTHETIC METHODS, Vol. I-XII (published by Wiley-Interscience)). Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

Scheme 1

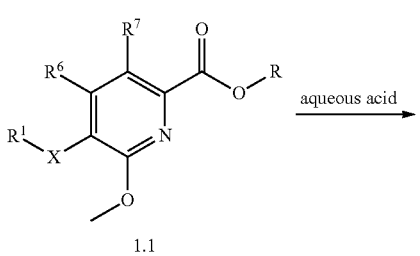

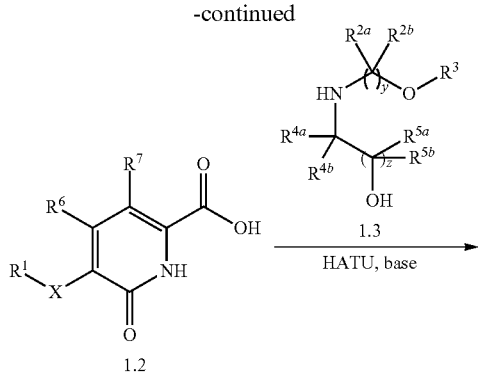

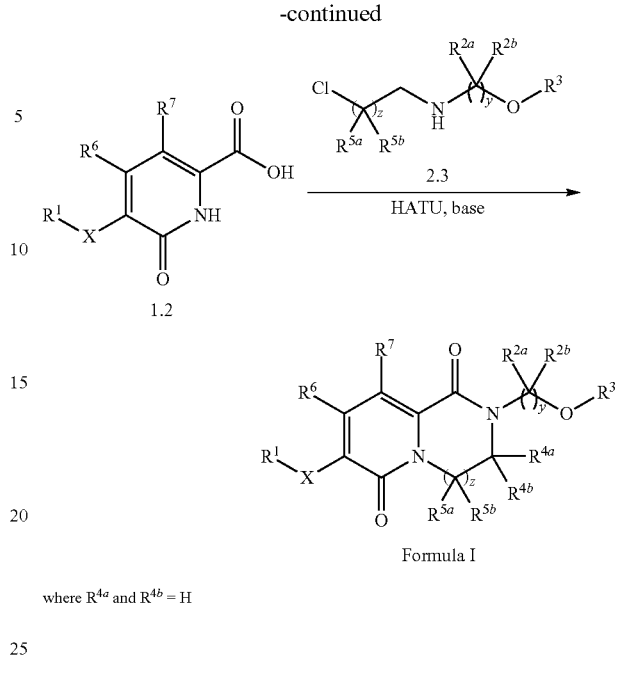

where $R^{4a}$ and $R^{4b}$ = H

Scheme 2 illustrates a method for the preparation of compounds of Formula I. This method commences with the reductive amination of chloroaledehyde (2.1) and an amine of Formula 2.2 using one of many reductive amination protocols known to those skilled in the art. For example, this reaction may be carried out by using a reducing agent such as sodium triacetoxyborohydride in a suitable solvent such as methanol. Following purification, the resultant chloroethylamine 2.3 may be isolated and stored as its HCl salt. The final compound of Formula I may then be prepared by treating a mixture of chloroalkylamine 2.3, acid 1.2, and a base such as diisopropylethylamine with a suitable amide coupling reagent such as BOP-Cl [(bis(2-oxo-3-oxazolidinyl)phosphonic chloride], T3P [propylphosphonic anhydride] or HATU (preferably HATU) in a solvent such as dichloromethane.

Scheme 1 illustrates a method for preparing compounds of Formula I. A compound of Formula 1.1 is heated in the presence of an aqueous acid such as hydrochloric acid to furnish the corresponding pyridinone acid of Formula 1.2. The intermediate of Formula 1.2 is subjected to an amide coupling and in situ cyclization reaction with amino alcohol of Formula 1.3 using a coupling reagent such as HATU [O-(7-azabenzotriazol-1-yl)-N,N,N',N'-tetramethyluronium hexafluorophosphate]. The reaction is carried out in the presence of a suitable base such as diisopropylethyl amine and in a solvent such as dichloromethane, or dimethylformamide.

Scheme 2

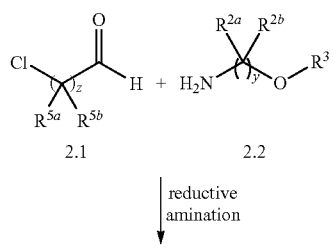

Scheme 3

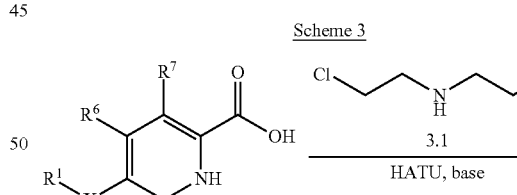

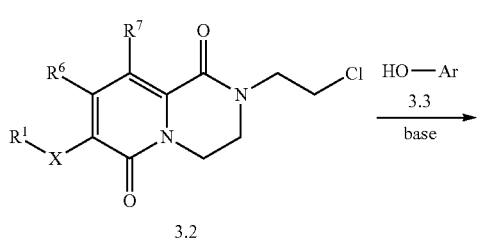

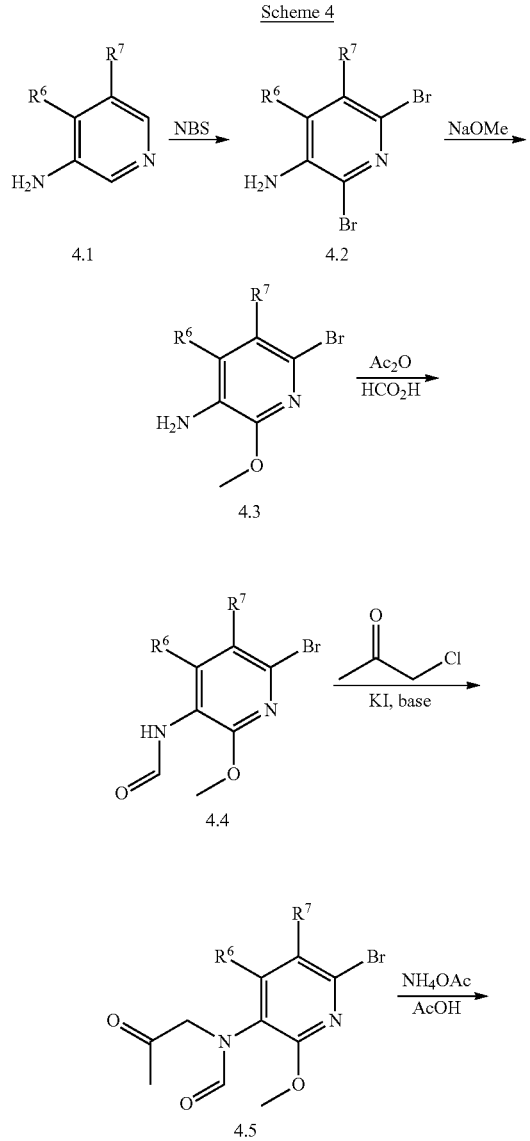

Scheme 3 illustrates a method for the preparation of compounds of Formula 3.4. An acid of Formula 1.2 is treated with bis(2-chloroethyl)amine (3.1), a base such as $K_2CO_3$, and an amide coupling reagent such as HATU in a suitable solvent such as DMF. The resulting intermediate of Formula 3.2 is then coupled to a compound of Formula 3.3 by heating in the presence of a suitable base such as $K_2CO_3$ in a solvent such as DMF or DMSO to afford the final compound of Formula 3.4.

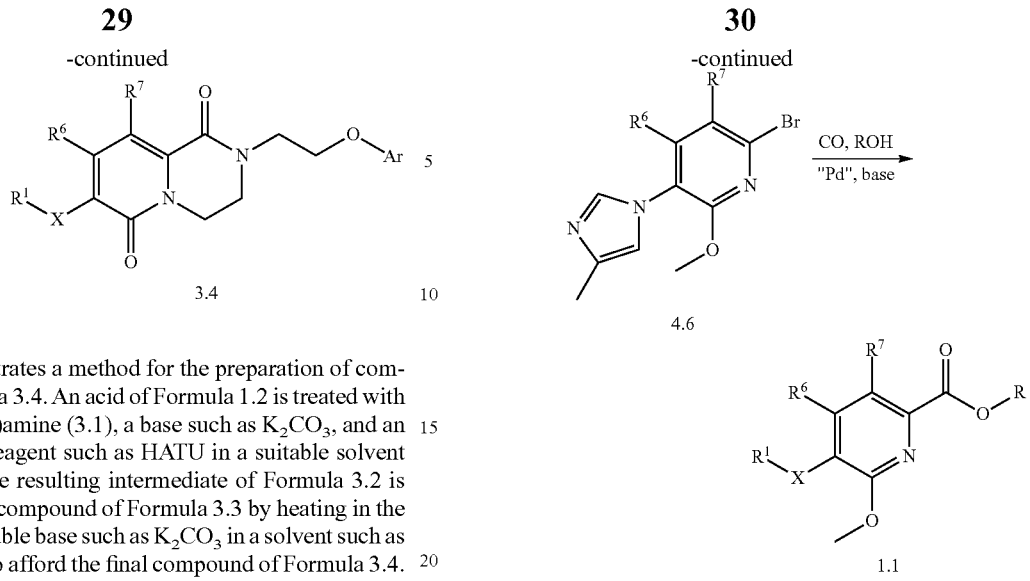

where $R^1$—X = 4-methylimidazole

Scheme 4 illustrates a method for the preparation of compounds of Formula 1.1 where $R^1$—X=4-methylimidazole. A 3-aminopyridine compound of Formula 4.1 is brominated using N-bromosuccinamide in a solvent such as a mixture of DMSO and water. The resulting intermediate of Formula 4.2 is then heated with sodium methoxide in a suitable solvent such as 1,4-dioxane to afford a compound of Formula 4.3. The intermediate of Formula 4.3 is then treated with a mixture of acetic anhydride and formic acid to afford a formamide of Formula 4.4, which is alkylated with chloroacetone in the presence of potassium iodide and a base such as $Cs_2CO_3$ in a suitable solvent such as DMF. The resulting intermediate of Formula 4.5 is then heated in the presence of $NH_4OAc$ in acetic acid to furnish the imidazole derivative 4.6. Finally, the compound of Formula 1.1 can be prepared by subjecting the intermediate of Formula 4.6 to a carbonylation reaction. This transformation may be carried out by heating a solution of 4.6 and a base such as triethylamine in a suitable alcohol solvent such as methanol under an atmosphere of CO in the presence of a suitable palladium catalyst such as $Pd(dppf)_2Cl_2 \cdot DCM$ [1,1'-bis(diphenylphosphino)ferrocene-palladium(II) dichloride dichloromethane complex].

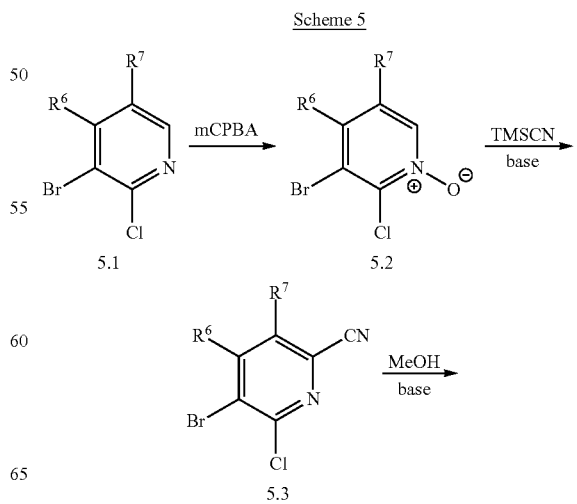

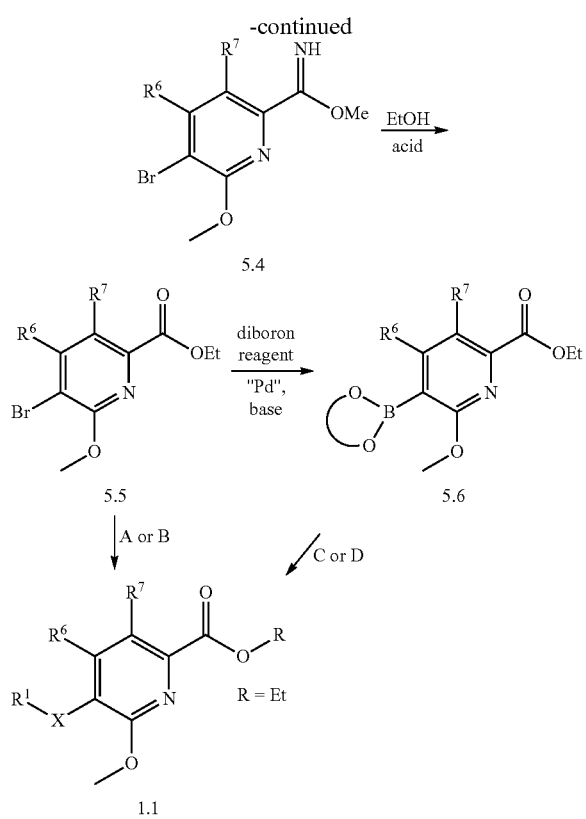

Scheme 5 depicts a method for the preparation of compounds of Formula 1.1. A pyridyl derivative of Formula 5.1 is oxidized with an oxidizing agent such as mCPBA [meta-chloroperbenzoic acid] in a suitable solvent such as dichloroethane to afford the corresponding N-oxide of Formula 5.2. The intermediate of Formula 5.2 is then heated in the presence of TMSCN [trimethylsilyl cyanide] and a base such as triethylamine in a solvent such as acetonitrile to afford the intermediate of Formula 5.3. The ethyl ester of Formula 5.5 may then be prepared from 5.3 in two steps by subjecting 5.3 to sodium methoxide in a solvent such as THF followed by treatment with EtOH and an acid such as HCl. The ester of Formula 5.5 is a versatile intermediate that allows introduction of a variety of heterocycles X. For example, 5.5 may be subjected to a Suzuki coupling with a heteroaryl boronic acid using methods well known to those skilled in the art [see Tetrahedron 2002, 58, 9633-9695]. Alternatively, the compound of Formula 5.5 may be coupled to a heterocycle $R^1X$ using a direct arylation approach [see J. Org. Chem. 2011, DOI: 10.1021/jo102081a, and references therein]. For example, 5.5 may be coupled to 2-methyl-1,3-oxazole [Formula 5.7 where $R^1$=Me] by heating in the presence of a suitable palladium-catalyst such as allylpalladium chloride dimer and a base such as $K_2CO_3$ in a solvent such as 1,4-dioxane to afford the intermediate of Formula 1.1 where X=oxazole and $R^1$=Me.

Alternatively, the compound of Formula 5.5 may be converted to the corresponding boronate 5.6, using a palladium catalyzed cross coupling with a diboron reagent such as 5,5,5',5'-tetramethyl-2,2'-bi-1,3,2-dioxaborinane in the presence of potassium acetate and a palladium catalyst such as $Pd(dppf)_2Cl_2$.DCM in a solvent such as 1,4-dioxane. The resulting boronate intermediate of Formula 5.6 can in turn be subjected to a Suzuki coupling with a heteroaryl halide to afford the final compound of Formula 1.1. Another method for the introduction of a heterocycle X involves the use of a Chan-Lam coupling [see Tetrahedron Lett. 2003, 44, 3863-3865, and Synthesis, 2008, 5, 795-799]. For example, 5.6 may be coupled to substituted imidazole 5.8 by heating with copper oxide in a solvent such as methanol in the presence of air to afford the intermediate of Formula 1.1 where X=imidazole.

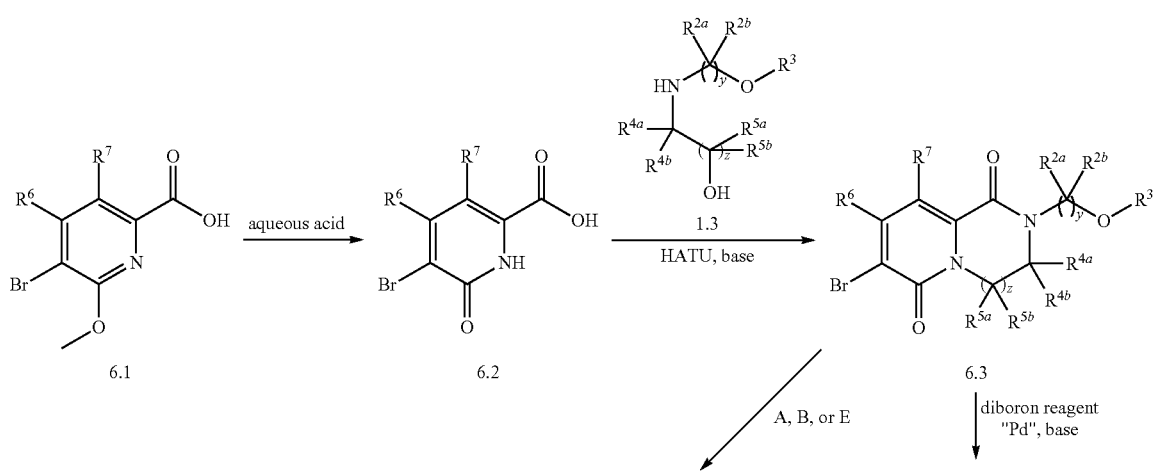

-continued

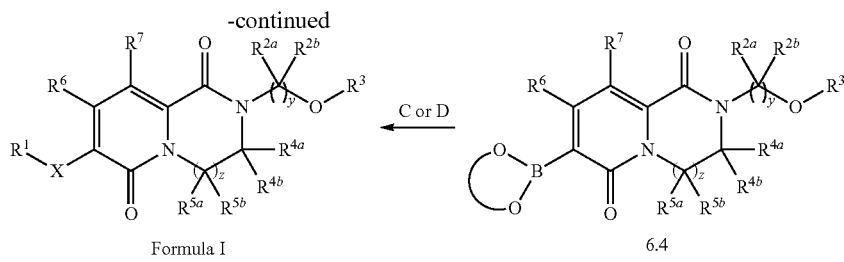

Formula I

A) Suzuki coupling: R¹X—B(OH)₂, "Pd", base

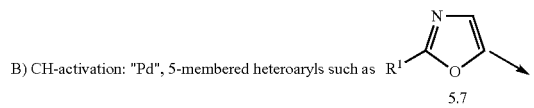

B) CH-activation: "Pd", 5-membered heteroaryls such as R¹

5.7

C) Chan-Lam coupling:
CuO₂ or Cu(OAc)₂, 5-membered heteroaryls such as

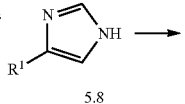

5.8

D) Suzuki coupling: R¹X—Br, "Pd", base

E) Base and a heteroaryl such as R¹

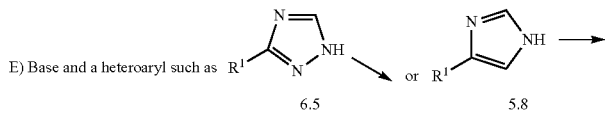

6.5      5.8 where X = 6-membered heteroaryl ring or a 5-membered heteroaryl ring

Scheme 6 illustrates a method for the synthesis of compounds of Formula I. The method commences by heating the compound of Formula 6.1 in an acid such as hydrochloric acid to afford pyridinone acid intermediate 6.2. The acid of Formula 6.2 may be subjected to a coupling/cyclization reaction with an aminoalcohol of Formula 1.3 to afford an intermediate of Formula 6.3 using chemistry described in Scheme 1. The final compound, Formula I, may then be formed directly from 6.3 or via boronate 6.4 using the strategies discussed in detail for Scheme 5. Alternatively, compounds of Formula I where heterocycle X is linked to the pyridinone ring via a C—N bond may be formed by nucleophilic aromatic substitution. For example, triazole 6.5 may be coupled to 6.3 by heating in the presence of a base such as K₂CO₃ and a solvent such as DMSO to afford the final compound of Formula I where X=triazole.

Scheme 7

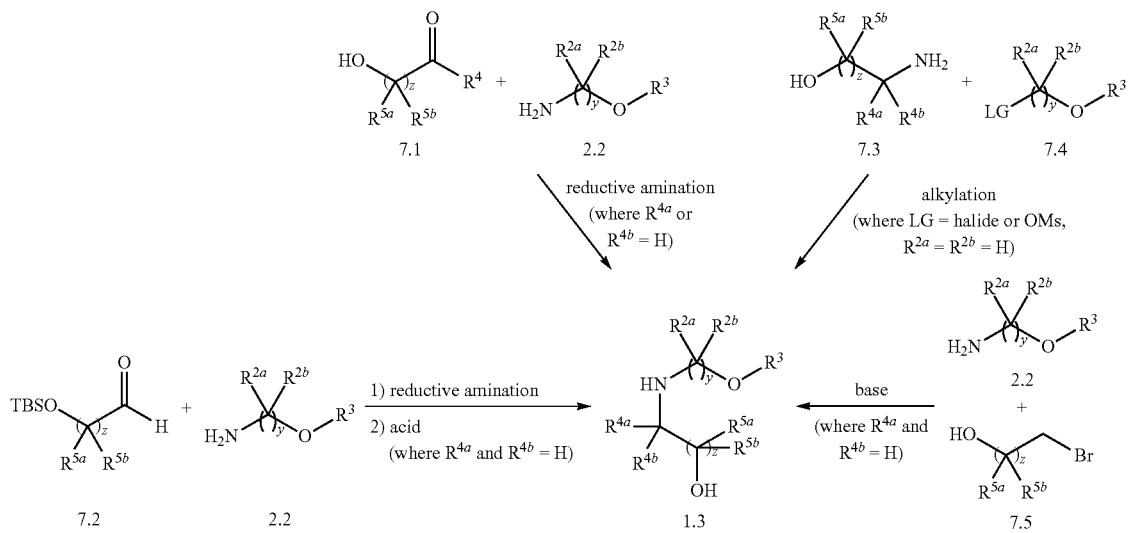

The aminoalcohol coupling partner of Formula 1.3 may be prepared via a wide variety of synthetic methods, which can readily be envisioned and developed by one skilled in the art. These include, but are not limited to, those methods illustrated in Scheme 7. For example, the aminoalcohol of Formula 1.3 may be prepared by carrying out a reductive amination of a ketone of Formula 7.1 with an amine of Formula 2.2 using one of many procedures well-known to those skilled in the art. Another method involves reductive amination of an aldehyde of Formula 7.2 with an amine of Formula 2.2 followed by removal of the TBS protecting group by using a suitable procedure including treatment with methanolic HCl or tetrabutylammonium fluoride. Another example of a representative method for the synthesis of an aminoalcohol of Formula 1.3 involves alkylation of amine 7.3 with a halide or mesylate of Formula 7.4. Yet another method involves alkylation of an amine of Formula 2.2 with 2-bromoalcohol 7.5.

Experimental Procedures and Working Examples

The following illustrate the synthesis of various compounds of the present invention. Additional compounds within the scope of this invention may be prepared using the methods illustrated in these Examples, either alone or in combination with techniques generally known in the art.

It will be understood that the intermediate compounds of the invention depicted above are not limited to the particular enantiomer shown, but also include all stereoisomers and mixtures thereof. It will also be understood that compounds of Formula I can include intermediates of compounds of Formula I.

Experimental Procedures

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples or Methods, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluants/gradients were chosen to provide appropriate $R_f$s or retention times.

PREPARATIONS

Preparation 1

5-(4-Methyl-1H-imidazol-1-yl)-6-oxo-1,6-dihydro-pyridine-2-carboxylic acid, hydrobromide salt (P1)

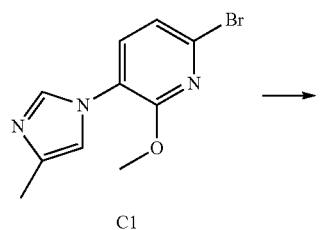

C1

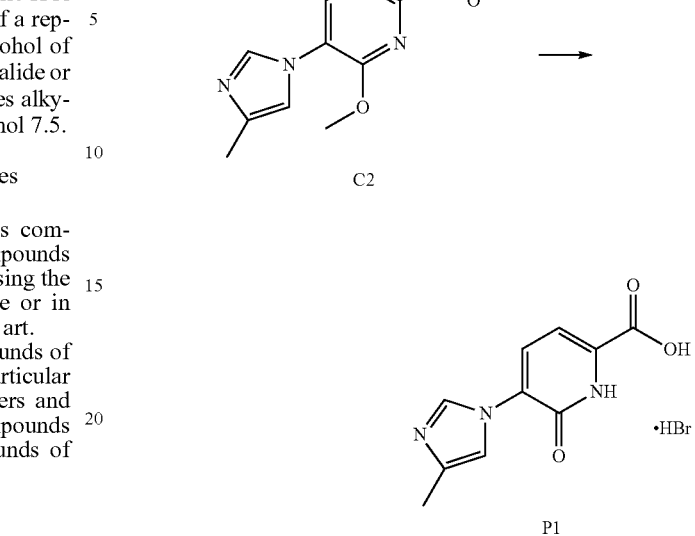

Step 1. Synthesis of methyl 6-methoxy-5-(4-methyl-1H-imidazol-1-yl)pyridine-2-carboxylate (C2). To a solution of the known 6-bromo-2-methoxy-3-(4-methyl-1H-imidazol-1-yl)pyridine (C1, T. Kimura et al., U.S. Pat. Appl. Publ. (2009), US 20090062529 A1) (44.2 g, 165 mmol) in methanol (165 mL) was added triethylamine (46 mL, 330 mmol) and [1,1'-bis(diphenylphosphino)ferrocene]dichloropalladium(II), dichloromethane complex (6.7 g, 8.24 mmol). The mixture was degassed several times with nitrogen. The reaction was heated to 70° C. under CO atmosphere (3 bar) in a Parr apparatus. After 30 minutes, the pressure dropped to 0.5 bar; additional CO was added until the pressure stayed constant for a period of 30 minutes. The mixture was allowed to cool to room temperature and filtered through a pad of Celite. The Celite pad was washed twice with methanol and the combined filtrates were concentrated under reduced pressure. The residue (88 g) was dissolved in ethyl acetate (1 L) and water (700 mL), and the layers were separated. The organic layer was washed with water (200 mL), and the aqueous layer was extracted with ethyl acetate (500 mL). The combined organic layers were dried over magnesium sulfate, filtered and concentrated to provide the title compound. Yield: 42.6 g, 175 mmol, quantitative.

Step 2. Synthesis of 5-(4-methyl-1H-imidazol-1-yl)-6-oxo-1,6-dihydropyridine-2-carboxylic acid, hydrobromide salt (P1) A solution of methyl 6-methoxy-5-(4-methyl-1H-imidazol-1-yl)pyridine-2-carboxylate (C2) (3.82 g, 15.9 mmol) in acetic acid (30 mL) and aqueous hydrobromic acid (48%, 30 mL) was heated at reflux for 4 hours. The reaction was allowed to cool to room temperature, then chilled in an ice bath; the resulting precipitate was collected via filtration and washed with ice water (30 mL). Recrystallization from ethanol (20 mL) provided the title compound as a light yellow solid. Yield: 3.79 g, 12.6 mmol, 79%. LCMS m/z 220.1 (M+1). $^1$H-NMR (400 MHz, DMSO-$d_6$) δ 2.34 (br s, 3H), 7.09 (d, J=7.4 Hz, 1H), 7.88-7.91 (m, 1H), 8.07 (d, J=7.6 Hz, 1H), 9.58-9.60 (m, 1H), 12.6 (v br s, 1H).

Preparation 2

2-(2-Chloroethyl)-7-(4-methyl-1H-imidazol-1-yl)-3,4-dihydro-2H-pyrido[1,2-a]pyrazine-1,6-dione (P2)

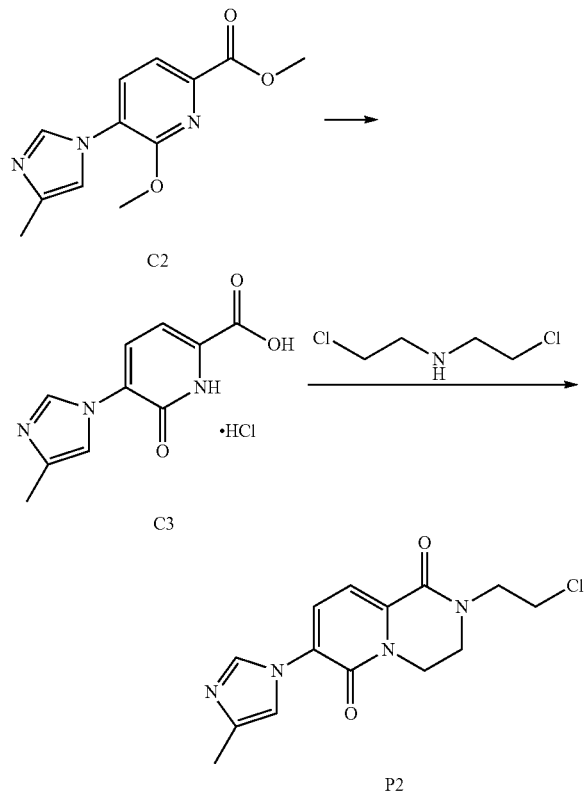

Step 1. Synthesis of 5-(4-methyl-1H-imidazol-1-yl)-6-oxo-1,6-dihydropyridine-2-carboxylic acid, hydrochloride salt (C3). A solution of 6-methoxy-5-(4-methyl-1H-imidazol-1-yl)pyridine-2-carboxylate (C2) (34.3 g, 139 mmol) in aqueous hydrochloric acid (37%, 230 mL) and 1,4-dioxane (230 mL) was heated at reflux for 18 hours. After cooling to room temperature, the reaction was filtered and the solids were washed with 1,4-dioxane (2×100 mL). The solids were mixed with methanol (500 mL) and the volatiles were removed in vacuo. The residue was stirred with methanol (100 mL) for 15 minutes, and 1,4-dioxane (250 mL) was added. The resulting mixture was stirred for 15 minutes; the solids were collected by filtration and washed with 1,4-dioxane to provide the title compound as a beige solid. Yield: 35.4 g, 138 mmol, 99%. $^1$H NMR (300 MHz, DMSO-$d_6$) δ 2.33 (d, J=0.9 Hz, 3H), 7.09 (d, J=7.5 Hz, 1H), 7.84-7.87 (m, 1H), 8.04 (d, J=7.5 Hz, 1H), 9.50 (d, J=1.6 Hz, 1H).

Step 2. Synthesis of 242-chloroethyl)-7-(4-methyl-1H-imidazol-1-yl)-3,4-dihydro-2H-pyrido[1,2-a]pyrazine-1,6-dione (P2). Potassium carbonate (195.4 g, 1414 mmol) was added to a mixture of 5-(4-methyl-1H-imidazol-1-yl)-6-oxo-1,6-dihydropyridine-2-carboxylic acid, hydrochloride (C3) (34.5 g, 135 mmol) and 2-chloro-N-(2-chloroethyl)ethanamine hydrochloride (37.8 g, 212 mmol) in N,N-dimethylformamide (670 mL), and the reaction was stirred for 10 minutes. O-(7-Azabenzotriazol-1-yl)-N,N,N',N'-tetramethyluronium hexafluorophosphate (HATU, 83.5 g, 219 mmol) was added and stirring was continued for an additional 3 hours and 40 minutes. The reaction mixture was then poured into water (4 L) and stirred for 30 minutes. After extraction with dichloromethane (3×1 L), the combined organic layers were washed with saturated aqueous sodium chloride solution (3×3 L), dried over magnesium sulfate, filtered and concentrated in vacuo. Finally, most of the DMF was removed by using a methanol/liquid nitrogen cooler. The residue was stirred in ethyl acetate (approximately 50 mL) for 30 minutes. The solids were collected by filtration and washed with ethyl acetate and pentane, providing the title compound as a yellow solid. Yield: 23.0 g, 75.0 mmol, 56%. LCMS m/z 307.1 (M+1). $^1$H-NMR (300 MHz, CDCl$_3$) δ 2.29 (br s, 3H), 3.80-3.93 (m, 6H), 4.38-4.44 (m, 2H), 7.13-7.16 (m, 1H), 7.27 (d, J=7.6 Hz, 1H), 7.45 (d, J=7.6 Hz, 1H), 8.24 (d, J=1.0 Hz, 1H).

Preparation 3

2-[(2-{2-[2-(Trifluoromethyl)-1,3-thiazol-4-yl]phenoxy}ethyl)amino]ethanol (P3)

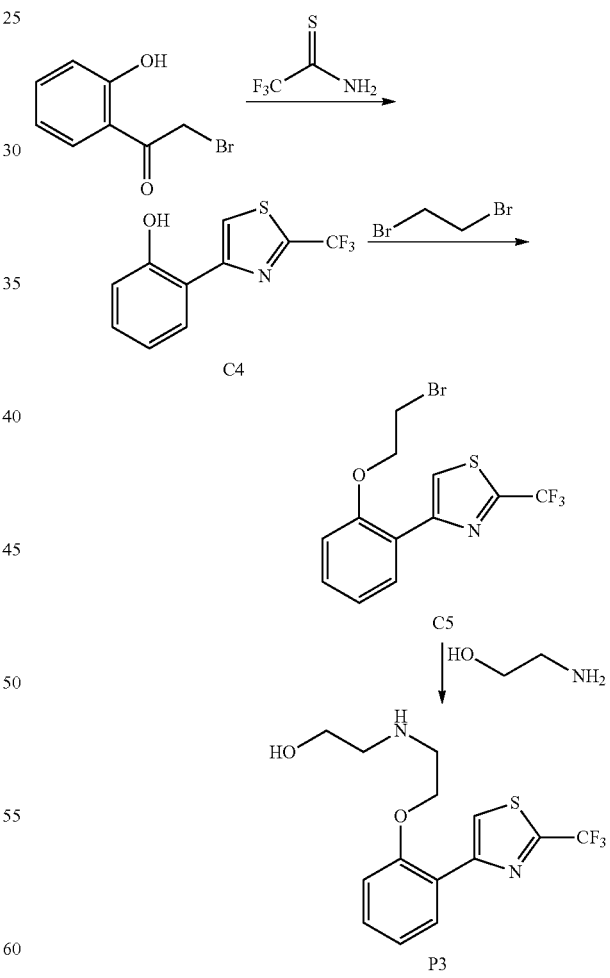

Step 1. Synthesis of 2-[2-(trifluoromethyl)-1,3-thiazol-4-yl]phenol (C4) 2,2,2-Trifluoroethanethioamide (which may be prepared by the method of J. H. Hillhouse et al., *Phosphorus, Sulfur Relat. Elem.* 1986, 26, 169-84) (157 mg, 1.22 mmol) in ethanol (1.3 mL) was added drop-wise to a solution of 2-bromo-1-(2-hydroxyphenyl)ethanone (119 mg, 0.55 mmol) in ethanol (1.3 mL) and the reaction was refluxed overnight. The reaction was concentrated in vacuo and purified via silica gel chromatography (Gradient: 5% to 20% ethyl acetate in heptane) to afford the title compound. Yield: 67 mg, 0.27 mmol, 49%. LCMS m/z 246.0 (M+1). $^1$H NMR (400 MHz, CDCl$_3$) δ 6.95 (ddd, J=8, 7, 1 Hz, 1H), 7.07 (dd, J=8.2, 1.2 Hz, 1H), 7.33 (ddd, J=8, 7, 2 Hz, 1H), 7.64 (dd, J=7.8, 1.6 Hz, 1H), 7.81 (s, 1H), 10.47 (s, 1H).

Step 2. Synthesis of 4-[2-(2-bromoethoxy)phenyl]-2-(trifluoromethyl)-1,3-thiazole (C5) Cesium carbonate (266 mg, 0.816 mmol) was added to a solution of 2-[2-(trifluoromethyl)-1,3-thiazol-4-yl]phenol (C4) (100 mg, 0.408 mmol) and 1,2-dibromoethane (0.35 mL, 4.1 mmol) in acetonitrile (33 mL), and the mixture was heated at 70° C. for 18 hours. After cooling to room temperature, the reaction was partitioned between dichloromethane and water; the organic layer was dried over magnesium sulfate, filtered, and concentrated in vacuo. Purification via silica gel chromatography (Gradient: 10% to 30% ethyl acetate in heptane) afforded the title compound. Yield: 115 mg, 0.327 mmol, 80%. $^1$H NMR (400 MHz, CDCl$_3$) δ 3.78 (br dd, J=5.5, 5.5 Hz, 2H), 4.48 (dd, J=5.7, 5.5 Hz, 2H), 6.97 (br d, J=8.4 Hz, 1H), 7.13 (ddd, J=7.7, 7.4, 1.1 Hz, 1H), 7.35 (ddd, J=8.3, 7.3, 1.8 Hz, 1H), 8.31 (dd, J=7.8, 1.8 Hz, 1H), 8.37 (s, 1H).

Step 3. Synthesis of 2-[(2-{2-[2-(trifluoromethyl)-1,3-thiazol-4-yl]phenoxy}ethyl)amino]ethanol (P3). A mixture of 4-[2-(2-bromoethoxy)phenyl]-2-(trifluoromethyl)-1,3-thiazole (C5) (115 mg, 0.327 mmol) and 2-aminoethanol (0.197 mL, 3.26 mmol) was heated to 80° C. for 3 hours. After cooling to room temperature, the reaction was diluted with dichloromethane and washed with 0.5 N aqueous sodium hydroxide solution, then with water. The organic layer was dried over magnesium sulfate, filtered, and concentrated in vacuo, yielding the title compound as a white solid. Yield: 113 mg, quantitative. $^1$H NMR (400 MHz, CDCl$_3$) δ 2.88 (dd, J=5.2, 5.1 Hz, 2H), 3.15 (dd, J=5, 5 Hz, 2H), 3.68 (br dd, J=5, 5 Hz, 2H), 4.25 (dd, J=5, 5 Hz, 2H), 7.03 (br d, J=8.3 Hz, 1H), 7.08-7.12 (m, 1H), 7.33-7.38 (m, 1H), 8.18 (s, 1H), 8.21 (br d, J=7.9 Hz, 1H).

Preparation 4

2-({(2S)-1-[4-Fluoro-2-(trifluoromethyl)phenoxy]propan-2-yl}amino)ethanol, hydrochloride salt (P4)

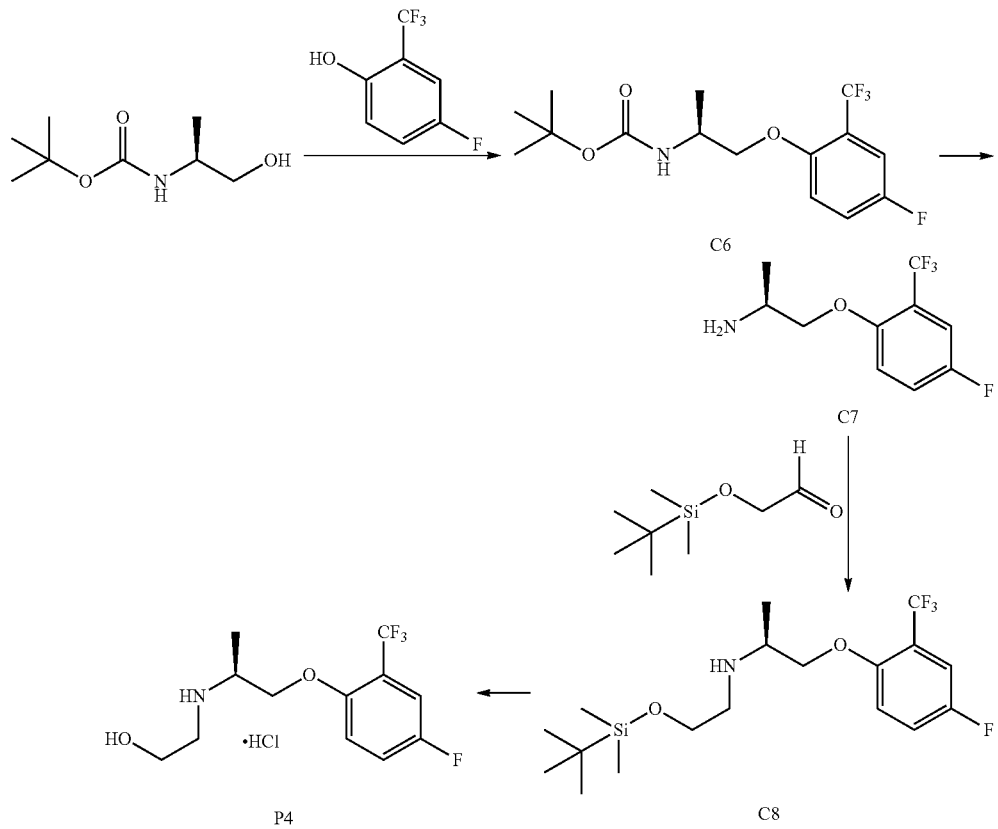

Step 1. Synthesis of tert-butyl{(2S)-1-[4-fluoro-2-(trifluoromethyl)phenoxy]propan-2-yl}carbamate (C6). To a mixture of tert-butyl[(2S)-1-hydroxypropan-2-yl]carbamate (1.07 g, 6.11 mmol), 4-fluoro-2-(trifluoromethyl)phenol (1.10 g, 5.55 mmol) and triphenylphosphine-resin (2.80 g, 8.40 mmol) in tetrahydrofuran (50 mL) was added drop-wise diisopropyl azodicarboxylate (DIAD, 1.37 g, 6.66 mmol). The reaction was allowed to stir at room temperature for 3 days, then filtered and rinsed with ethyl acetate. The combined filtrate was washed with 0.5 N aqueous sodium hydroxide and saturated aqueous sodium chloride solution, dried over magnesium sulfate, filtered and concentrated in vacuo. Purification via silica gel chromatography (50% ethyl acetate in heptane) afforded the title compound as a clear yellow oil. Sample contained some residual diisopropyl azodicarboxylate and carried forward without further purification. Yield: 2.52 g, 134%. LCMS m/z 282.0 {[M-(2-methyl-prop-1-ene)]+1}. $^1$H NMR (400 MHz, CDCl$_3$) δ 1.31 (d, J=6.8 Hz, 3H), 1.45 (s, 9H), 3.98-4.03 (m, 2H), 4.04-4.13 (m, 1H), 6.95 (dd, J=9.2, 4.2 Hz, 1H), 7.16-7.22 (m, 1H), 7.30 (dd, J=8.3, 3.0 Hz, 1H).

Step 2. Synthesis of (2S)-1-[(4-fluoro-2-(trifluoromethyl)phenoxy]propan-2-amine (C7). To a solution of tert-butyl{(2S)-1-[4-fluoro-2-(trifluoromethyl)phenoxy]propan-2-yl}carbamate (C6) (1.87 g, 5.54 mmol) in methanol (10 mL) was added a solution of hydrogen chloride (4 N in 1,4-dioxane, 5 mL). After 4 hours, the reaction mixture was concentrated in vacuo. The resulting residue was taken up in dichloromethane and washed with saturated aqueous sodium bicarbonate solution and water. The organic layer was dried over magnesium sulfate, filtered and concentrated in vacuo. Purification via silica gel chromatography (Gradient: 0 to 20% methanol in ethyl acetate) afforded the title compound as a yellow liquid. Yield: 785 mg, 3.31 mmol, 60%. LCMS m/z 238.1 (M+1). $^1$H NMR (400 MHz, CDCl$_3$) δ 1.19 (d, J=6.5 Hz, 3H), 3.35-3.44 (m, 1H), 3.74 (dd, J=8.4, 7.4 Hz, 1H), 3.94 (dd, J=8.5, 4.0 Hz, 1H), 6.93 (dd, J=9.1, 4.2 Hz, 1H), 7.18 (br ddd, J=9, 8, 3 Hz, 1H), 7.30 (dd, J=8.4, 3.1 Hz, 1H).

Step 3. Synthesis of (2S)—N-(2-{[tert-butyl(dimethyl)silyl]oxy}ethyl)-1-[(4-fluoro-2-(trifluoromethyl)phenoxy]propan-2-amine (C8). To a solution of (2S)-1-[4-fluoro-2-(trifluoromethyl)phenoxy]propan-2-amine (C7) (785 mg, 3.31 mmol) in dichloromethane (15 mL) was added {[tert-butyl(dimethyl)silyl]oxy}acetaldehyde (577 mg, 3.31 mmol). After 2 hours, sodium triacetoxyborohydride was added portion-wise. The reaction mixture was allowed to stir at room temperature overnight, then taken up in dichloromethane and washed with saturated aqueous sodium bicarbonate solution and water. The organic layer was concentrated in vacuo, then purified via silica gel chromatography (Gradient: 0 to 7% methanol in ethyl acetate) to afford the title compound as a clear liquid. Yield: 466 mg, 1.18 mmol, 36%. LCMS m/z 396.2 (M+1). $^1$H NMR (400 MHz, CDCl$_3$) δ 0.07 (s, 6H), 0.90 (s, 9H), 1.19 (d, J=6.4 Hz, 3H), 2.73-2.86 (m, 2H), 3.11-3.19 (m, 1H), 3.74 (dd, J=5.6, 5.4 Hz, 2H), 3.92 (d, J=5.5 Hz, 2H), 6.94 (dd, J=9.0, 4.0 Hz, 1H), 7.15-7.21 (m, 1H), 7.29 (dd, J=8.4, 3.1 Hz, 1H).

Step 4. Synthesis of 2-({(2S)-1-[(4-fluoro-2-(trifluoromethyl)phenoxy]propan-2-yl}amino)ethanol, hydrochloride salt (P4). To a solution of (2S)—N-(2-{[tert-butyl(dimethyl)silyl]oxy}ethyl)-1-[4-fluoro-2-(trifluoromethyl)phenoxy]propan-2-amine (C8) (460 mg, 1.16 mmol) in methanol (5 mL) was added a solution of hydrogen chloride (4N in dioxane, 2 mL). After 4 hours, the reaction mixture was concentrated in vacuo to afford the title compound as a clear gum. Yield: 398 mg, 100%. LCMS m/z 282.0 (M+1). $^1$H NMR (400 MHz, CD$_3$OD) δ 1.51 (d, J=6.8 Hz, 3H), 3.28-3.32 (m, 2H, assumed; largely obscured by solvent peak), 3.80-3.87 (m, 1H), 3.84 (dd, J=5.3, 5.2 Hz, 2H), 4.29 (dd, half of ABX pattern, J=10.6, 5.8 Hz, 1H), 4.38 (dd, half of ABX pattern, J=10.6, 4.0 Hz, 1H), 7.30 (dd, J=9.0, 4.2 Hz, 1H), 7.38-7.45 (m, 2H).

Preparation 5

2-[3-(trifluoromethyl)-1,2-oxazol-5-yl]phenol (P5)

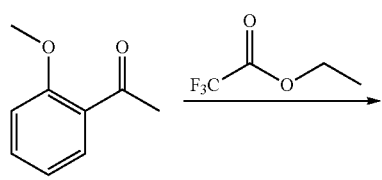

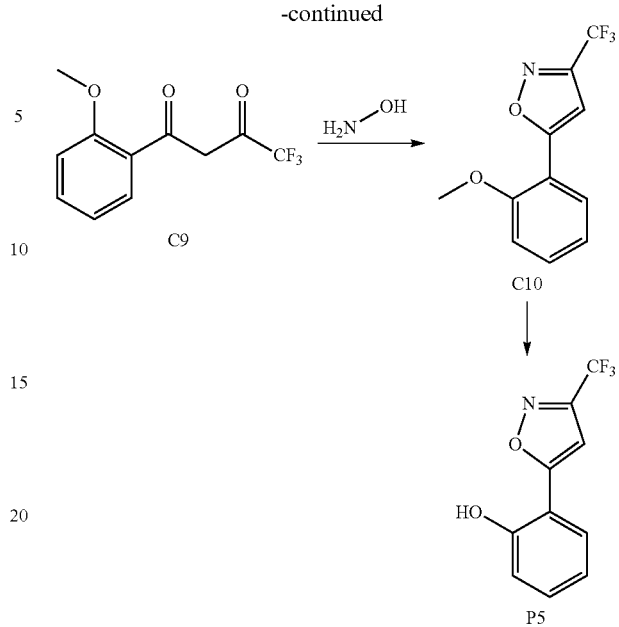

Step 1. Synthesis of 4,4,4-trifluoro-1-(2-methoxyphenyl)butane-1,3-dione (C9). To a suspension of sodium hydride (60% in mineral oil, 202 mg, 8.0 mmol) in 1,2-dimethoxyethane (4 mL) was added drop-wise ethyl trifluoroacetate (954 μL, 8.0 mmol) followed by 1-(2-methoxyphenyl)ethanone (552 μL, 4.0 mmol) and the reaction was heated to 160° C. in a microwave for 15 minutes. Aqueous hydrochloric acid (1 N, 20 mL) was added and the mixture was extracted with tert-butyl methyl ether (3×10 mL). The combined organic layers were dried over sodium sulfate and concentrated in vacuo. Purification via silica gel chromatography (Gradient: 0% to 10% tert-butyl methyl ether in heptanes) afforded the title compound as a red solid. Yield: 933 mg, 3.79 mmol, 95%. GCMS m/z 246 (M$^+$). $^1$H NMR (400 MHz, CDCl$_3$) δ 3.96 (s, 3H), 6.99 (s, 1H), 7.02 (br d, J=8.5 Hz, 1H), 7.08 (ddd, J=8, 7, 1.0 Hz, 1H), 7.55 (ddd, J=8.4, 7.4, 1.8 Hz, 1H), 7.99 (dd, J=7.9, 1.9 Hz, 1H).

Step 2. Synthesis of 5-(2-methoxyphenyl)-3-(trifluoromethyl)-1,2-oxazole (C10) A mixture of 4,4,4-trifluoro-1-(2-methoxyphenyl)butane-1,3-dione (C9) (933 mg, 3.79 mmol) and hydroxylamine hydrochloride (798 mg, 11.4 mmol) in ethanol (10 mL) was refluxed under nitrogen for 3 hours, then cooled to room temperature. The reaction was concentrated in vacuo, treated with water (30 mL) and extracted with dichloromethane (3×10 mL). The combined organic layers were dried over sodium sulfate and concentrated in vacuo. Purification via silica gel chromatography (Gradient: 0% to 20% ethyl acetate in heptanes) afforded the title compound as a yellow oil. Yield: 502 mg, 2.06 mmol, 54%. GCMS m/z 243 (M$^+$). $^1$H NMR (400 MHz, CDCl$_3$) δ 4.00 (s, 3H), 7.01 (s, 1H), 7.05 (dd, J=8.4, 0.9 Hz, 1H), 7.11 (ddd, J=7.8, 7.4, 1.1 Hz, 1H), 7.48 (ddd, J=8.4, 7.4, 1.8 Hz, 1H), 8.00 (dd, J=7.8, 1.7 Hz, 1H).

Step 3. Synthesis of 2-[3-(trifluoromethyl)-1,2-oxazol-5-yl]phenol (P5). To a mixture of 5-(2-methoxyphenyl)-3-(trifluoromethyl)-1,2-oxazole (C10) (502 mg, 2.06 mmol) and tetra-n-butylammonium iodide (915 mg, 2.48 mmol) in dichloromethane (20 mL) cooled to −78° C. was added boron trichloride (1 M in dichloromethane, 4.95 mL, 4.95 mmol). The reaction was allowed to stir at room temperature for 24 hours, and then cooled to −78° C., whereupon methanol (3 mL) was slowly added followed by water (30 mL). The mixture was extracted with dichloromethane (2×10 mL), and the combined organic layers were dried over sodium sulfate and concentrated in vacuo. Purification via silica gel chromatography (Gradient: 0% to 20% tert-butyl methyl ether in heptanes) afforded the title compound as a white solid. Yield: 283 mg, 1.23 mmol, 60%. $^1$H NMR (400 MHz, CDCl$_3$) δ 5.94 (s, 1H), 6.96 (br d, J=8.2 Hz, 1H), 7.02 (s, 1H), 7.09 (br dd, J=8, 8 Hz, 1H), 7.39 (ddd, J=8, 8, 1.6 Hz, 1H), 7.89 (dd, J=7.9, 1.7 Hz, 1H).

Preparation 6

4-Fluoro-2-(trifluoromethyl)-1,3-benzothiazol-7-ol (P6)

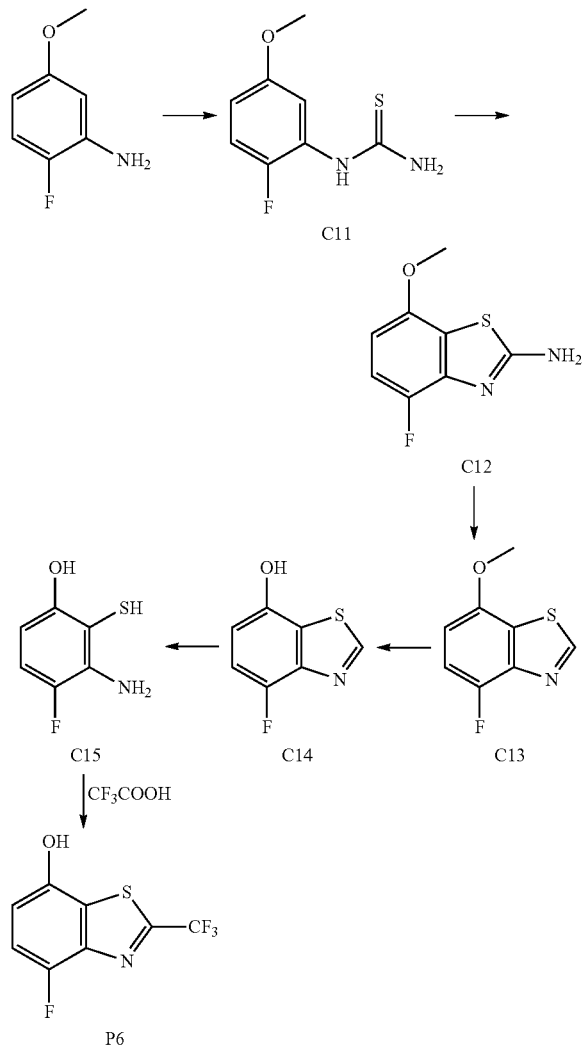

Step 1. Synthesis of 1-(2-fluoro-5-methoxyphenyl)thiourea (C11) To a solution of benzoyl isothiocyanate (20.20 g, 123.9 mmol) in acetone (350 mL) at 60° C. was added a solution of 2-fluoro-5-methoxyaniline (15.90 g, 112.6 mmol) in acetone (60 mL). The reaction mixture was refluxed for 2 hours and cooled to room temperature. The solution was concentrated to a volume of approximately 100 mL and then poured into ice water (900 mL). The resulting precipitate was collected, washed with water and hexanes, and dried at 40° C. under vacuum. It was then added into a solution of sodium hydroxide (15.00 g, 375.0 mmol) in water (300 mL) at 80° C. Heating was continued for 2 hours. After the reaction had cooled to room temperature, the pH was adjusted to 10 with concentrated hydrochloric acid. The precipitate was collected by filtration and washed with saturated aqueous sodium bicarbonate solution (2×250 mL), water (2×250 mL) and hexanes (2×250 mL) to afford the title compound as a white solid. Yield: 17.40 g, 86.9 mmol, 77%. $^1$H NMR (300 MHz, CDCl$_3$) δ 3.86 (s, 3H), 6.13 (br s, 1H), 6.82 (m, 1H), 6.90 (m, 1H), 7.13 (m, 1H), 7.63 (br s, 1H).

Step 2. Synthesis of 4-fluoro-7-methoxy-1,3-benzothiazol-2-amine (C12). To a suspension of 1-(2-fluoro-5-methoxyphenyl)thiourea (C11) (17.30 g, 86.40 mmol) in chloroform (160 mL) at 0° C. was added bromine (4.44 mL, 86.4 mmol) drop-wise. The reaction mixture was stirred at room temperature for 30 minutes and was then heated to reflux for 18 hours. It was poured into ice water (1.0 L) containing an excess of sodium bicarbonate. The resulting precipitate was collected by filtration and washed with water and hexanes to afford the title compound as a white solid. Yield: 15.40 g, 77.69 mmol, 90%. $^1$H NMR (300 MHz, DMSO-d$_6$): 3.84 (s, 3H), 6.60 (m, 1H), 7.03 (m, 1H), 7.73 (s, 2H), Step 3. Synthesis of 4-fluoro-7-methoxy-1,3-benzothiazole (C13) To a solution of 4-fluoro-7-methoxy-1,3-benzothiazol-2-amine (C12) (15.40 g, 77.69 mmol) in 1,4-dioxane (700 mL) was added isoamyl nitrite (15.0 mL, 111.6 mmol). The reaction mixture was stirred at 85° C. for 18 hours and then cooled to room temperature. The solvent was removed in vacuo, and purification was carried out with silica gel chromatography (Eluant: 1:1 dichloromethane/hexanes) to afford the title compound as a yellow solid. Yield: 12.0 g, 65.5 mmol, 84%. $^1$H NMR (300 MHz, CDCl$_3$) δ 3.98 (s, 3H), 6.77 (m, 1H), 7.16 (m, 1H), 8.98 (s, 1H).

Step 4. Synthesis of 4-fluoro-1,3-benzothiazol-7-ol (C14) To a solution of 4-fluoro-7-methoxy-1,3-benzothiazole (C13) (10.50 g, 57.30 mmol) in dichloromethane (250 mL) was added aluminum chloride (30.56 g, 229.2 mmol) in one portion at room temperature. The reaction mixture was stirred for 12 hours and additional aluminum chloride (30.56 g, 229.2 mmol) was added. After another 12 hours, the reaction mixture was poured into ice water (1.0 L). The resulting precipitate was collected by filtration, washed with water, and with 1:1 dichloromethane/hexanes to afford the title compound as a yellow solid. Yield: 6.60 g, 39.0 mmol, 68%. Melting point: 165-167° C. LCMS m/z 170.4 (M+1). $^1$H NMR (300 MHz, DMSO-d$_6$) δ 6.82 (m, 1H), 7.21 (m, 1H), 9.37 (s, 1H), 10.57 (s, 1H).

Step 5. Synthesis of 3-amino-4-fluoro-2-sulfanylphenol (C15) A solution of 4-fluoro-1,3-benzothiazol-7-ol (C14) (2.02 g, 11.93 mmol) in ethanol (20 mL) was treated with hydrazine monohydrate (12.7 mL, 167 mmol) and stirred for at 80° C. for 1 hour. The reaction was concentrated in vacuo and used directly in the following step.

Step 6. Synthesis of 4-fluoro-2-(trifluoromethyl)-1,3-benzothiazol-7-ol (P6). A mixture containing crude 3-amino-4-fluoro-2-sulfanylphenol (C15) (Step 1) and polyphosphoric acid trimethylsilyl ester (10 mL) in trifluoroacetic acid (20 mL) was stirred at 95° C. for 18 hours. After cooling to room temperature the reaction was treated with saturated aqueous sodium bicarbonate solution and extracted with dichloromethane (3×10 mL). The combined organic layers were dried over magnesium sulfate and concentrated in vacuo. Purification via silica gel chromatography (Gradient: 0% to 30% tert-butyl methyl ether in heptanes) afforded the title compound as a solid. Yield: 1.66 g, 7.0 mmol, 59%. GCMS m/z 237 (M$^+$). $^1$H NMR (400 MHz, CD$_3$OD) δ 6.90 (dd, J=8.7, 3.3 Hz, 1H), 7.21 (dd, J=10.2, 8.7 Hz, 1H).

Preparation 7

2-(3,3-Difluorocyclobutyl)-4-fluorophenol (P7)

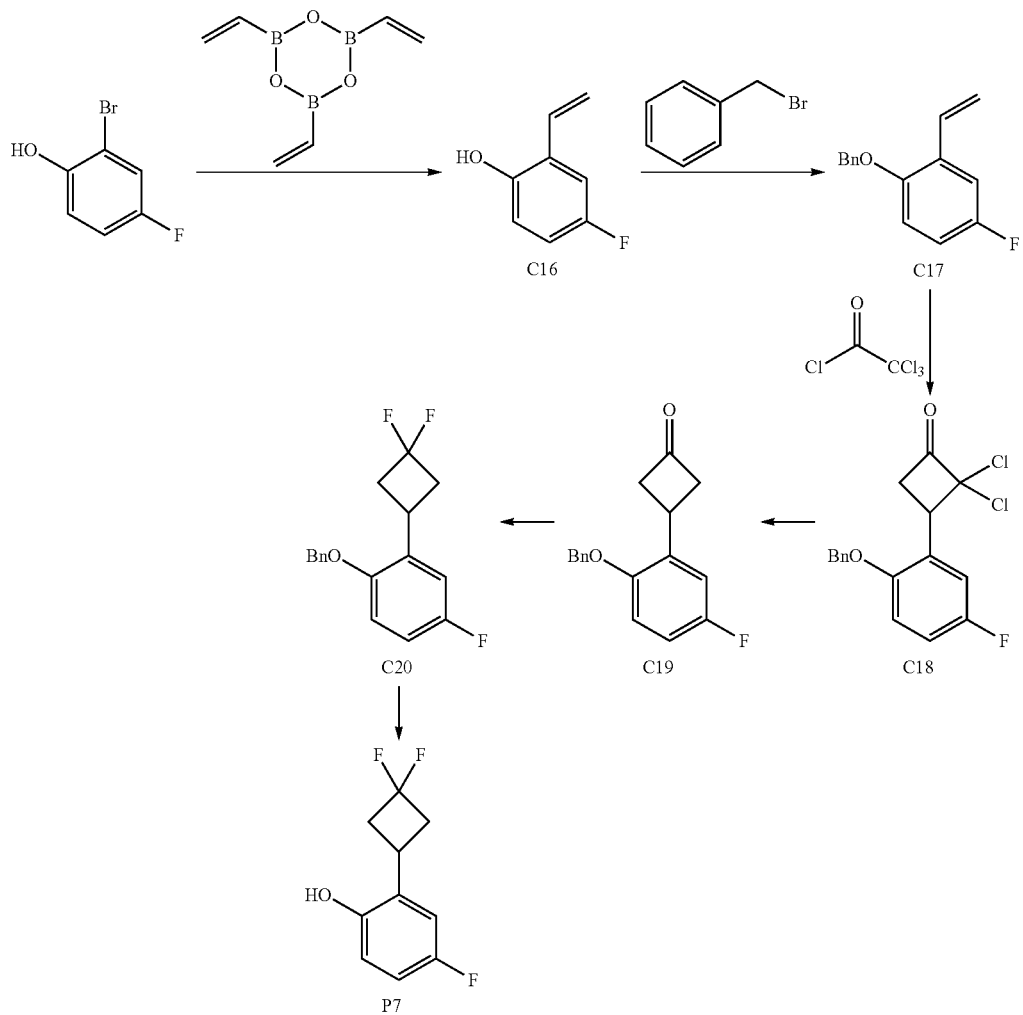

Step 1. Synthesis of 2-ethenyl-4-fluorophenol (C16). Nitrogen was bubbled through a mixture of 2-bromo-4-fluorophenol (1.6 g, 8.38 mmol), vinylboronic anhydride pyridine complex (95%, 806 mg, 3.35 mol) and potassium carbonate (1.17 g, 8.38 mmol) in 1,2-dimethoxyethane (15 mL) for 30 minutes. To this mixture was added palladium tetrakis (triphenylphosphine) (97.2 mg, 0.084 mmol). The reaction was allowed to stir at 90° C. for 16 hours. Water (50 mL) was added, and the mixture was extracted with ethyl acetate (2×100 mL). The combined organic layers were washed with aqueous sodium hydroxide solution (1 N, 100 mL) and saturated aqueous sodium chloride solution (100 mL), dried over magnesium sulfate and concentrated in vacuo. Purification via silica gel chromatography (Gradient: 0% to 30% ethyl acetate in heptanes) afforded the title compound as a white solid. Yield: 1.03 g, 7.46 mmol, 89%. $^1$H NMR (400 MHz, CDCl$_3$) δ 4.91 (br s, 1H), 5.41 (dd, J=11.1, 1.0 Hz, 1H), 5.74 (dd, J=17.6, 1.0 Hz, 1H), 6.74 (dd, J=8.8, 4.7 Hz, 1H), 6.82-6.95 (m, 2H), 7.10 (dd, J=9.5, 3.0 Hz, 1H).

Step 2. Synthesis of benzyl 2-ethenyl-4-fluorophenyl ether (C17). A mixture of 2-ethenyl-4-fluorophenol (C16) (1.03 g, 7.46 mmol) and potassium carbonate (3.12 g, 22.4 mmol) in acetone (35 mL) was treated with benzyl bromide (1.78 mL, 14.9 mmol) and stirred at reflux for 3 hours. The mixture was concentrated in vacuo, ethyl acetate (100 mL) was added and the mixture was washed with water (2×50 mL) and saturated aqueous sodium chloride solution (50 mL). The organic layer was dried over magnesium sulfate, and concentrated in vacuo. Purification via silica gel chromatography (Gradient: 0% to 15% ethyl acetate in heptane) afforded the title compound as a colorless oil. Yield: 1.64 g, 7.23 mmol, 97%. GCMS m/z 228 (M$^+$). $^1$H NMR (400 MHz, CDCl$_3$) δ 5.08 (s, 2H), 5.33 (dd, J=11.1, 1.0 Hz, 1H), 5.76 (dd, J=17.8, 1.0 Hz, 1H), 6.85-6.95 (m, 2H), 7.11 (ddd, J=17.8, 11.1, 1.5 Hz, 1H), 7.23 (dd, J=9.4, 2.9 Hz, 1H), 7.33-7.48 (m, 5H).

Step 3. Synthesis of 3-[(2-(benzyloxy)-5-fluorophenyl]-2,2-dichlorocyclobutanone (C18). Zinc-copper couple (1.71 g, 13.1 mmol) was added to a solution of benzyl 2-ethenyl-4-fluorophenyl ether (C17) (1.0 g, 4.38 mmol) in diethyl ether (15 mL). To this mixture was added drop-wise a mixture of phosphorus oxychloride (446 µL, 4.82 mmol) and trichloroacetyl chloride (978 µL, 8.76 mmol) in diethyl ether (5 mL).

The mixture was stirred at 40° C. for 2 hours, cooled to room temperature and stirred for an additional 18 hours. The solution was filtered through Celite, and the filtrate was washed with water (2×100 mL) and saturated aqueous sodium chloride solution (100 mL), dried over magnesium sulfate and concentrated in vacuo to afford the title compound as a colorless oil. Yield: 1.4 g, 4.13 mmol, 94%. $^1$H NMR (400 MHz, CDCl$_3$) δ 3.57 (dd, half of ABX pattern, J=18.0, 10.5 Hz, 1H), 3.65 (dd, half of ABX pattern, J=18.0, 9.4 Hz, 1H), 4.49 (dd, J=10.1, 9.8 Hz, 1H), 5.14 (AB quartet, J$_{AB}$=12.0 Hz, Δv$_{AB}$=12.2 Hz, 2H), 6.91-6.95 (m, 2H), 7.01 (ddd, J=9.0, 7.8, 2.9 Hz, 1H), 7.32-7.44 (m, 3H), 7.45-7.49 (m, 2H).

Step 4. Synthesis of 3-[(2-(benzyloxy)-5-fluorophenyl]cyclobutanone (C19). A mixture of 3-[2-(benzyloxy)-5-fluorophenyl]-2,2-dichlorocyclobutanone (C18) (1.4 g, 4.14 mmol) and zinc dust (1.08 g, 16.5 mmol) in acetic acid (25 mL) was stirred at room temperature for 2 hours and then at 100° C. for 1.25 hours. The mixture was filtered through Celite, and the filtrate was washed with water (50 mL) and saturated aqueous sodium chloride solution (50 mL), dried over magnesium sulfate and concentrated in vacuo. Purification via silica gel chromatography (Gradient: 0% to 30% ethyl acetate in heptanes) afforded the title compound as a colorless oil. Yield: 674 mg, 2.49 mmol, 60%. LCMS m/z 179.4 [M-(C$_7$H$_7$)]. $^1$H NMR (400 MHz, CDCl$_3$) δ 3.22-3.31 (m, 2H), 3.36-3.46 (m, 2H), 3.75-3.85 (m, 1H), 5.08 (s, 2H), 6.87-6.95 (m, 2H), 6.99 (dd, J=9.2, 2.7 Hz, 1H), 7.33-7.44 (m, 5H).

Step 5. Synthesis of benzyl 2-(3,3-difluorocyclobutyl)-4-fluorophenyl ether (C20). A solution of 3-[2-(benzyloxy)-5-fluorophenyl]cyclobutanone (C19) (600 mg, 2.22 mmol) in dichloromethane (20 mL) cooled to −78° C. was treated with (diethylamino)sulfur trifluoride (753 mg, 4.44 mmol) over a period of 5 minutes. The mixture was stirred at −78° C. for 30 minutes, whereupon it was allowed to warm to room temperature and stirring was continued for 16 hours. The mixture was cooled to −78° C. and a saturated aqueous sodium bicarbonate solution (10 mL) was added. The mixture was allowed to warm to room temperature and additional saturated aqueous sodium bicarbonate solution (50 mL) was added, followed by extraction with dichloromethane (2×50 mL). The combined organic layers were washed with saturated aqueous sodium chloride solution (50 mL), dried over magnesium sulfate, and concentrated in vacuo. Purification via silica gel chromatography (Gradient: 0% to 25% ethyl acetate in heptanes) afforded the desired title compound as a colorless oil. Yield: 315 mg, 108 mmol, 48%. GCMS m/z 292 (M$^+$). $^1$H NMR (400 MHz, CDCl$_3$) δ 2.58-2.73 (m, 2H), 2.90-3.03 (m, 2H), 3.53-3.64 (m, 1H), 5.06 (s, 2H), 6.83-6.94 (m, 3H), 7.34-7.45 (m, 5H).

Step 6. Synthesis of 2-(3,3-difluorocyclobutyl)-4-fluorophenol (P7). A mixture of benzyl 2-(3,3-difluorocyclobutyl)-4-fluorophenyl ether (C20) (60 mg, 0.20 mmol) in ethanol (15 mL) was treated with palladium (50 mg, 0.47 mmol) and shaken on a Parr hydrogenator (50 psi) at room temperature for 2 hours. The mixture was filtered through Celite and concentrated in vacuo to afford the title compound as a yellow oil. Yield: 20 mg, 0.065 mmol, 100%. GCMS m/z 202 (M$^+$).

$^1$H NMR (400 MHz, CDCl$_3$) δ 2.60-2.78 (m, 2H), 2.92-3.07 (m, 2H), 3.46-3.58 (m, 1H), 6.61-6.95 (m, 3H).

Preparation 8

2-[2-(2-Bromophenoxy)ethyl]-7-(4-methyl-1H-imidazol-1-yl)-3,4-dihydro-2H-pyrido[1,2-a]pyrazine-1,6-dione (P8)

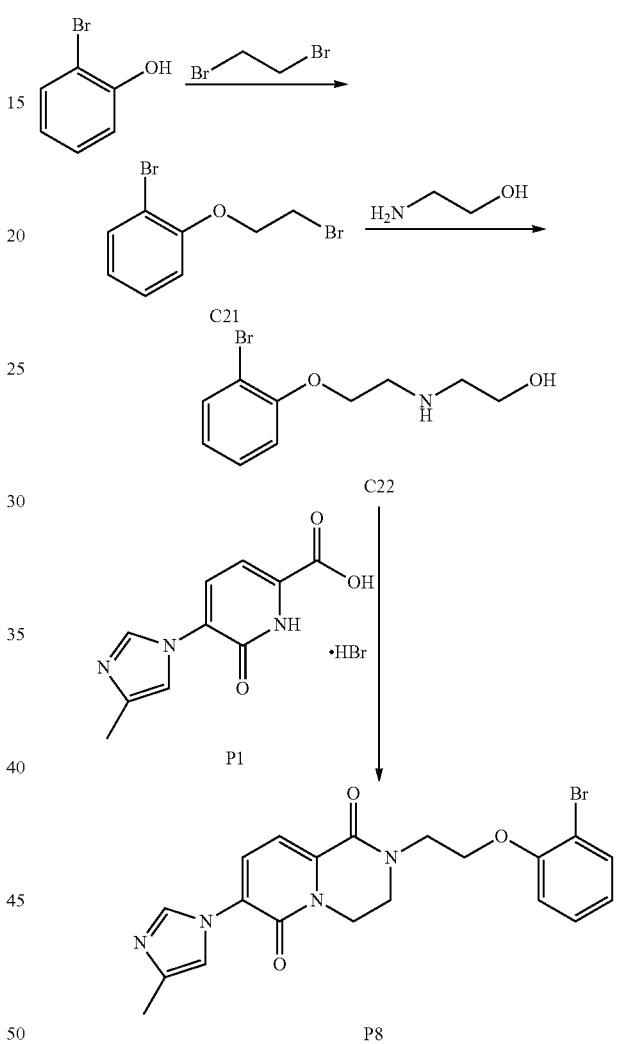

Step 1. Synthesis of 1-bromo-2-(2-bromoethoxy)benzene (C21). A suspension of 2-bromophenol (3.50 g, 20.23 mmol), 1,2-dibromoethane (19.00 g, 101 mmol), and potassium carbonate (7.06 g, 2.92 mmol) in acetonitrile (50 mL) was heated to 80° C. After heating overnight, the reaction mixture was cooled to room temperature, diluted with ethyl acetate and washed with water and saturated aqueous sodium chloride solution. The organic layer was dried over magnesium sulfate, filtered and the filtrate was concentrated in vacuo to afford the title compound as a clear oil. Yield: 6.36 g, 100%. $^1$H NMR (400 MHz, CDCl$_3$) δ 3.69 (dd, J=6.6, 6.4 Hz, 2H), 4.35 (dd, J=6.7, 6.4 Hz, 2H), 6.87-6.94 (m, 2H), 7.25-7.30 (m, 1H), 7.56 (dd, J=7.9, 1.6 Hz, 1H).

Step 2. Synthesis of 2-{[2-(2-bromophenoxy)ethyl]amino}ethanol (C22). A solution of 1-bromo-2-(2-bromoethoxy)benzene (C21) (5.66 g, 20.22 mmol) and 2-aminoethanol (12.30 g, 202 mmol) in 2-propanol (50 mL) was heated to 80° C. After heating overnight, the reaction mixture was cooled to room temperature and concentrated in vacuo. The resulting residue was taken up in dichloroethane and washed with saturated aqueous sodium bicarbonate solution and water. The organic layer was dried over magnesium sulfate, filtered and the filtrate was concentrated in vacuo to afford the title compound as a clear yellow oil. Yield: 5.12 g, 20.18 mmol, 97%. LCMS m/z 259.9 (M+1). $^1$H NMR (400 MHz, CDCl$_3$) δ 2.88 (dd, J=5.3, 5.1 Hz, 2H), 3.08 (dd, J=5.1, 5.1 Hz, 2H), 3.67 (dd, J=5.3, 5.3 Hz, 2H), 4.14 (dd, J=5.1, 5.1 Hz, 2H), 6.85 (ddd, J=7.6, 7.6, 1.3 Hz, 1H), 6.91 (dd, J=8.2, 1.2 Hz, 1H), 7.26 (ddd, J=8.2, 7.6, 1.5 Hz, 1H), 7.54 (dd, J=8.0, 1.6 Hz, 1H).

Step 3. Synthesis of 2-[2-(2-bromophenoxy)ethyl]-7-(4-methyl-1H-imidazol-1-yl)-3,4-dihydro-2H-pyrido[1,2-a]pyrazine-1,6-dione (P8). A mixture of compound P1 (1.5 g, 5.0 mmol), 2-{[2-(2-bromophenoxy)ethyl]amino}ethanol (C22) (1.95 g, 7.5 mmol), O-(7-azabenzotriazol-1-yl)-N,N,N',N'-tetramethyluronium hexafluorophosphate (HATU, 6.46 g, 12 mmol) and N,N-diisopropylethylamine (3.5 g, 27 mmol) in dichloromethane (50 mL) was stirred for 24 hours. The reaction was poured into water and the aqueous phase was extracted with dichloromethane (2×100 mL). The combined organic layers were dried over sodium sulfate, filtered, and concentrated in vacuo. The residue was treated with ethyl acetate (10 mL), filtered and the collected solid was washed with ethyl acetate to afford the title compound as a yellow solid. Yield: 1.5 g, 3.4 mmol, 68%. LCMS m/z 442.9 (M+1). $^1$H NMR (400 MHz, DMSO-d$_6$) δ 2.15 (s, 3H), 3.88-3.96 (m, 4H), 4.24-4.30 (m, 4H), 6.90 (dd, J=8, 8 Hz, 1H), 7.08 (d, J=7.8 Hz, 1H), 7.15 (br d, J=8 Hz, 1H), 7.34 (dd, J=8, 8 Hz, 1H), 7.40 (br s, 1H), 7.58 (br d, J=8 Hz, 1H), 7.78 (d, J=7.9 Hz, 1H), 8.25 (s, 1H).

Preparation 9

2-(Trifluoromethyl)-1,3-benzothiazol-7-ol (P9)

cooled to room temperature, filtered through Celite and concentrated in vacuo to afford the title compound as a solid. Yield: 2.57 g, 10.77 mmol, 100%. LCMS m/z 202.1 (M+1). $^1$H NMR (400 MHz, CD$_3$OD) δ 3.77 (s, 3H), 6.30 (d, J=8.0 Hz, 1H), 6.43 (d, J=8.0 Hz, 1H), 6.98 (dd, J=8.0, 8.0 Hz, 1H).

Step 2. Synthesis of N-(2-bromo-3-methoxyphenyl)-2,2,2-trifluoroacetamide (C24). Trifluoroacetic anhydride (3.0 mL, 22 mmol) was added to a solution of 2-bromo-3-methoxyaniline (C23) (2.57 g, 10.77 mmol) and triethylamine (4.51 mL, 32.3 mmol) in dichloromethane (30 mL) at −78° C. The reaction was allowed to warm to room temperature and stirring was continued for 18 hours, whereupon the mixture was poured into water (40 mL) and extracted with dichloromethane (2×20 mL). The combined organic layers were dried over sodium sulfate and concentrated in vacuo. Purification via silica gel chromatography (Gradient: 0% to 30% methyl tert-butyl ether in hexanes) afforded the title compound as a colorless solid. Yield: 2.97 g, 9.96 mmol, 92%. GCMS m/z 297, 299 (M$^+$). $^1$H NMR (400 MHz, CDCl$_3$) δ 3.94 (s, 3H), 6.81 (dd, J=8.4, 1.2 Hz, 1H), 7.35 (dd, J=8.4, 8.3 Hz, 1H), 7.97 (dd, J=8.3, 1.3 Hz, 1H), 8.59 (br s, 1H).

Step 3. Synthesis of N-(2-bromo-3-methoxyphenyl)-2,2,2-trifluoroethanethioamide (C25). A solution of N-(2-bromo-3-methoxyphenyl)-2,2,2-trifluoroacetamide (C24) (776 mg, 2.6 mmol) and Lawesson's reagent (1.07 g, 2.6 mmol) in 1,4-dioxane (13 mL) was heated to 135° C. overnight. The mixture was cooled to room temperature, filtered, and concentrated in vacuo. Purification via silica gel chromatography (Gradient: 0% to 20% ethyl acetate in heptanes) afforded the title compound as an oil. Yield: 839 mg, 2.60 mmol, quantitative. LCMS m/z 314.0 (M+1). $^1$H NMR (400 MHz, CDCl$_3$) δ 3.95 (s, 3H), 6.92 (dd, J=8.3, 1.1 Hz, 1H), 7.39 (dd, J=8.4, 8.3 Hz, 1H), 8.28 (dd, J=8.2, 0.8 Hz, 1H), 9.75 (br s, 1H).

Step 4. Synthesis of 7-methoxy-2-(trifluoromethyl)-1,3-benzothiazole (C26). To a solution of N-(2-bromo-3-methoxyphenyl)-2,2,2-trifluoroethanethioamide (C25) (748 mg, 2.38 mmol) in 1,2-dimethoxyethane (11.9 mL) was added 1,10-phenanthroline (88.4 mg, 0.48 mmol), cesium carbonate (1.55 g, 4.76 mmol), and copper iodide (45.3 mg, 0.24 mmol).

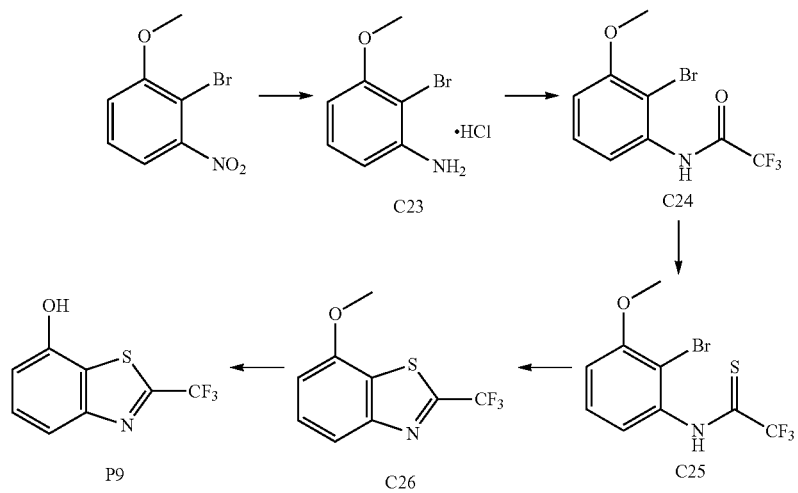

Step 1. Synthesis of 2-bromo-3-methoxyaniline (C23). Iron (1.94 g, 34 mmol) was added to a solution of 2-bromo-1-methoxy-3-nitrobenzene (2.50 g, 10.77 mmol) in ethanol (18 mL) and concentrated hydrochloric acid (1 mL), and the reaction was heated at reflux for 1.5 hours. The mixture was Nitrogen was bubbled through the reaction for 30 minutes and the reaction was heated to 80° C. for 48 hours. The mixture was cooled to room temperature, filtered and concentrated in vacuo. Purification via silica gel chromatography (Gradient: 0% to 30% diethyl ether in hexanes) afforded the title compound as a colorless solid. Yield: 398 mg, 1.71 mmol, 72%. GCMS m/z 233 (M+). $^1$H NMR (400 MHz, CDCl$_3$) δ 4.03 (s, 3H), 6.97 (br d, J=7.9 Hz, 1H), 7.56 (dd, J=8.3, 8.0 Hz, 1H), 7.82 (dd, J=8.3, 0.6 Hz, 1H).

Step 5. Synthesis of 2-(trifluoromethyl)-1,3-benzothiazol-7-ol (P9). A solution of 7-methoxy-2-(trifluoromethyl)-1,3-benzothiazole (C26) (398 mg, 1.71 mmol) in dichloromethane (10 mL) at −78° C. was treated with boron tribromide (1 M in dichloromethane, 3.41 mL, 3.41 mmol), warmed to room temperature and stirred for 18 hours. Methanol (3.0 mL) was added to the mixture at −78° C. and the mixture was warmed to room temperature. Water (30 mL) was added and the mixture was extracted with dichloromethane (2×10 mL). The combined organic layers were dried over sodium sulfate and concentrated in vacuo. Purification via silica gel chromatography (Gradient: 0% to 20% methyl tert-butyl ether in heptanes) afforded the title compound as a colorless solid. Yield: 251 mg, 1.15 mmol, 67%. GCMS m/z 219 (M+). $^1$H NMR (400 MHz, CDCl$_3$) δ 6.44 (br s, 1H), 6.95 (d, J=7.8 Hz, 1H), 7.47 (dd, J=8.2, 8.0 Hz, 1H), 7.82 (d, J=8.2 Hz, 1H).

Preparation 10

2'-Methyl-2-oxo-1,2-dihydro-3,4'-bipyridine-6-carboxylic acid, hydrochloride salt (P10)

heated under reflux for 7 hours. The reaction was then concentrated under reduced pressure to an approximate volume of 200 mL and purified by chromatography on silica gel (Gradient: 80% to 100% ethyl acetate in heptane, followed by 5% to 10% methanol in ethyl acetate) to yield the title compound as a brown solid. Yield: 32.9 g, 0.158 mol, 61%. LCMS m/z 210.0 (M+1). $^1$H NMR (400 MHz, CDCl$_3$) δ 7.09 (dd, J=7.8, 6.9 Hz, 1H), 7.52 (d, J=8.2 Hz, 1H), 8.33 (d, J=6.4 Hz, 1H).

Step 2. Synthesis of 5-bromo-6-chloropyridine-2-carbonitrile (C28). Trimethylsilyl cyanide (19 mL, 0.15 mol) was added to a stirred solution of 3-bromo-2-chloropyridine 1-oxide (C27) (31.6 g, 0.152 mol) and triethylamine (63.4 mL, 0.46 mol) in acetonitrile (400 mL). The reaction mixture was heated to 50° C. for 2 hours. It was then cooled to room temperature and additional trimethylsilyl cyanide (19 mL, 0.15 mol) was added. After the reaction mixture was heated at 50° C. for 1.5 hours, a final portion of trimethylsilyl cyanide (28.5 mL, 0.23 mol) was added and the reaction was heated at reflux for 3 days. After dilution with dichloromethane (2 L), the reaction was washed with saturated aqueous sodium bicarbonate solution (800 mL), then with water (1 L), dried over magnesium sulfate and concentrated in vacuo. Purification via silica gel chromatography (Gradient: 20% to 25% ethyl acetate in heptane) afforded the title compound as a yellow solid. Yield: 14.92 g, 68.6 mmol, 45%.

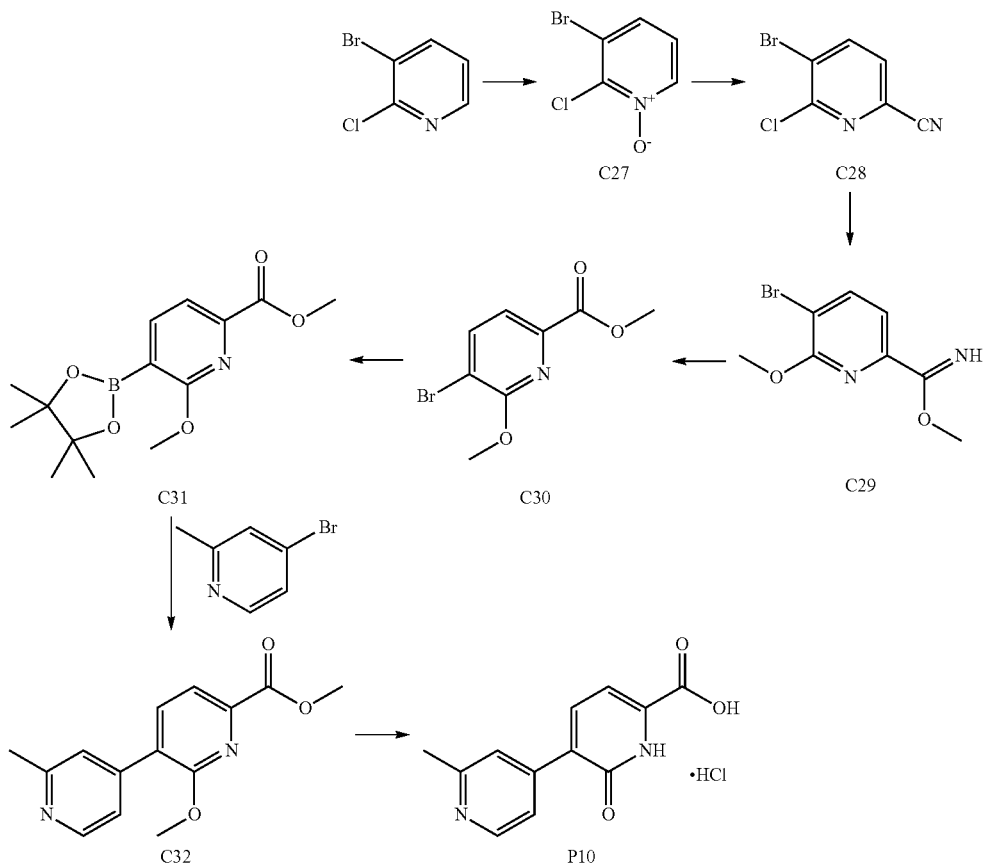

Step 1. Synthesis of 3-bromo-2-chloropyridine 1-oxide (C27). A solution of 3-bromo-2-chloropyridine (50 g, 0.26 mol) and 3-chloroperoxybenzoic acid (70-75% wet with water; 67.3 g, 0.39 mol) in 1,2-dichloroethane (600 mL) was The reaction was also performed using the acylating agent dimethylcarbamoyl chloride. A solution of dimethylcarbamoyl chloride (12.9 mL, 0.14 mol) in dichloromethane (23 mL) was added drop-wise to a stirred solution of 3-bromo-2-chloropyridine 1-oxide (C27) (11.23 g, 53.9 mmol) and trimethylsilyl cyanide (17.5 mL, 0.14 mol) in dichloromethane (200 mL). The reaction mixture was heated under reflux for 3 days, then diluted with dichloromethane (450 mL) and washed with saturated aqueous sodium bicarbonate solution (2×200 mL), then with water (200 mL), dried over magnesium sulfate and concentrated in vacuo. Purification via silica gel chromatography (Gradient: 15% to 20% ethyl acetate in heptane) provided the title compound, contaminated with dimethylcarbamoyl cyanide (12.73 g, 100%) as an off-white solid. The impurity was reduced by repeatedly washing with aqueous sodium hydroxide solution (2 N) and a second chromatography on silica gel. Although the impurity could not be completely removed, the material was used in the next step without any detrimental effects. Yield: 7.83 g, 36.0 mmol, 67%. $^1$H NMR (400 MHz, CDCl$_3$) δ 7.52 (d, J=7.8 Hz, 1H), 8.12 (d, J=7.8 Hz, 1H).

Step 3. Synthesis of methyl 5-bromo-6-methoxypyridine-2-carboximidoate (C29). Sodium hydride (60% dispersion in mineral oil, 3.57 g, 93.8 mmol) was added portion-wise over a 20 minute period to a stirred solution of methanol (7.1 mL) in tetrahydrofuran (123 mL) under argon; the reaction was then stirred for an additional 55 minutes. A solution of 5-bromo-6-chloropyridine-2-carbonitrile (C28) (8.16 g, 37.5 mmol) in tetrahydrofuran (71 mL) was then added drop-wise and the reaction mixture was stirred for 18 hours. After being quenched with saturated aqueous ammonium chloride solution (200 mL), the mixture was extracted with ethyl acetate (2×400 mL). The combined organic layers were washed with saturated aqueous sodium chloride solution (200 mL), dried over magnesium sulfate and concentrated in vacuo to give the crude title compound (9.42 g, quantitative) as an orange solid, which was used in the next step without further purification, as it was found to be unstable on silica gel. LCMS m/z 247.1 (M+1). $^1$H NMR (400 MHz, CDCl$_3$) δ 3.99 (s, 3H), 4.09 (s, 3H), 7.32 (d, J=7.8 Hz, 1H), 7.90 (d, J=7.8 Hz, 1H).

Step 4. Synthesis of methyl 5-bromo-6-methoxypyridine-2-carboxylate (C30). A stirred solution of methyl 5-bromo-6-methoxypyridine-2-carboximidoate (C29) (9.42 g, 38.4 mmol) in methanol (66 mL) and concentrated hydrochloric acid (6.6 mL) was heated under reflux for 18 hours. The reaction was concentrated to dryness under reduced pressure. The resulting solid was dissolved in dichloromethane (500 mL) and washed with saturated aqueous sodium bicarbonate solution (250 mL). The aqueous phase was extracted with dichloromethane (200 mL), and the combined organics were washed with water (250 mL), with saturated aqueous sodium chloride solution (250 mL), dried over magnesium sulfate and concentrated under reduced pressure to provide the title compound. The reaction was repeated on additional material (1.65 g, 6.73 mmol), worked up in a similar manner, combined with the first reaction, and purified by silica gel chromatography (Eluant: 10% ethyl acetate in heptane) to provide the title compound as a yellow solid. Yield: 4.48 g, 18.2 mmol, 40%. LCMS m/z 246.1 (M+1). $^1$H NMR (400 MHz, CDCl$_3$) δ 3.97 (s, 3H), 4.11 (s, 3H), 7.59 (d, J=7.8 Hz, 1H), 7.93 (d, J=7.8 Hz, 1H).

Step 5. Synthesis of methyl 6-methoxy-5-(4,4,5,5-tetramethyl-1,3,2-dioxaborolan-2-yl)pyridine-2-carboxylate (C31). [1,1'-Bis(diphenylphosphino)ferrocene]dichloropalladium(II), complex with dichloromethane (740 mg, 0.91 mmol) was added in one portion to a degassed mixture of methyl 5-bromo-6-methoxypyridine-2-carboxylate (C30) (7.42 g, 30.2 mmol), 4,4,4',4',5,5,5',5'-octamethyl-2,2'-bi-1,3,2-dioxaborolane (9.19 g, 36.2 mmol) and potassium acetate (8.88 g, 90.5 mmol) in dioxane (150 mL) at room temperature under argon and the reaction was heated at 100° C. for 18 hours. The mixture was cooled to room temperature, filtered through Celite, washed with ethyl acetate (400 mL) and concentrated in vacuo. Silica gel chromatography (Gradient: 15% to 35% ethyl acetate in heptane) afforded the title compound as a colorless oil, which solidified on standing to form a white crystalline solid. Yield: 7.14 g, 24.4 mmol, 81%. LCMS m/z 212.1 (M for boronic acid+1). $^1$H NMR (400 MHz, CDCl$_3$) δ 1.37 (s, 12H), 3.97 (s, 3H), 4.06 (s, 3H), 7.67 (d, J=7.3 Hz, 1H), 8.09 (d, J=7.3 Hz, 1H). A second crop of material (1.13 g, 13%) was also obtained from the purification; this contained minor impurities by NMR analysis.

Step 6. Synthesis of methyl 2-methoxy-2'-methyl-3,4'-bipyridine-6-carboxylate (C32). Degassed 1,2-dimethoxyethane (60 mL) and water (0.5 mL) were added to a flask charged with 4-bromo-2-methylpyridine (1.20 g, 6.98 mmol), methyl 6-methoxy-5-(4,4,5,5-tetramethyl-1,3,2-dioxaborolan-2-yl)pyridine-2-carboxylate (C31) (3.07 g, 10.5 mmol), potassium phosphate (4.44 g, 20.9 mmol), and tetrakis(triphenylphosphine)palladium(0) (0.81 g, 0.70 mmol). The mixture was heated to 80° C. for 18 hours, then cooled to room temperature and concentrated in vacuo. Silica gel chromatography (Eluant: ethyl acetate) provided a solid, which was triturated twice with a 1:5 mixture of ethyl acetate and heptane to provide the title compound as a white solid. Yield: 1.68 g, 6.50 mmol, 93%. LCMS m/z 259.1 (M+1). $^1$H NMR (400 MHz, CDCl$_3$) δ 2.63 (s, 3H), 4.00 (s, 3H), 4.09 (s, 3H), 7.32 (br d, J=5.5 Hz, 1H), 7.36 (br s, 1H), 7.79 (AB quartet, $J_{AB}$=7.3 Hz, $\Delta v_{AB}$=24.1 Hz, 2H), 8.57 (d, J=5.0 Hz, 1H).

Step 7. Synthesis of 2'-methyl-2-oxo-1,2-dihydro-3,4'-bipyridine-6-carboxylic acid, hydrochloride salt (P10). Methyl 2-methoxy-2'-methyl-3,4'-bipyridine-6-carboxylate (C32) (1.25 g, 4.84 mmol) was dissolved in dioxane (40 mL) and aqueous hydrochloric acid (37%, 40 mL), and heated to reflux for 18 hours. The reaction was cooled and concentrated to dryness, azeotroped with toluene and methanol and again concentrated to dryness. This process was repeated twice and the resulting solid was triturated three times with a 1:2:0.5 mixture of ethyl acetate/heptane/methanol to give the title compound as a yellow solid. Yield: 1.30 g, 4.87 mmol, quantitative. LCMS m/z 231.1 (M+1). $^1$H NMR (400 MHz, DMSO-d$_6$) δ 2.76 (s, 3H), 7.08 (d, J=7.3 Hz, 1H), 8.24 (d, J=7.3 Hz, 1H), 8.31-8.38 (m, 2H), 8.76 (d, J=6.0 Hz, 1H), 12.2 (v br s, 1H).

Preparation 11

4-(4-Chloro-1H-imidazol-1-yl)-6-oxo-1,6-dihydropyridine-2-carboxylic acid, hydrochloride salt (P11)

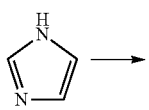

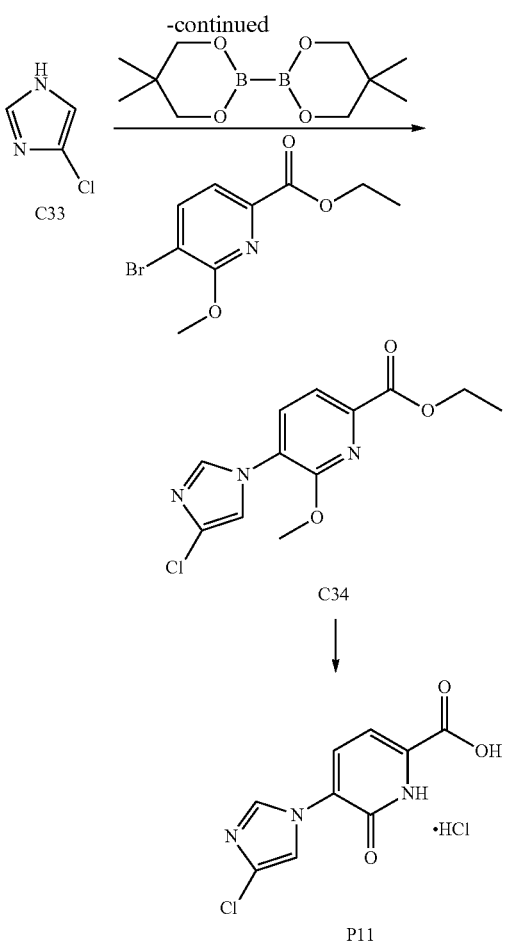

Step 1. Synthesis of 4-chloro-1H-imidazole (C33). To a solution of 1H-imidazole (22.1 g, 324 mmol) in N,N-dimethylformamide at 0° C. was added drop-wise (over 4 hours) a solution of N-chlorosuccinimide (25 g, 190 mmol) in N,N-dimethylformamide (total solvent, 160 mL). The reaction was stirred at 0° C. for 1 hour, whereupon water (200 mL) was added at 0° C. The mixture was extracted with ethyl acetate (3×50 mL), and the combined organic layers were concentrated in vacuo. Purification was carried out using supercritical fluid chromatography (Column: Princeton Cyano, 5 μm; Eluant: 15:85 methanol/carbon dioxide). The resulting material was purified again, using silica gel chromatography (Mobile phase A: ethyl acetate; Mobile phase B: [20% (2 M ammonia in methanol) in dichloromethane]; Gradient: 0% to 10% B) to afford the title compound as a white solid. Yield: 2.45 g, 23.9 mmol, 12%. GCMS m/z 102, 104 (M+). $^1$H NMR (400 MHz, CDCl$_3$) δ 7.00 (d, J=1.2 Hz, 1H), 7.57 (br s, 1H), 11.3 (v br s, 1H).

Step 2. Synthesis of ethyl 4-(4-chloro-1H-imidazol-1-yl)-6-methoxypyridine-2-carboxylate (C34). 1,1-Bis(diphenylphosphino)ferrocene-palladium(II) dichloride-dichloromethane complex (49.8 mg, 0.068 mmol) was added to a solution of ethyl 5-bromo-6-methoxypyridine-2-carboxylate (prepared in analogous fashion to methyl 5-bromo-6-methoxypyridine-2-carboxylate (C30) in Preparation 10; 254 mg, 0.97 mmol), 5,5,5',5'-tetramethyl-2,2'-bi-1,3,2-dioxaborinane (264 mg, 1.17 mmol), and potassium acetate (293 mg, 2.92 mmol) in 1,4-dioxane (8 mL). The reaction was stirred at 85° C. for 6 hours, whereupon it was allowed to cool to room temperature. Dichloromethane was added, and the resulting mixture was washed with saturated aqueous sodium bicarbonate solution, dried over magnesium sulfate, and concentrated in vacuo to afford intermediate ethyl 5-(5,5-dimethyl-1,3,2-dioxaborinan-2-yl)-6-methoxypyridine-2-carboxylate. To a solution of ethyl 5-(5,5-dimethyl-1,3,2-dioxaborinan-2-yl)-6-methoxypyridine-2-carboxylate (crude) in methanol (50 mL) was added 4-chloro-1H-imidazole (C33) (100 mg, 0.97 mmol) and copper(I) oxide (14 mg, 0.098 mmol) and the reaction was stirred at ambient temperature overnight. The mixture was heated to 50° C. for 2 hours, and additional copper(I) oxide (14 mg, 0.098 mmol) was added. The reaction was heated to reflux for 2 hours and was then filtered through Celite. The Celite pad was washed with methanol, and the combined filtrate and washings were concentrated in vacuo. Purification was carried out twice via silica gel chromatography (Gradient: 0% to 50% ethyl acetate in heptane, then 0% to 40% ethyl acetate in heptane), affording the title compound as a white solid. Yield: 29.3 mg, 0.104 mmol, 11%. LCMS m/z 282.1 (M+1). $^1$H NMR (400 MHz, CDCl$_3$) δ 1.44 (t, J=7.1 Hz, 3H), 4.14 (s, 3H), 4.46 (q, J=7.1 Hz, 2H), 7.24 (d, J=1.6 Hz, 1H), 7.67 (d, J=7.8 Hz, 1H), 7.82-7.83 (m, 1H), 7.84 (d, J=7.8 Hz, 1H).

Step 3. Synthesis of 4-(4-chloro-1H-imidazol-1-yl)-6-oxo-1,6-dihydropyridine-2-carboxylic acid, hydrochloride salt (P11). To a solution of 4-(4-chloro-1H-imidazol-1-yl)-6-methoxypyridine-2-carboxylate (C34) (20.9 mg, 0.074 mmol) in acetic acid (0.5 mL) was added concentrated hydrochloric acid and the reaction was stirred at 95° C. for 18 hours. Removal of solvent in vacuo afforded the title compound as a white solid. Yield: 20.4 mg, 0.074 mmol, 100%. LCMS m/z 240.3 (M+1). $^1$H NMR (400 MHz, CD$_3$OD) δ 7.19 (d, J=7.5 Hz, 1H), 7.94-7.98 (m, 2H), 9.01-9.05 (m, 1H).

Preparation 12

(2S)-2-[(tert-Butoxycarbonyl)amino]propyl methanesulfonate (P12)

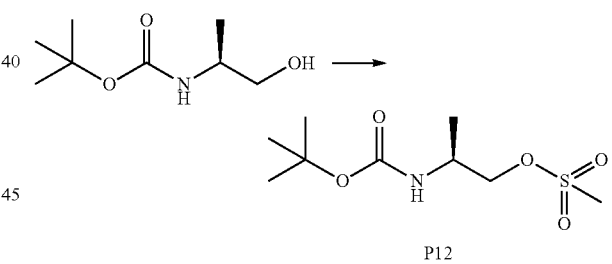

Methanesulfonyl chloride (13.2 mL, 170 mmol) was added to a 0° C. solution of tert-butyl [(2S)-1-hydroxypropan-2-yl] carbamate (28.4 g, 162 mmol) and triethylamine (27 mL, 190 mmol) in dichloromethane (350 mL), and the reaction mixture was allowed to stir for 30 minutes. After aqueous ammonium chloride solution was added to the reaction mixture, the aqueous layer was extracted with dichloromethane, and the combined organic layers were dried over magnesium sulfate, filtered, and concentrated in vacuo. The resulting sticky white solid was slurried with diethyl ether (100 mL), stirred for 10 minutes, and filtered to afford the product as a white solid. Yield: 28.8 g, 114 mmol, 70%. The filtrate was concentrated under reduced pressure and recrystallized from diethyl ether (the hot mixture was filtered through Celite before crystallization) to provide additional product as a white solid. Yield: 11.66 g, 45.63 mmol, combined yield 98%. $^1$H NMR (400 MHz, CDCl$_3$) δ 1.24 (d, J=7.0 Hz, 3H), 1.45 (s, 9H), 3.04 (s, 3H), 3.91-4.04 (br m, 1H), 4.16 (dd, half of ABX pattern, J=10.1, 4.2 Hz, 1H), 4.19-4.28 (br m, 1H), 4.62 (br s, 1H).

Preparation 13

(2S)-1-[4-Fluoro-2-(1,1,1-trifluoropropan-2-yl)phenoxy]propan-2-amine (P13)

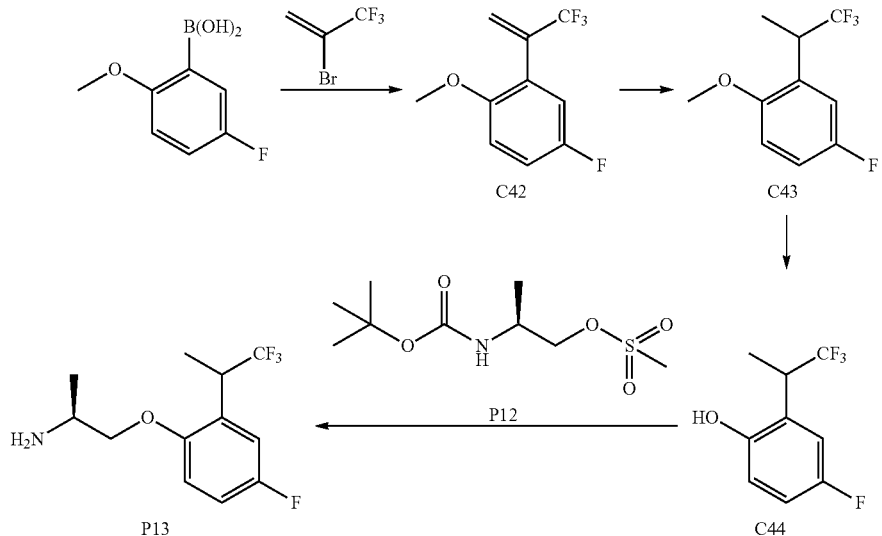

Step 1. Synthesis of 4-fluoro-1-methoxy-2-(3,3,3-trifluoroprop-1-en-2-yl)benzene (C42). Dichlorobis(triphenylphosphine)palladium(II) (98%, 530 mg, 0.74 mmol) was added to a mixture of (5-fluoro-2-methoxyphenyl)boronic acid (10.0 g, 58.8 mmol), 2-bromo-3,3,3-trifluoroprop-1-ene (6.75 mL, 65.0 mmol) and potassium carbonate (16.3 g, 118 mmol) in tetrahydrofuran (100 mL) and water (30 mL), and the reaction mixture was stirred for 18 hours at room temperature. The aqueous layer was extracted with diethyl ether (100 mL), and the combined organic layers were washed with saturated aqueous sodium chloride solution, dried over magnesium sulfate, filtered, and concentrated in vacuo, while keeping the bath temperature at <30° C. Pentane (200 mL) was added, the mixture was filtered, and the filtrate was concentrated under reduced pressure; the residue was subjected to silica gel chromatography (Eluent: pentane) to afford the product as a colorless oil. Yield: 9.08 g, 41.2 mmol, 70%. $^1$H NMR (400 MHz, CDCl$_3$) δ 3.80 (s, 3H), 5.69-5.70 (m, 1H), 6.12-6.13 (m, 1H), 6.88 (dd, J=9.0, 4.5 Hz, 1H), 6.98 (br dd, J=8.8, 3.1 Hz, 1H), 7.05 (ddd, J=9.0, 7.8, 3.1 Hz, 1H).

Step 2. Synthesis of 4-fluoro-1-methoxy-2-(1,1,1-trifluoropropan-2-yl)benzene (C43). 4-Fluoro-1-methoxy-2-(3,3,3-trifluoroprop-1-en-2-yl)benzene (C42) (82 g, 370 mmol) was split into four batches; each batch was dissolved in methanol (200 mL), treated with 10% palladium on carbon (1 g, 10 mmol) and hydrogenated at 50 psi for 15 minutes. After careful filtration through Celite and rinsing of the filter pad with methanol, the four filtrates were combined and concentrated in vacuo, keeping the bath temperature at <25° C. The residue was dissolved in dichloromethane, filtered through Celite, and concentrated under reduced pressure, providing the product as a light yellow oil. Yield: 71.0 g, 320 mmol, 86%. $^1$H NMR (400 MHz, CDCl$_3$) η1.42 (d, J=7.2 Hz, 3H), 3.83 (s, 3H), 4.06-4.19 (m, 1H), 6.84 (dd, J=9.0. 4.5 Hz, 1H), 6.98 (ddd, J=9.0, 7.8, 3.1 Hz, 1H), 7.06-7.11 (m, 1H).

Step 3. Synthesis of 4-fluoro-2-(1,1,1-trifluoropropan-2-yl)phenol (C44). Boron tribromide (19.1 mL, 198 mmol) was added to a −78° C. solution of 4-fluoro-1-methoxy-2-(1,1,1-trifluoropropan-2-yl)benzene (C43) (20.0 g, 90.0 mmol) in dichloromethane (400 mL). The cooling bath was removed and the reaction mixture was allowed to warm to room temperature over 66 hours. It was then cooled in an ice bath and treated drop-wise with water (50 mL) while venting into an aqueous potassium carbonate trap. When the vigorous reaction had subsided, additional water (300 mL) was added, and the mixture was stirred until all the solids had dissolved. The aqueous layer was extracted with dichloromethane (200 mL), and the combined organic layers were dried over magnesium sulfate, filtered, and concentrated under reduced pressure, while keeping the water bath between 23° C. and 35° C. The product was obtained as an oil, which contained some impurities by $^1$H NMR assessment; this was used without additional purification. Yield: 20.6 g, assumed quantitative. $^1$H NMR (400 MHz, CDCl$_3$), product peaks only: δ 1.45 (d, J=7.4 Hz, 3H), 3.98-4.12 (m, 1H), 6.74 (dd, J=8.8, 4.5 Hz, 1H), 6.85-6.91 (m, 1H), 7.04-7.09 (m, 1H).

Step 4. Synthesis of (2S)-1-[4-fluoro-2-(1,1,1-trifluoropropan-2-yl)phenoxy]propan-2-amine (P13). Cesium carbonate (28.6 g, 87.8 mmol) was added to a solution of crude 4-fluoro-2-(1,1,1-trifluoropropan-2-yl)phenol (C44) (6.00 g, 28.8 mmol) in N,N-dimethylformamide (60 mL). After addition of (2S)-2-[(tert-butoxycarbonyl)amino]propyl methanesulfonate (P12) (7.5 g, 29.6 mmol), the reaction mixture was heated in a 60° C. oil bath for 30 minutes, then treated with additional P12 (7.5 g, 29.6 mmol) and heated for 18 hours. At this point, the reaction mixture was allowed to cool to room temperature, diluted with water (500 mL), and extracted with diethyl ether (3×150 mL). The combined organic layers were dried over magnesium sulfate, filtered, and concentrated under reduced pressure. The resulting material (11.23 g) was dissolved in dichloromethane (200 mL); trifluoroacetic acid (40 mL) was added, and the reaction mixture was stirred for 1 hour. After removal of solvents in vacuo, the residue was dissolved in ethyl acetate and washed with saturated aqueous sodium bicarbonate solution and with saturated aqueous sodium chloride solution, dried over magnesium sulfate, filtered, and concentrated in vacuo. Purification using silica gel chromatography (Eluents: 75% ethyl acetate in heptane, then ethyl acetate, then 10% methanol in ethyl acetate) afforded the product as a roughly 1:1 mixture of two diastereomers, as assessed by $^1$H NMR. Yield: 5.44 g, 20.5 mmol, 71%. LCMS m/z 266.1 (M+1). $^1$H NMR (400 MHz, CDCl$_3$) δ [1.31 (d, J=6.6 Hz) and 1.32 (d, J=6.6 Hz), total 3H], 1.41 (d, J=7.2 Hz, 3H), 3.50-3.59 (m, 1H), 3.82-4.22 (m, 3H), 6.79-6.84 (m, 1H), 6.92-6.98 (m, 1H), 7.05-7.11 (m, 1H). Also obtained was material enriched in the higher R$_f$ diastereomer (1.10 g, 4.15 mmol, 14%) and material enriched in the lower R$_f$ diastereomer (324 mg, 1.22 mmol, 4%).

Preparation 14

7-(4-Methyl-1H-imidazol-1-yl)-3,4-dihydropyrido[2,1-c][1,4]oxazine-1,6-dione (P14)

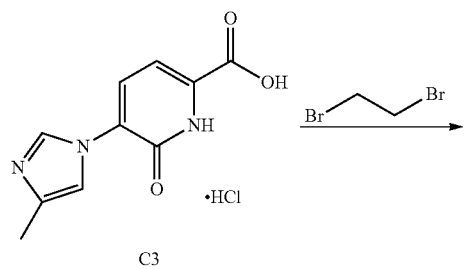

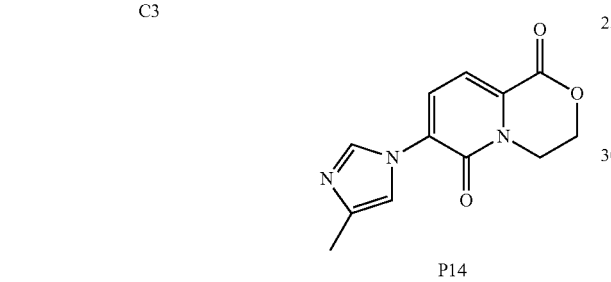

N,N-Dimethylformamide (850 mL) was added to a mixture of 5-(4-methyl-1H-imidazol-1-yl)-6-oxo-1,6-dihydropyridine-2-carboxylic acid hydrochloride salt (C3) (65 g, 250 mmol), 1,2-dibromoethane (52.5 g, 280 mmol) and cesium carbonate (124 g, 381 mmol), and the reaction mixture was heated to 90° C. for 6 hours. After allowing the reaction to cool to room temperature, the mixture was filtered through Celite, and the filtrate was concentrated in vacuo. The residue was dissolved in dichloromethane (500 mL), washed with saturated aqueous sodium chloride solution (100 mL), washed with water (50 mL), dried over magnesium sulfate, filtered, and concentrated under reduced pressure. The resulting solid was washed with acetonitrile to provide the product. Yield: 46.5 g, 190 mmol, 76%. $^1$H NMR (400 MHz, CDCl$_3$) δ 2.30 (d, J=0.8 Hz, 3H), 4.38-4.42 (m, 2H), 4.66-4.70 (m, 2H), 7.15-7.17 (m, 1H), 7.43 (AB quartet, J$_{AB}$=7.7 Hz, Δν$_{AB}$=33.4 Hz, 2H), 8.33 (d, J=1.4 Hz, 1H).

Preparation 15

1-Fluoro-4-nitro-2-(pentafluoro-λ$^6$-sulfanyl)benzene (P15)

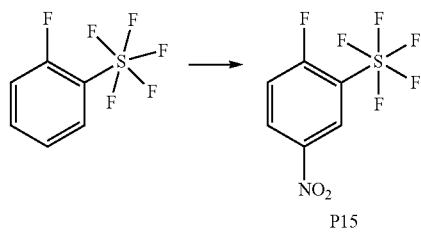

A mixture of 1-fluoro-2-(pentafluoro-λ$^6$-sulfanyl)benzene (2.00 g, 9.00 mmol) and sulfuric acid (4 mL) was cooled in an ice bath. Nitric acid (4 mL) was added to the reaction mixture; after 5 minutes, the cooling bath was removed and stirring was continued at room temperature for 3 hours. The reaction mixture was then poured into ice (150 mL), and the resulting mixture was extracted with diethyl ether (2×75 mL). The combined organic layers were washed with saturated aqueous sodium chloride solution, dried over magnesium sulfate, filtered, and concentrated in vacuo to provide an oil. After addition of a seed crystal, the product was obtained as a solid. Yield: 1.99 g, 7.45 mmol, 83%. $^1$H NMR (400 MHz, CDCl$_3$) δ 7.45 (br dd, J=10, 9 Hz, 1H), 8.46 (br ddd, J=9.1, 3, 3 Hz, 1H), 8.72 (dd, J=5.8, 2.7 Hz, 1H).

EXAMPLES

Example 1

2-{2-[4-Fluoro-2-(trifluoromethyl)phenoxy]ethyl}-7-(4-methyl-1H-imidazol-1-yl)-3,4-dihydro-2H-pyrido[1,2-a]pyrazine-1,6-dione (1)

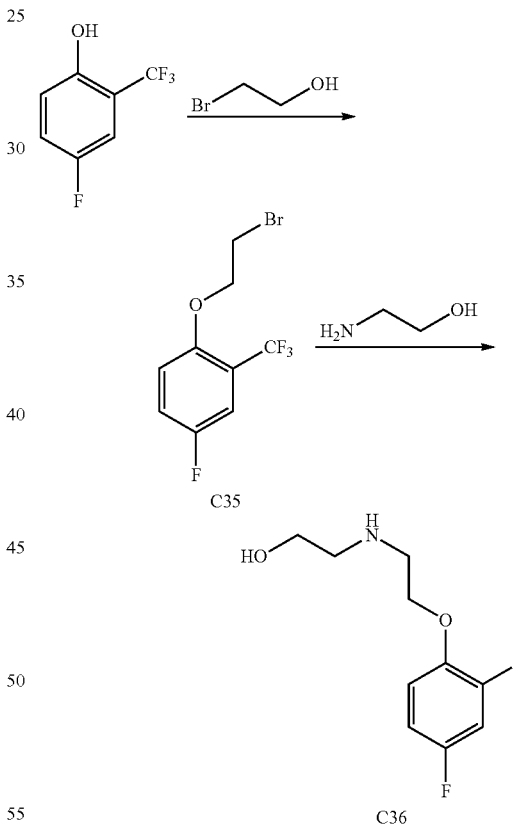

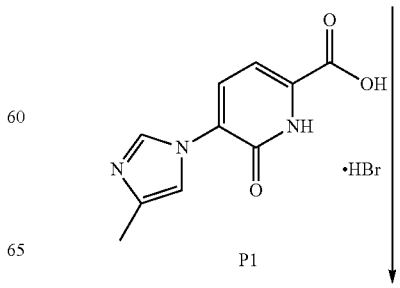

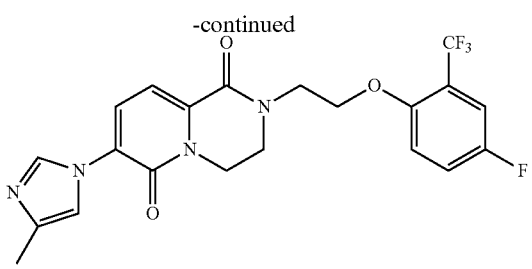

Step 1. Synthesis of 1-(2-bromoethoxy)-4-fluoro-2-(trifluoromethyl)benzene (C35). A mixture of 4-fluoro-2-(trifluoromethyl)phenol (1.05 g, 5.83 mmol), 2-bromoethanol (0.62 mL, 8.7 mmol) and triphenylphosphine (2.29 g, 8.73 mmol) in tetrahydrofuran (20 mL) was stirred for 5 minutes. Diisopropyl azodicarboxylate (94%, 1.84 mL, 8.71 mmol) was then added drop-wise over 20 minutes, and the reaction was stirred at room temperature for 16 hours. Water (50 mL) was added, and the mixture was extracted with dichloromethane (2×75 mL). The combined organic layers were washed with saturated aqueous sodium chloride solution (50 mL), dried over magnesium sulfate, and concentrated in vacuo. Purification via silica gel chromatography (Gradient: 0% to 10% ethyl acetate in heptane) afforded the title compound as a white solid. Yield: 600 mg, 2.09 mmol, 36%. GCMS m/z 286. $^1$H NMR (400 MHz, CDCl$_3$) δ 3.66 (dd, J=6.6, 6.4 Hz, 2H), 4.35 (dd, J=6.5, 6.4 Hz, 2H), 6.97 (br dd, J=9.0, 4.1 Hz, 1H), 7.18-7.24 (m, 1H), 7.32 (br dd, J=8.3, 3.2 Hz, 1H).

Step 2. Synthesis of 2-({2-[4-fluoro-2-(trifluoromethyl)phenoxy]ethyl}amino)ethanol (C36). A mixture of 1-(2-bromoethoxy)-4-fluoro-2-(trifluoromethyl)benzene (C35) (600 mg, 2.09 mmol) and 2-aminoethanol (2.20 mL, 52.4 mmol) was heated to 80° C. for 1.5 hours. The reaction was allowed to cool to room temperature, diluted with ethyl acetate (75 mL) and washed with aqueous sodium hydroxide solution (1 N, 4×50 mL). The organic layer was dried over magnesium sulfate and concentrated under reduced pressure to provide the title compound as a white solid. Yield: 550 mg, 2.06 mmol, 99%. LCMS m/z 268.1 (M+1). $^1$H NMR (400 MHz, CD$_3$OD) δ 2.80 (br dd, J=5.5, 5.4 Hz, 2H), 3.04 (dd, J=5.4, 5.2 Hz, 2H), 3.68 (br dd, J=5.6, 5.4 Hz, 2H), 4.20 (dd, J=5.3, 5.3 Hz, 2H), 7.22 (br dd, J=8.8, 4.2 Hz, 1H), 7.30-7.37 (m, 2H).

Step 3. Synthesis of 2-{2-[4-fluoro-2-(trifluoromethyl)phenoxy]ethyl}-7-(4-methyl-1H-imidazol-1-yl)-3,4-dihydro-2H-pyrido[1,2-a]pyrazine-1,6-dione (1). 5-(4-Methyl-1H-imidazol-1-yl)-6-oxo-1,6-dihydropyridine-2-carboxylic acid, 0.7 hydrobromide salt (P1) (201 mg, 0.729 mmol) and 2-({2-[4-fluoro-2-(trifluoromethyl)phenoxy]ethyl}amino)ethanol (C36) (214 mg, 0.801 mmol) were combined with dichloromethane (15 mL) and N,N-diisopropylethylamine (0.508 mL, 2.92 mmol), and the mixture was stirred for 5 minutes at room temperature. O-(7-Azabenzotriazol-1-yl)-N,N,N',N'-tetramethyluronium hexafluorophosphate (HATU, 97%, 857 mg, 2.19 mmol) was added in one portion, and the reaction was stirred for an additional 16 hours. Water (50 mL) was added, and the mixture was extracted with dichloromethane (3×50 mL). The combined organic layers were washed sequentially with saturated aqueous sodium bicarbonate solution (50 mL), water (50 mL) and saturated aqueous sodium chloride solution (50 mL), then dried over magnesium sulfate and concentrated in vacuo. Purification was carried out twice using silica gel chromatography (Gradient #1: 0% to 20% methanol in dichloromethane; Gradient #2: 0% to 70% [10% 2 N ammonia in methanol/90% ethyl acetate] in ethyl acetate) to afford the title compound as a white solid. Yield: 268 mg, 0.595 mmol, 82%. LCMS m/z 451.0 (M+1). $^1$H NMR (400 MHz, CD$_3$OD) δ 2.24 (d, J=0.9 Hz, 3H), 3.90-3.95 (m, 2H), 4.01 (dd, J=5.1, 5.1 Hz, 2H), 4.32-4.37 (m, 4H), 7.21-7.26 (m, 1H), 7.25 (d, J=7.8 Hz, 1H), 7.30-7.32 (m, 1H), 7.32-7.39 (m, 2H), 7.76 (d, J=7.8 Hz, 1H), 8.30 (d, J=1.3 Hz, 1H).

Example 2

2-{2-[(7-Fluoronaphthalen-1-yl)oxy]ethyl}-7-(2-methyl-1,3-oxazol-5-yl)-3,4-dihydro-2H-pyrido[1,2-a]pyrazine-1,6-dione (2)

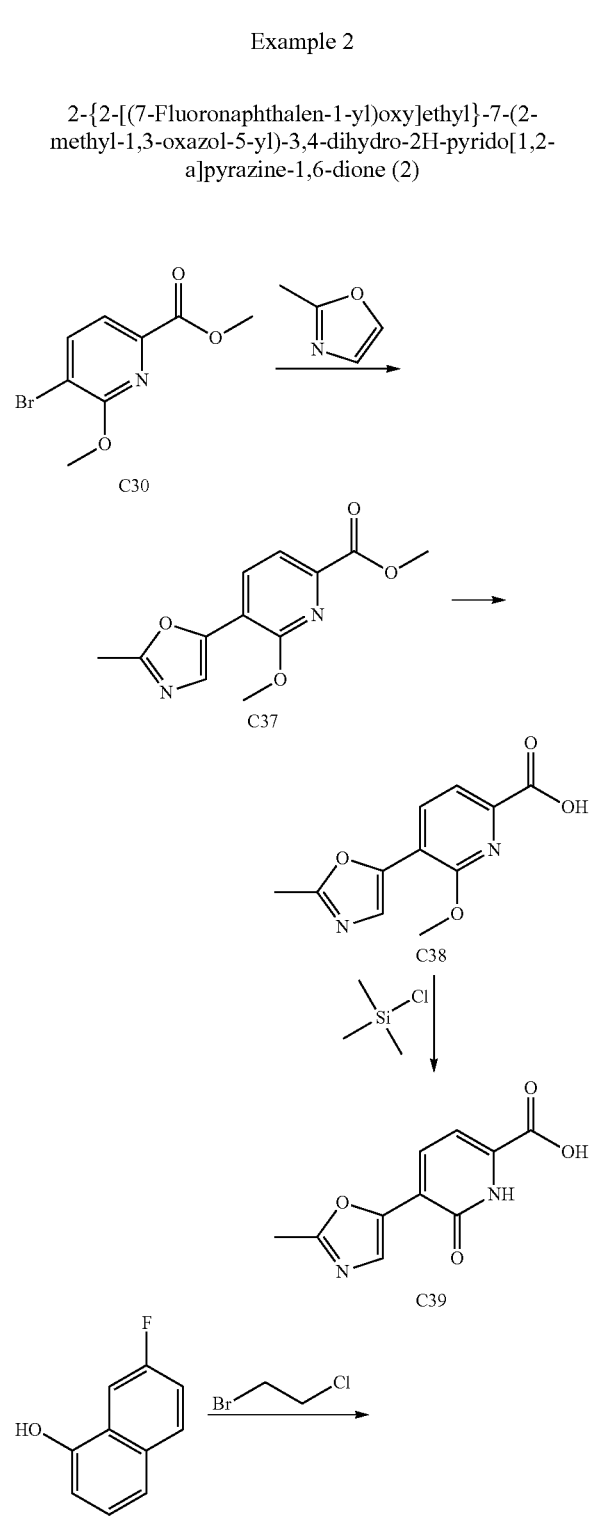

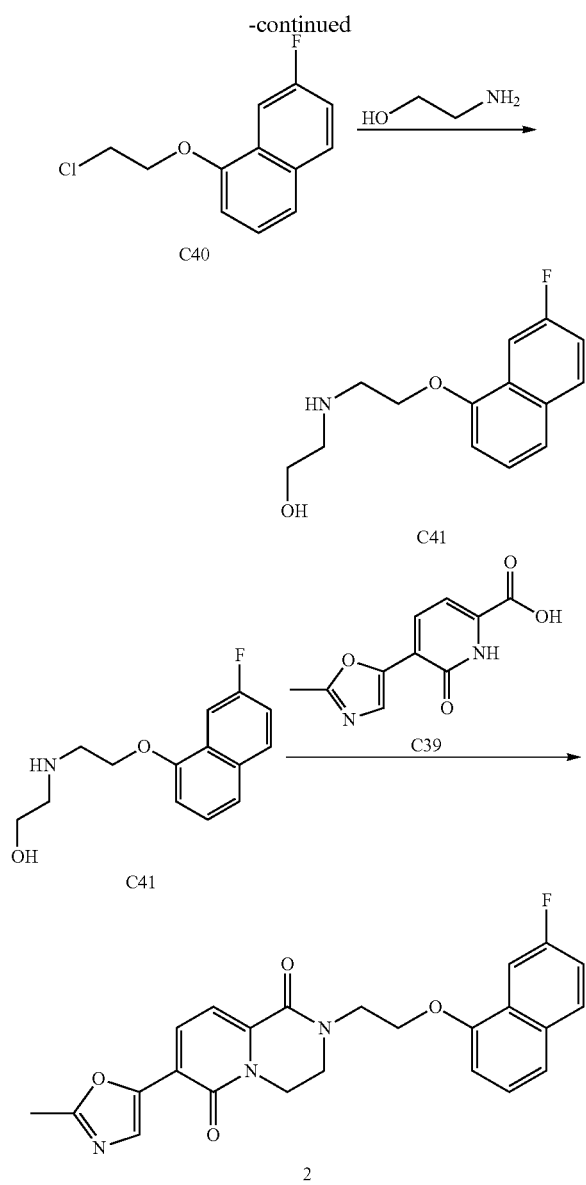

Step 1: Synthesis of 5-(2-methyl-1,3-oxazol-5-yl)-6-oxo-1,6-dihydropyridine-2-carboxylic acid (C39).

A. Synthesis of methyl 6-methoxy-5-(2-methyl-1,3-oxazol-5-yl)pyridine-2-carboxylate (C37). A mixture of 2-methyl-1,3-oxazole (2.41 g, 29.0 mmol), methyl 5-bromo-6-methoxypyridine-2-carboxylate (C30) (1.51 g, 5.81 mmol), potassium carbonate (finely ground, 2.41 g, 17.4 mmol), and allylpalladium chloride dimer (224 mg, 0.58 mmol) in 1,4-dioxane (11.6 mL) was heated to 100° C. overnight. The mixture was filtered through Celite, and the Celite pad was washed with ethyl acetate followed by ethanol. The combined filtrate and washings were concentrated in vacuo. Purification via silica gel chromatography (Gradient: 10% to 100% ethyl acetate in heptanes) afforded the title compound as a solid. Yield: 267 mg, 1.02 mmol, 18%. $^1$H NMR (400 MHz, CD$_3$OD) δ 1.42 (t, J=7.1 Hz, 3H), 2.56 (s, 3H), 4.17 (s, 3H), 4.43 (q, J=7.1 Hz, 2H), 7.59 (s, 1H), 7.83 (d, J=7.8 Hz, 1H), 8.17 (d, J=7.7 Hz, 1H).

B. Synthesis of 6-methoxy-5-(2-methyl-1,3-oxazol-5-yl)pyridine-2-carboxylic acid (C38). To a mixture of methyl 6-methoxy-5-(2-methyl-1,3-oxazol-5-yl)pyridine-2-carboxylate (C37) (217 mg, 0.87 mmol) in tetrahydrofuran (8.7 mL) and water (2.0 mL) was added lithium hydroxide (62.8 mg, 2.62 mmol) and the reaction was stirred at room temperature for 18 hours. To the mixture was added additional lithium hydroxide (62.8 mg, 2.62 mmol) and Amberlite IRC-50 ion-exchange resin. The mixture was filtered, concentrated in vacuo, and azeotroped three times with toluene to afford the title compound as a solid. Yield: 173 mg, 0.74 mmol, 85%. LCMS m/z 235.2 (M+1). $^1$H NMR (400 MHz, CD$_3$OD) δ 2.54 (s, 3H), 4.18 (s, 3H), 7.48 (s, 1H), 7.70 (d, J=7.6 Hz, 1H), 8.07 (d, J=7.7 Hz, 1H).

C. Synthesis of 5-(2-methyl-1,3-oxazol-5-yl)-6-oxo-1,6-dihydropyridine-2-carboxylic acid (C39). To a solution of 6-methoxy-5-(2-methyl-1,3-oxazol-5-yl)pyridine-2-carboxylic acid (C38) (173 mg, 0.74 mmol) in anhydrous acetonitrile (8.2 mL) at 0° C. was added sodium iodide (177 mg, 1.18 mmol) and trimethylsilyl chloride (149 μL, 1.18 mmol). The mixture was warmed to room temperature, then heated at reflux for 18 hours. The reaction was quenched with methanol, concentrated in vacuo, and treated with hydrogen chloride (4 M in 1,4-dioxane) and pentane. The mixture was filtered to afford the title compound as a solid. Yield: 90 mg, 0.41 mmol, 55%. LCMS m/z 221.2 (M+1).

Step 2: Synthesis of 2-({2-[(7-fluoronaphthalen-1-yl)oxy]ethyl}amino)ethanol (C41).

A. Synthesis of 1-(2-chloroethoxy)-7-fluoronaphthalene (C40). To a solution of 7-fluoronaphthalen-1-ol (500 mg, 3.08 mmol) in methyl ethyl ketone (7.71 mL) was added potassium carbonate (682 mg, 4.93 mmol) and 1-bromo-2-chloroethane (1.46 mL, 17.0 mmol). The reaction was heated at reflux for 18 hours, whereupon it was allowed to cool to room temperature. Saturated aqueous potassium carbonate solution was added, and the mixture was extracted three times with ethyl acetate. The combined organic layers were dried over sodium sulfate and concentrated in vacuo. Purification via silica gel chromatography (Gradient: 10% to 50% ethyl acetate in heptanes) afforded the title compound as an oil. Yield: 429 mg, 1.59 mmol, 52%. $^1$H NMR (400 MHz, CDCl$_3$) δ 3.79 (t, J=6.2 Hz, 2H), 4.48 (t, J=6.2 Hz, 2H), 6.84 (d, J=7.6 Hz, 1H), 7.28 (ddd, J=8.9, 8.4, 2.7 Hz, 1H), 7.34 (br dd, J=8.2, 7.7 Hz, 1H), 7.47 (br d, J=8.3 Hz, 1H), 7.80 (dd, J=9.0, 5.7 Hz, 1H), 7.91 (br dd, J=10.6, 2.6 Hz, 1H).

B. Synthesis of 2-({2-[(7-fluoronaphthalen-1-yl)oxy]ethyl}amino)ethanol (C41). A solution of 1-(2-chloroethoxy)-7-fluoronaphthalene (C40) (429 mg, 1.59 mmol) in N,N-dimethylformamide (8.9 mL) was treated with 2-aminoethanol (1.03 mL, 18.6 mmol) and heated to 80° C. for 18 hours. The reaction was cooled to room temperature, treated with saturated aqueous sodium bicarbonate solution (100 mL) and extracted with ethyl acetate (3×75 mL). The combined organic layers were washed with aqueous sodium hydroxide (1 M), dried over sodium sulfate and concentrated in vacuo. Purification via silica gel chromatography afforded the title compound as a colorless solid. Yield: 194 mg, 0.77 mmol, 48%. $^1$H NMR (400 MHz, CDCl$_3$) δ 2.92-2.97 (m, 2H), 3.19 (dd, J=5.3, 5.1 Hz, 2H), 3.69-3.73 (m, 2H), 4.27 (dd, J=5.3, 5.1 Hz, 2H), 6.87 (d, J=7.6 Hz, 1H), 7.25-7.30 (m, 1H, assumed; partially obscured by solvent peak), 7.34 (dd, J=8.1, 7.7 Hz, 1H), 7.44 (d, J=8.2 Hz, 1H), 7.80 (dd, J=9.1, 5.6 Hz, 1H), 7.85 (dd, J=10.5, 2.5 Hz, 1H).

Step 3: Synthesis of 2-{2-[(7-fluoronaphthalen-1-yl)oxy]ethyl}-7-(2-methyl-1,3-oxazol-5-yl)-3,4-dihydro-2H-pyrido[1,2-a]pyrazine-1,6-dione (2). 5-(2-Methyl-1,3-oxazol-5-yl)-6-oxo-1,6-dihydropyridine-2-carboxylic acid (C39) (45 mg, 0.20 mmol) and 2-({2-[(7-fluoronaphthalen-1-yl)oxy]ethyl}amino)ethanol (C41) (55.8 mg, 1.1 mmol) were combined with dichloromethane (4 mL) and N,N-diisopropylethylamine (178 μL, 1.02 mmol). O-(7-Azabenzotriazol-1- yl)-N,N,N',N'-tetramethyluronium hexafluorophosphate (HATU, 97%, 171 mg, 0.45 mmol) was added, and the reaction was stirred at room temperature for 18 hours. Saturated aqueous sodium bicarbonate solution was added and the mixture was extracted three times with ethyl acetate. The combined organic layers were dried over sodium sulfate and concentrated in vacuo. Purification via silica gel chromatography (Gradient: 50% to 100% ethyl acetate in heptane, followed by elution with 20% methanol in ethyl acetate) was followed by high-pressure liquid chromatographic purification (Silica column, 5 μm; Gradient: 5% to 100% ethanol in heptane), to afford the title compound as a solid. Yield: 10 mg, 0.022 mmol, 11%. LCMS m/z 434.5 (M+1). $^1$H NMR (400 MHz, CDCl$_3$) δ 2.64 (s, 3H), 3.97-4.02 (m, 2H), 4.12-4.16 (m, 2H), 4.39-4.47 (m, 4H), 6.85 (d, J=7.6 Hz, 1H), 7.26-7.31 (m, 1H, assumed; partially obscured by solvent peak), 7.31-7.36 (m, 2H), 7.46 (d, J=8.2 Hz, 1H), 7.71 (dd, J=10.3, 2.5 Hz, 1H), 7.81 (dd, J=9.0, 5.5 Hz, 1H), 7.89 (d, J=7.6 Hz, 1H), 8.00 (s, 1H).

Example 117

2-{(2S)-1-[4-Chloro-2-(1,1,1-trifluoro-2-methylpropan-2-yl)phenoxy]propan-2-yl}-7-(4-methyl-1H-imidazol-1-yl)-3,4-dihydro-2H-pyrido[1,2-a]pyrazine-1,6-dione (117)

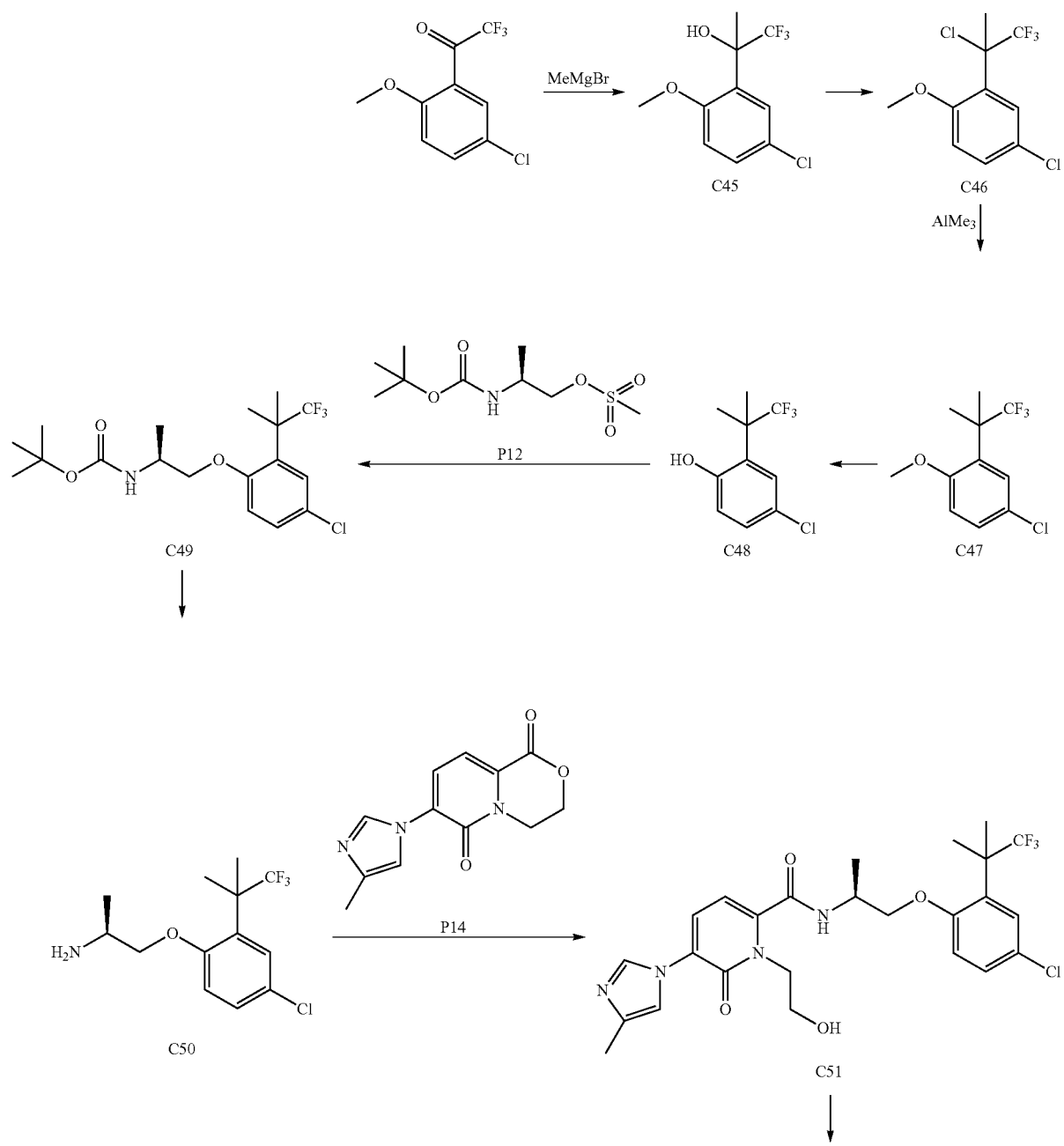

-continued

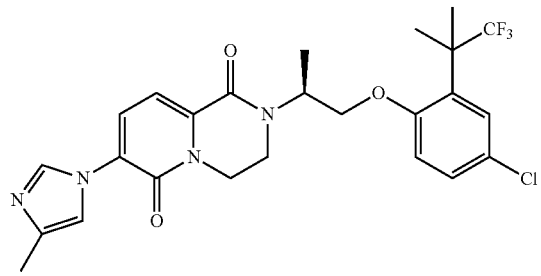

117

Step 1. Synthesis of 2-(5-chloro-2-methoxyphenyl)-1,1,1-trifluoropropan-2-ol (C45). A solution of 1-(5-chloro-2-methoxyphenyl)-2,2,2-trifluoroethanone (3.00 g, 12.6 mmol) in tetrahydrofuran (30 mL) was cooled to −78° C. Methylmagnesium bromide (3 M in diethyl ether, 6.29 mL, 18.9 mmol) was added drop-wise over a period of 10 minutes, and the mixture was warmed to 0° C. and stirred at that temperature for 30 minutes. After the reaction had been quenched by addition of saturated aqueous ammonium chloride solution (10 mL) over a period of 5 minutes, water (50 mL) was added, and the resulting mixture was extracted with dichloromethane (3×50 mL). The combined organic layers were dried over magnesium sulfate, filtered, and concentrated in vacuo to provide the product as a colorless oil containing residual tetrahydrofuran (the molar ratio of product:tetrahydrofuran was 2:1), which was taken to the following step without further purification. Corrected yield: 2.77 g, 10.9 mmol, 86%. GCMS m/z 254 (M+). $^1$H NMR (400 MHz, CDCl$_3$) δ 1.76 (br s, 3H), 3.94 (s, 3H), 5.88 (br s, 1H), 6.94 (d, J=8.8 Hz, 1H), 7.30-7.35 (m, 2H).

Step 2. Synthesis of 4-chloro-2-(2-chloro-1,1,1-trifluoropropan-2-yl)-1-methoxybenzene (C46). 2-(5-Chloro-2-methoxyphenyl)-1,1,1-trifluoropropan-2-ol (C45) (1.20 g, 4.71 mmol) was treated with thionyl chloride (4 mL, 50 mmol), followed by pyridine (19.1 μL, 0.236 mmol). The reaction mixture was heated at 40° C. for 16 hours, then poured into a mixture of ice and saturated aqueous sodium bicarbonate solution. The resulting mixture was extracted with dichloromethane (3×50 mL), and the combined organic layers were dried over magnesium sulfate, filtered, and concentrated under reduced pressure. The residue was determined by $^1$H NMR to be a mixture of product and an alkene side-product derived from elimination, in a roughly 4:1 ratio; this was used in the following step without additional purification. GCMS m/z 272 (M+). $^1$H NMR (400 MHz, CDCl$_3$), product peaks only: δ 2.27 (br s, 3H), 3.86 (s, 3H), 6.90 (d, J=8.8 Hz, 1H), 7.33 (dd, J=8.8, 2.5 Hz, 1H), 7.69-7.73 (m, 1H).

Step 3. Synthesis of 4-chloro-1-methoxy-2-(1,1,1-trifluoro-2-methylpropan-2-yl)benzene (C47). A solution of 4-chloro-2-(2-chloro-1,1,1-trifluoropropan-2-yl)-1-methoxybenzene (C46) (derived from the preceding step, <4.71 mmol) in dichloromethane (30 mL) was cooled to −78° C. Trimethylaluminum (2 M in hexanes, 7.32 mL, 14.6 mmol) was then added drop-wise over a period of 10 minutes, and the reaction mixture was stirred at −78° C. for 30 minutes. It was then allowed to warm to room temperature and stirred for 16 hours, at which time it was cooled to −78° C. and quenched with water (10 mL). The reaction mixture was filtered through Celite, and the filter pad was washed with dichloromethane; the combined filtrates were washed with saturated aqueous sodium chloride solution, concentrated in vacuo, and purified using silica gel chromatography (Eluant: hexanes) to afford the product as a colorless oil. Yield: 746 mg, 2.95 mmol, 63% over 2 steps. $^1$H NMR (400 MHz, CDCl$_3$), characteristic peaks: δ 3.83 (s, 3H), 6.86 (d, J=8.8 Hz, 1H), 7.25 (dd, J=8.8, 2.6 Hz, 1H), 7.35-7.37 (m, 1H).

Step 4. Synthesis of 4-chloro-2-(1,1,1-trifluoro-2-methylpropan-2-yl)phenol (C48). Boron tribromide (1 M in dichloromethane, 16.8 mL, 16.8 mmol) was added drop-wise over 10 minutes to a −78° C. solution of 4-chloro-1-methoxy-2-(1,1,1-trifluoro-2-methylpropan-2-yl)benzene (C47) (850 mg, 3.36 mmol) in dichloromethane (10 mL). After stirring at −78° C. for 30 minutes, the reaction mixture was heated to 40° C. and held at that temperature for 24 hours. The reaction mixture was then cooled to −78° C. and quenched with saturated aqueous sodium bicarbonate solution (10 mL). The pH was adjusted to approximately 5 with aqueous hydrochloric acid, and the mixture was extracted with dichloromethane (3×50 mL). The combined organic layers were dried over magnesium sulfate, filtered, and concentrated in vacuo. Purification using silica gel chromatography (Gradient: 0% to 20% ethyl acetate in heptane) afforded the product as a colorless oil. Yield: 515 mg, 2.16 mmol, 64%. GCMS m/z 238 (M+). $^1$H NMR (400 MHz, CDCl$_3$) 1.67 (br s, 6H), 5.37 (br s, 1H), 6.71 (d, J=8.6 Hz, 1H), 7.14 (dd, J=8.6, 2.5 Hz, 1H), 7.33-7.36 (m, 1H).

Step 5. Synthesis of tert-butyl{(2S)-1-[4-chloro-2-(1,1,1-trifluoro-2-methylpropan-2-yl)phenoxy]propan-2-yl}carbamate (C49). Cesium carbonate (2.05 g, 6.28 mmol) was added to a solution of 4-chloro-2-(1,1,1-trifluoro-2-methylpropan-2-yl)phenol (C48) (500 mg, 2.10 mmol) in N,N-dimethylformamide (5 mL). (2S)-2-[(tert-Butoxycarbonyl)amino]propyl methanesulfonate (P12) (0.53 g, 2.1 mmol) was added, and the reaction mixture was heated to 60° C. After 30 minutes, additional P12 (0.53 g, 2.1 mmol) was added, and heating was continued for 18 hours. Water (100 mL) was added, and the mixture was extracted with diethyl ether (3×50 mL). The combined organic layers were dried over magnesium sulfate, filtered, and concentrated under reduced pressure. Silica gel chromatography (Gradient: 0% to 15% ethyl acetate in heptane) afforded the product as a colorless oil. Yield: 625 mg, 1.58 mmol, 75%.

Step 6. Synthesis of (2S)-1-[4-chloro-2-(1,1,1-trifluoro-2-methylpropan-2-yl)phenoxy]propan-2-amine (C50). Trifluoroacetic acid (5 mL) was added to a solution of tert-butyl{(2S)-1-[4-chloro-2-(1,1,1-trifluoro-2-methylpropan-2-yl)phenoxy]propan-2-yl}carbamate (C49) (600 mg, 1.52 mmol) in dichloromethane (24 mL), and the reaction mixture was stirred for 30 minutes. Aqueous sodium hydroxide solution (1 M, 50 mL) was added, and the mixture was extracted with diethyl ether (3×50 mL). The combined organic layers were dried over magnesium sulfate, filtered, and concentrated in vacuo to afford the product as a light amber oil, which was used without further purification. Yield: 433 mg, 1.46 mmol, 96%. LCMS m/z 296.1, 298.1 (M+1). ¹H NMR (400 MHz, CDCl₃) δ 1.24 (d, J=6.4 Hz, 3H), 1.67 (br s, 6H), 2.13 (br s, 2H), 3.41-3.50 (m, 1H), 3.79 (dd, half of ABX pattern, J=8.8, 7.2 Hz, 1H), 3.86 (dd, half of ABX pattern, J=8.9, 4.4 Hz, 1H), 6.86 (d, J=8.8 Hz, 1H), 7.23 (dd, J=8.8, 2.5 Hz, 1H), 7.36-7.39 (m, 1H).

Step 7. Synthesis of N-{(2S)-1-K-chloro-2-(1,1,1-trifluoro-2-methylpropan-2-yl)phenoxy]propan-2-yl}-1-(2-hydroxyethyl)-5-(4-methyl-1H-imidazol-1-yl)-6-oxo-1,6-dihydropyridine-2-carboxamide (C51). Bis(trimethylaluminum)-1,4-diazabicyclo[2.2.2]octane adduct (97%, 398 mg, 1.51 mmol) was added portion-wise over 5 minutes to a solution of (2S)-1-[4-chloro-2-(1,1,1-trifluoro-2-methylpropan-2-yl)phenoxy]propan-2-amine (C50) (400 mg, 1.51 mmol) in tetrahydrofuran (8 mL), and the reaction mixture was heated to 40° C. for 45 minutes. 7-(4-Methyl-1H-imidazol-1-yl)-3,4-dihydropyrido[2,1-c][1,4]oxazine-1,6-dione (P14) (555 mg, 2.26 mmol) was then added portion-wise over a period of approximately 5 minutes, and the reaction mixture was heated to 70° C. for 6 hours, whereupon it was cooled to 0° C. and slowly quenched with aqueous hydrochloric acid (1 M, 1 mL). After addition of water, the mixture was extracted three times with dichloromethane; the combined organic layers were dried over magnesium sulfate, filtered, and concentrated under reduced pressure to provide the product as a pale yellow solid, which was used in the next step without additional purification. Yield: 690 mg, 1.28 mmol, 85%. LCMS m/z 541.3, 543.0 (M+1). ¹H NMR (400 MHz, CD₃OD) δ 1.41 (d, J=6.8 Hz, 3H), 1.69 (br s, 6H), 2.23 (d, J=1.0 Hz, 3H), 3.85 (t, J=5.8 Hz, 2H), 4.05 (dd, half of ABX pattern, J=9.6, 5.4 Hz, 1H), 4.14 (dd, half of ABX pattern, J=9.6, 6.6 Hz, 1H), 4.41 (t, J=5.8 Hz, 2H), 4.48-4.57 (m, 1H), 6.54 (d, J=7.5 Hz, 1H), 7.10 (d, J=8.9 Hz, 1H), 7.24-7.26 (m, 1H), 7.31 (dd, J=8.8, 2.6 Hz, 1H), 7.37-7.40 (m, 1H), 7.67 (d, J=7.5 Hz, 1H), 8.19 (d, J=1.4 Hz, 1H).

Step 8. Synthesis of 2-{(2S)-1-[4-chloro-2-(1,1,1-trifluoro-2-methylpropan-2-yl)phenoxy]propan-2-yl}-7-(4-methyl-1H-imidazol-1-yl)-3,4-dihydro-2H-pyrido[1,2-a]pyrazine-1,6-dione (117). Diisopropyl azodicarboxylate (94%, 0.314 mL, 1.49 mmol) was added to a mixture of N-{(2S)-1-[4-chloro-2-(1,1,1-trifluoro-2-methylpropan-2-yl)phenoxy]propan-2-yl}-1-(2-hydroxyethyl)-5-(4-methyl-1H-imidazol-1-yl)-6-oxo-1,6-dihydropyridine-2-carboxamide (C51) (671 mg, 1.24 mmol) and triphenylphosphine (390 mg, 1.49 mmol) in tetrahydrofuran (30 mL), and the reaction mixture was allowed to stir at room temperature for 1 hour. After removal of solvent in vacuo, the residue was purified using silica gel chromatography (Gradient: 0% to 70% [10% (2 N ammonia in methanol)/90% ethyl acetate] in ethyl acetate), then via chiral HPLC (Column: Phenomenex Cellulose-1, 5 μm; Gradient: 5% to 100% ethanol in heptane), to afford the product as a pale yellow foam. Yield: 409 mg, 0.782 mmol, 63%. LCMS m/z 523.0, 525.0 (M+1). ¹H NMR (400 MHz, CDCl₃) δ 1.41 (d, J=7.0 Hz, 3H), 1.59-1.62 (m, 6H), 2.35 (d, J=1.0 Hz, 3H), 3.59-3.72 (m, 2H), 4.03 (dd, half of ABX pattern, J=10.0, 4.7 Hz, 1H), 4.11 (dd, half of ABX pattern, J=10.0, 8.9 Hz, 1H), 4.25 (ddd, J=14.2, 8.1, 4.4 Hz, 1H), 4.46 (ddd, J=14.3, 6.4, 4.3 Hz, 1H), 5.16-5.26 (m, 1H), 6.86 (d, J=8.8 Hz, 1H), 7.17-7.19 (m, 1H), 7.25 (dd, J=8.8, 2.5 Hz, 1H), 7.30 (d, J=7.8 Hz, 1H), 7.36 (br d, J=2.5 Hz, 1H), 7.54 (d, J=7.6 Hz, 1H), 8.48 (br s, 1H).

Example 118

2-[(2S)-1-{4-Fluoro-2-[(2R)-1,1,1-trifluoropropan-2-yl]phenoxy}propan-2-yl]-7-(4-methyl-1H-imidazol-1-yl)-3,4-dihydro-2H-pyrido[1,2-a]pyrazine-1,6-dione (118)

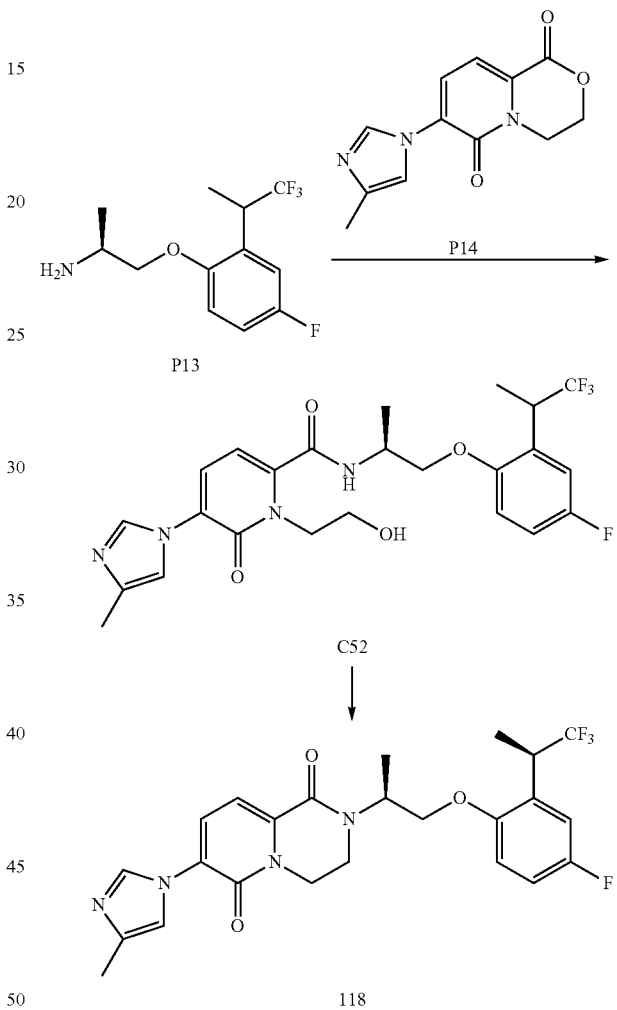

Step 1. Synthesis of N-{(2S)-1-[4-fluoro-2-(1,1,1-trifluoropropan-2-yl)phenoxy]propan-2-yl}-1-(2-hydroxyethyl)-5-(4-methyl-1H-imidazol-1-yl)-6-oxo-1,6-dihydropyridine-2-carboxamide (C52). Diisobutylaluminum hydride (1.5 M in toluene, 1.63 mL, 2.44 mmol) was added to a solution of (2S)-1-[4-fluoro-2-(1,1,1-trifluoropropan-2-yl)phenoxy]propan-2-amine (P13) (fractions that were enriched in the lower R_f diastereomer were used, see step 4 of Preparation 13; 324 mg, 1.22 mmol) in tetrahydrofuran (5 mL). After the vigorous bubbling subsided, the reaction mixture was stirred for 2 hours at room temperature. 7-(4-Methyl-1H-imidazol-1-yl)-3,4-dihydropyrido[2,1-c][1,4]oxazine-1,6-dione (P14) (299.7 mg, 1.222 mmol) was added, and the reaction mixture was heated to 60° C. for 24 hours. It was then cooled to room temperature, carefully quenched with 1 M aqueous sodium hydroxide solution, and extracted with ethyl acetate (2×30 mL). The combined organic layers were washed with saturated aqueous sodium chloride solution, dried over magnesium sulfate, filtered, and concentrated in vacuo to afford the product as a sticky orange-tan oil. This was used in the following step without additional purification. Yield: 430 mg, 0.84 mmol, 69%. LCMS m/z 511.3 (M+1). On large scale, use of diisobutylaluminum hydride was less successful; in this case, simply dissolving P13 and P14 in methanol, boiling the solution down to a thick homogeneous oil and heating at 110° C. provided superior results.

Step 2. Synthesis of 2-[(2S)-1-{4-fluoro-2-[(2R)-1,1,1-trifluoropropan-2-yl]phenoxy}propan-2-yl]-7-(4-methyl-1H-imidazol-1-yl)-3,4-dihydro-2H-pyrido[1,2-a]pyrazine-1,6-dione (118). Diisopropyl azodicarboxylate (94%, 0.229 mL, 1.09 mmol) was added to a solution of N-{(2S)-1-[4-fluoro-2-(1,1,1-trifluoropropan-2-yl)phenoxy]propan-2-yl}-1-(2-hydroxyethyl)-5-(4-methyl-1H-imidazol-1-yl)-6-oxo-1,6-dihydropyridine-2-carboxamide (C52) (430 mg, ≤0.84 mmol) and triphenylphosphine (98.5%, 291 mg, 1.09 mmol) in tetrahydrofuran (7 mL), and the reaction mixture was stirred at room temperature for 18 hours. It was then partitioned between water (20 mL) and ethyl acetate (30 mL), and the aqueous layer was extracted with ethyl acetate. The combined organic layers were washed with saturated aqueous sodium chloride solution, dried over magnesium sulfate, filtered, and concentrated under reduced pressure. Purification was carried out via silica gel chromatography (Eluents: ethyl acetate, then 10% methanol in ethyl acetate). Fractions containing the lowest $R_f$ spot were combined to afford a tan solid (200 mg), judged by NMR to consist of a mixture of the product diastereomers. $^1$H NMR (400 MHz, CD$_3$OD), characteristic peaks: δ 1.29-1.42 (m, 6H), 2.22-2.25 (m, 3H), 4.01-4.19 (m, 3H), 4.22-4.37 (m, 2H), 5.11-5.25 (m, 1H), 6.99-7.12 (m, 3H), 7.25-7.33 (m, 2H), 7.76-7.82 (m, 1H), 8.27-8.32 (m, 1H). This material was combined with the fractions containing the higher $R_f$ product diastereomer, as well as related material derived from starting material enriched in the upper $R_f$ diastereomer of P13 (see step 4 of Preparation 13; 1.10 g, 4.15 mmol) that had in similar fashion been subjected to the previous step and this Mitsunobu reaction [$^1$H NMR (400 MHz, CDCl$_3$), characteristic peaks: δ 1.38-1.49 (m, 6H), 2.32-2.35 (m, 3H), 6.79-6.85 (m, 1H), 6.95-7.01 (m, 1H), 7.03-7.11 (m, 1H), 7.15-7.19 (m, 1H), 7.29-7.34 (m, 1H), [7.52 (d, J=7.6 Hz) and 7.52 (d, J=7.8 Hz), total 1H], 8.40-8.45 (m, 1H)]. Purification of this mixture via supercritical fluid chromatography (Column: Chiral Technologies Chiralpak® AD-H, 5 μm; Eluent: 35:65 methanol/ carbon dioxide, containing 0.2% isopropylamine) provided material (150 mg) that was then slurried with diethyl ether (5 mL) and filtered to afford the product. Yield: 98 mg, 0.20 mmol, 4% over 2 steps. The stereochemistry of the methyl group adjacent to the trifluoromethyl moiety was established by single crystal X-ray crystallography on a sample prepared in a related manner. LCMS m/z 493.3 (M+1). $^1$H NMR (400 MHz, CD$_3$OD) δ 1.36-1.40 (m, 6H), 2.24 (d, J=1.2 Hz, 3H), 3.64 (ddd, J=13.6, 8.1, 4.2 Hz, 1H), 3.80 (ddd, J=13.6, 6.9, 4.1 Hz, 1H), 4.01-4.17 (m, 3H), 4.22-4.37 (m, 2H), 5.15-5.25 (m, 1H), 7.02-7.05 (m, 2H), 7.06-7.11 (m, 1H), 7.30 (d, J=7.8 Hz, 1H), 7.31-7.33 (m, 1H), 7.80 (d, J=7.8 Hz, 1H), 8.31 (d, J=1.2 Hz, 1H).

Example 119

2-{(2S)-1-[4-Chloro-2-(pentafluoro-λ$^6$-sulfanyl) phenoxy]propan-2-yl}-7-(4-methyl-1H-imidazol-1-yl)-3,4-dihydro-2H-pyrido[1,2-a]pyrazine-1,6-dione (119)

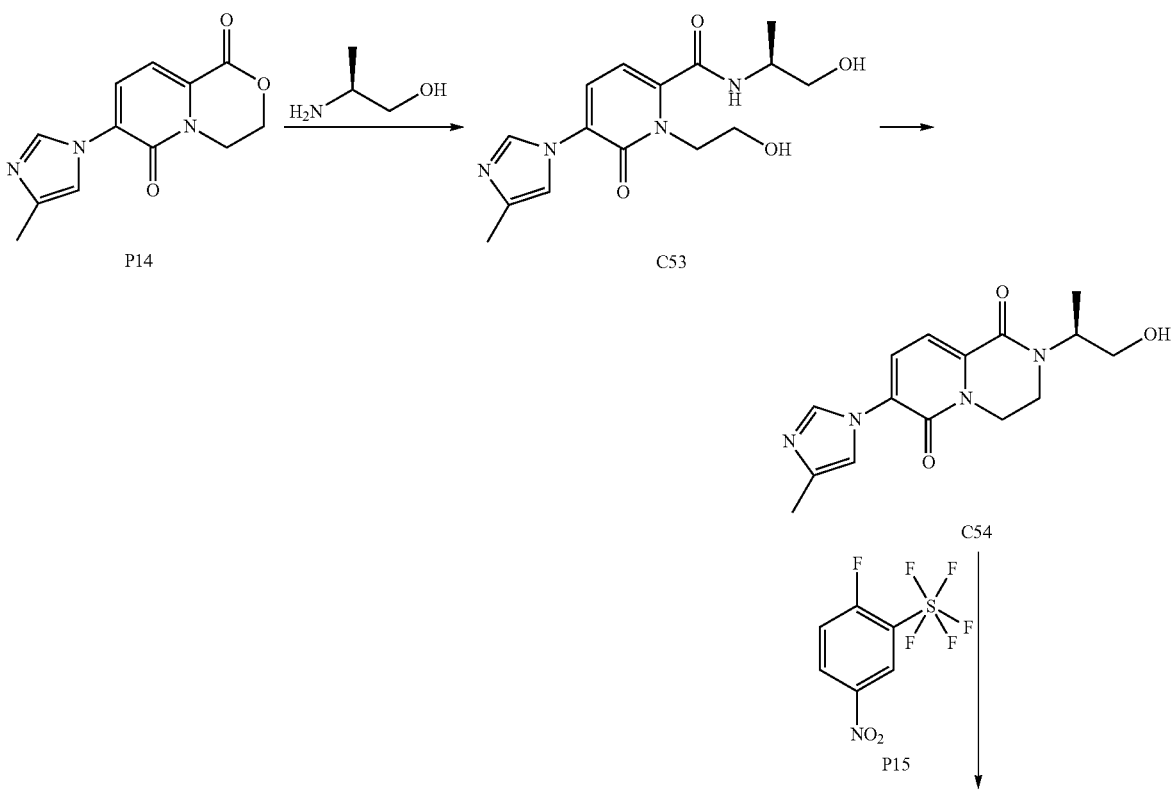

-continued

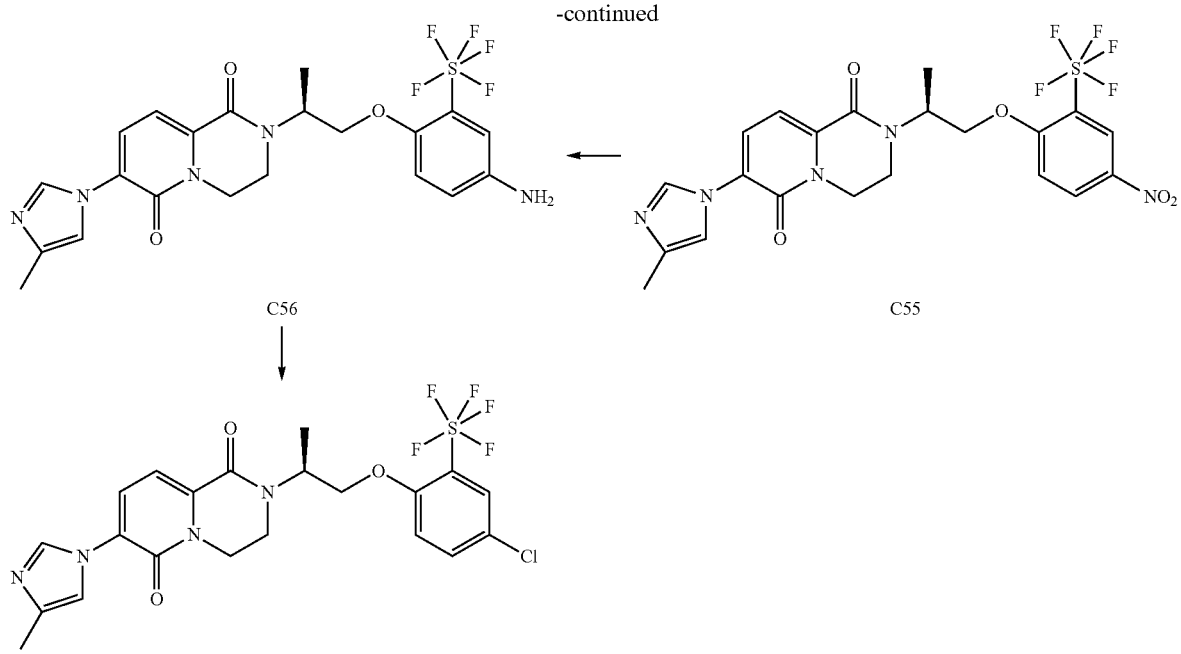

Step 1. Synthesis of 1-(2-hydroxyethyl)-N-[(2S)-1-hydroxypropan-2-yl]-5-(4-methyl-1H-imidazol-1-yl)-6-oxo-1,6-dihydropyridine-2-carboxamide (C53). A mixture of 7-(4-methyl-1H-imidazol-1-yl)-3,4-dihydropyrido[2,1-c][1,4]oxazine-1,6-dione (P14) (1.440 g, 5.872 mmol) and (2S)-2-aminopropan-1-ol (1.714 g, 22.82 mmol) in acetonitrile (3 mL) was heated to 85° C. for 20 minutes. The reaction mixture was then allowed to cool to room temperature and diluted with additional acetonitrile (10 mL). Filtration and rinsing with acetonitrile (10 mL) afforded the product as a white solid. Yield: 1.62 g, 5.06 mmol, 86%. $^1$H NMR (400 MHz, DMSO-$d_6$) δ 1.11 (d, J=6.8 Hz, 3H), 2.14 (d, J=0.9 Hz, 3H), 3.33-3.46 (m, 2H), 3.59-3.66 (m, 2H), 3.89-4.01 (m, 1H), 4.18-4.29 (m, 2H), 4.80 (t, J=5.8 Hz, 1H), 4.94 (t, J=5.4 Hz, 1H), 6.45 (d, J=7.5 Hz, 1H), 7.32-7.34 (m, 1H), 7.69 (d, J=7.5 Hz, 1H), 8.13 (d, J=1.3 Hz, 1H), 8.67 (br d, J=8.3 Hz, 1H).

Step 2. Synthesis of 2-[(2S)-1-hydroxypropan-2-yl]-7-(4-methyl-1H-imidazol-1-yl)-3,4-dihydro-2H-pyrido[1,2-a]pyrazine-1,6-dione (C54). Diisopropyl azodicarboxylate (95%, 2.58 mL, 12.7 mmol) was added drop-wise to a solution of 1-(2-hydroxyethyl)-N-[(2S)-1-hydroxypropan-2-yl]-5-(4-methyl-1H-imidazol-1-yl)-6-oxo-1,6-dihydropyridine-2-carboxamide (C53) (1.622 mg, 5.063 mmol) and triphenylphosphine (3.35 g, 12.7 mmol) in tetrahydrofuran (20 mL), and the reaction mixture was stirred at room temperature for 18 hours. The reaction mixture was concentrated onto silica gel and purified by silica gel chromatography (Eluents: ethyl acetate, followed by 5%, then 10%, then 25% methanol in ethyl acetate). Fractions containing the product were combined and concentrated in vacuo to near-dryness, then layered with ethyl acetate and allowed to stand. The resulting precipitate was collected by filtration to provide the product as a white solid. Yield: 446 mg, 1.48 mmol, 29%. $^1$H NMR (400 MHz, DMSO-$d_6$) δ 1.10 (d, J=6.9 Hz, 3H), 2.15 (d, J=1.0 Hz, 3H), 3.41-3.53 (m, 2H), 3.59-3.65 (m, 2H), 4.14-4.28 (m, 2H), 4.53-4.62 (m, 1H), 4.83 (t, J=5.7 Hz, 1H), 7.07 (d, J=7.7 Hz, 1H), 7.40-7.42 (m, 1H), 7.79 (d, J=7.8 Hz, 1H), 8.25 (d, J=1.4 Hz, 1H).

Step 3. Synthesis of 7-(4-methyl-1H-imidazol-1-yl)-2-{(2S)-1-[4-nitro-2-(pentafluoro-λ$^6$-sulfanyl)phenoxy]propan-2-yl}-3,4-dihydro-2H-pyrido[1,2-a]pyrazine-1,6-dione (C55). A solution of potassium tert-butoxide in tetrahydrofuran (1 M, 1.97 mL, 1.97 mmol) was added to a slurry of 2-[(2S)-1-hydroxypropan-2-yl]-7-(4-methyl-1H-imidazol-1-yl)-3,4-dihydro-2H-pyrido[1,2-a]pyrazine-1,6-dione (C54) (541 mg, 1.79 mmol) in tetrahydrofuran (6 mL), and the mixture was allowed to stir for 10 minutes. A solution of 1-fluoro-4-nitro-2-(pentafluoro-λ$^6$-sulfanyl)benzene (P15) (478 mg, 1.79 mmol) in tetrahydrofuran (4 mL) was added, and the reaction mixture was stirred at room temperature for 18 hours. At that point, it was diluted with water and extracted with ethyl acetate (3×50 mL). The combined organic layers were washed with saturated aqueous sodium chloride solution, dried over magnesium sulfate, filtered, and concentrated in vacuo. Purification via silica gel chromatography (Eluents: ethyl acetate, then 10% methanol in ethyl acetate) afforded the product as a yellow foam. Yield: 695 mg, 1.26 mmol, 70%. LCMS m/z 550.2 (M+1). $^1$H NMR (400 MHz, CDCl$_3$) δ 1.53 (d, J=7.1 Hz, 3H), 2.34 (d, J=1.0 Hz, 3H), 3.73-3.85 (m, 2H), 4.30-4.47 (m, 4H), 4.99-5.08 (m, 1H), 7.16-7.21 (m, 2H), 7.28 (d, J=7.7 Hz, 1H), 7.52 (d, J=7.7 Hz, 1H), 8.40 (dd, J=9.2, 2.7 Hz, 1H), 8.44 (br s, 1H), 8.71 (d, J=2.6 Hz, 1H).

Step 4. Synthesis of 2-{(2S)-1-[4-amino-2-(pentafluoro-λ$^6$-sulfanyl)phenoxy]propan-2-yl}-7-(4-methyl-1H-imidazol-1-yl)-3,4-dihydro-2H-pyrido[1,2-a]pyrazine-1,6-dione (C56). A mixture of 7-(4-methyl-1H-imidazol-1-yl)-2-{(2S)-1-[4-nitro-2-(pentafluoro-λ$^6$-sulfanyl)phenoxy]propan-2-yl}-3,4-dihydro-2H-pyrido[1,2-a]pyrazine-1,6-dione (C55) (790 mg, 1.44 mmol) and ethanol (10 mL) was heated to 55° C. Iron powder (99%, 243 mg, 4.31 mmol) and a solution of ammonium chloride (462 mg, 8.64 mmol) in water (2.5 mL) were added, and the reaction mixture was stirred at reflux for 3 hours. The reaction mixture was allowed to cool to room temperature, concentrated in vacuo, treated with ethyl acetate and saturated aqueous sodium bicarbonate solution and filtered through Celite. The filter pad was rinsed with water and ethyl acetate; the organic portion of the filtrate was washed with saturated aqueous sodium chloride solution, dried over magnesium sulfate, filtered, and concentrated under reduced pressure. Purification via silica gel chromatography (Gradient: 5% to 10% methanol in ethyl acetate) provided the product as a light yellow foam. Yield: 507 mg, 0.98 mmol, 68%. LCMS m/z 520.2 (M+1). $^1$H NMR (400 MHz, CDCl$_3$), characteristic peaks: δ 1.48 (d, J=7.2 Hz, 3H), 3.71-3.79 (m, 1H)

3.85-3.92 (m, 1H), 4.05 (dd, J=9.6, 5.5 Hz, 1H), 4.99-5.08 (m, 1H), 6.80 (dd, half of ABX pattern, J=8.8, 2.6 Hz, 1H), 6.86 (br d, half of AB quartet, J=8.8 Hz, 1H), 7.06 (d, J=2.6 Hz, 1H).

Step 5. Synthesis of 2-{(2S)-1-[4-chloro-2-(pentafluoro-λ⁶-sulfanyl)phenoxy]propan-2-yl}-7-(4-methyl-1H-imidazol-1-yl)-3,4-dihydro-2H-pyrido[1,2-a]pyrazine-1,6-dione (119). A solution of 2-{(2S)-1-[4-amino-2-(pentafluoro-λ⁶-sulfanyl)phenoxy]propan-2-yl}-7-(4-methyl-1H-imidazol-1-yl)-3,4-dihydro-2H-pyrido[1,2-a]pyrazine-1,6-dione (C56) (507 mg, 0.976 mmol) in a mixture of acetone (40 mL) and concentrated hydrochloric acid (4 mL) was cooled to −8° C. A solution of sodium nitrite (67.3 mg, 0.975 mmol) in water (5 mL) was added, the cooling bath was removed, and the reaction mixture was stirred at room temperature for 1 hour. The resulting orange solution was cooled to −2° C., and copper(I) chloride (99 mg, 1.0 mmol) was added. After two hours at room temperature, the reaction mixture was diluted with water (100 mL), and concentrated ammonium hydroxide was added drop-wise until the pH reached approximately 8. The bright blue mixture was extracted with ethyl acetate (2×75 mL), and the combined organic layers were washed with a 1:1 mixture of concentrated ammonium hydroxide and water (approximately 30 mL) until the aqueous layer was essentially colorless. The organic layer was washed with saturated aqueous sodium chloride solution, dried over magnesium sulfate, filtered, and concentrated under reduced pressure. Purification was first carried out by HPLC (Column: Phenomenex Luna C18, 5 μm; Mobile phase A: 0.1% formic acid in water; Mobile phase B: 0.1% formic acid in methanol; Gradient: 5% to 95% B) to afford 315 mg of the product, presumed to be a formate salt, as a light orange gum. This material was dissolved in ethyl acetate, washed with saturated aqueous sodium bicarbonate solution, washed with saturated aqueous sodium chloride solution, dried over magnesium sulfate, filtered, and concentrated in vacuo to afford a solid. This was further purified via silica gel chromatography (Eluents: 5%, then 10% methanol in ethyl acetate); the desired material was reconcentrated from diethyl ether to afford the product as a white solid. Yield: 217 mg, 0.403 mmol, 41%. LCMS m/z 539.2 (M+1). ¹H NMR (400 MHz, CDCl₃) δ 1.50 (d, J=7.2 Hz, 3H), 2.33 (d, J=1.0 Hz, 3H), 3.75 (ddd, half of ABXY pattern, J=13.5, 7.6, 4.2 Hz, 1H), 3.83 (ddd, half of ABXY pattern, J=13.5, 7.2, 4.2 Hz, 1H), 4.16 (dd, J=9.6, 5.6 Hz, 1H), 4.26-4.34 (m, 2H), 4.39 (ddd, half of ABXY pattern, J=14.3, 7.2, 4.2 Hz, 1H), 4.99-5.08 (m, 1H), 6.99 (d, J=9.0 Hz, 1H), 7.16-7.18 (m, 1H), 7.28 (d, J=7.7 Hz, 1H), 7.46 (dd, J=8.9, 2.5 Hz, 1H), 7.51 (d, J=7.7 Hz, 1H), 7.74 (d, J=2.5 Hz, 1H), 8.40-8.42 (m, 1H).

METHODS

Method A

Preparation of 2-[2-(aryloxy)ethyl] and 2-[2-(heteroaryloxy)ethyl]7-(4-methyl-1H-imidazol-1-yl)-3,4-dihydro-2H-pyrido[1,2-a]pyrazine-1,6-diones

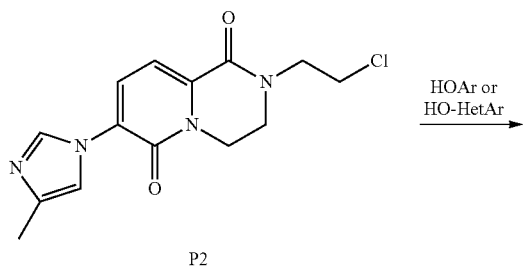

P2

HOAr or HO-HetAr →

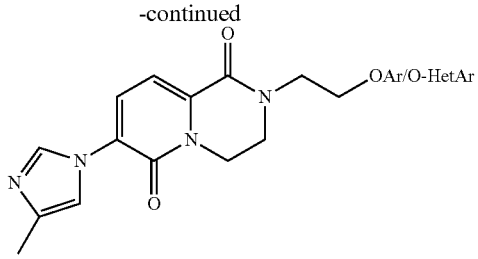

2-(2-Chloroethyl)-7-(4-methyl-1H-imidazol-1-yl)-3,4-dihydro-2H-pyrido[1,2-a]pyrazine-1,6-dione (P2) (10-20 mg) and a hydroxyaryl or hydroxyheteroaryl reactant (1-4 equivalents) were combined in dimethyl sulfoxide (P2 concentration 0.06-0.08 M). After addition of potassium carbonate (3.5 equivalents), the reaction mixture was heated at 100° C. until the reaction was judged to be complete via LCMS analysis (generally 1-3 hours). The mixture was then cooled to room temperature and filtered; the filtrate was concentrated in vacuo and purified using either silica gel chromatography or by reversed-phase HPLC with an appropriate gradient using one of the following systems:

a) Column: Waters Sunfire C18, 5 μm; Mobile phase A: 0.05% trifluoroacetic acid in water (v/v); Mobile phase B: 0.05% trifluoroacetic acid in acetonitrile (v/v);

b) Column: Waters XBridge C18, 5 μm; Mobile phase A: 0.03% ammonium hydroxide in water (v/v); Mobile phase B: 0.03% ammonium hydroxide in acetonitrile (v/v);

c) Column: Waters Sunfire C18 19×100, 5 μm; Mobile phase A: 0.05% formic acid in water (v/v); Mobile phase B: 0.05% formic acid in acetonitrile (v/v).

Method B

Preparation of ortho-substituted 7-(4-methyl-1H-imidazol-1-yl)-2-(2-phenoxyethyl)-3,4-dihydro-2H-pyrido[1,2-a]pyrazine-1,6-diones via Suzuki coupling

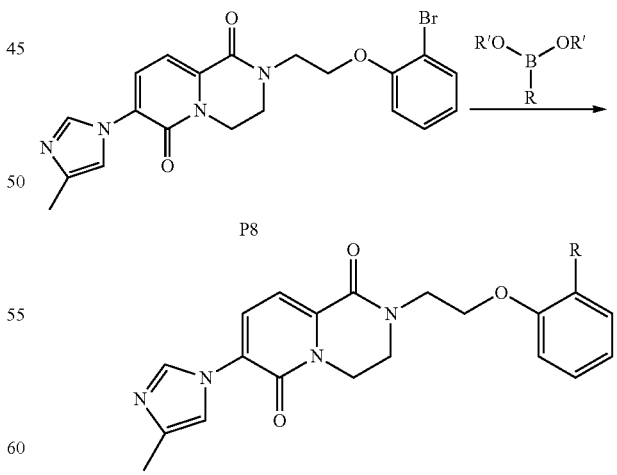

The boronic acid (72 μmol) was weighed into a vial and a solution of 2-[2-(2-bromophenoxy)ethyl]-7-(4-methyl-1H-imidazol-1-yl)-3,4-dihydro-2H-pyrido[1,2-a]pyrazine-1,6-dione (P8) (26.5 mg, 0.060 mmol) in 1,4-dioxane (750 μL) was added. Next, a solution of cesium carbonate (43.2 mg, 0.12 mmol) in water (150 μL) was added and nitrogen was bubbled through the reaction. Dichloro[1,1' bis(di-tert-butylphosphino)]ferrocene palladium(II) (2 mg, 0.003 mmol) was then added, nitrogen was bubbled through the reaction and the vial was capped and heated to 100° C. for 16 hours. The reaction was filtered; the solvent was removed in vacuo and the residue was purified by preparative reversed-phase HPLC. Purifications were carried out using an appropriate gradient on either a DIKMA Diamonsil(2) C18 column (5 μm) or a Boston Symmetrix C18 ODS-H column (5 μm), with the aqueous and the acetonitrile mobile phases each containing 0.225% formic acid.

TABLE 1

| Ex #* | Structure | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 3 | | Preparation 3, Ex 1 | 7-(4-methyl-1H-imidazol-1-yl)-2-[2-(1-naphthyloxy)ethyl]-3,4-dihydro-2H-pyrido[1,2-a]pyrazine-1,6-dione | 2.28 (d, J = 1.0 Hz, 3H), 4.01-4.05 (m, 2H), 4.14 (dd, J = 5.1, 4.5 Hz, 2H), 4.37-4.41 (m, 2H), 4.46 (dd, J = 5.0, 4.6 Hz, 2H), 6.82 (dd, J = 7.6, 0.7 Hz, 1H), 7.11-7.12 (m, 1H), 7.28 (d, J = 7.7 Hz, 1H), 7.37 (dd, J = 8.2, 7.7 Hz, 1H), 7.43 (d, J = 7.7 Hz, 1H), 7.45-7.54 (m, 3H), 7.80-7.85 (m, 1H), 8.11-8.16 (m, 1H), 8.21 (d, J = 1.3 Hz, 1H); 415.1 |
| 4 | | Ex 1[1] | 2-[2-(2,3-dichlorophenoxy)-2-methylpropyl]-7-(4-methyl-1H-imidazol-1-yl)-3,4-dihydro-2H-pyrido[1,2-a]pyrazine-1,6-dione | 1.42 (s, 6H), 2.29 (s, 3H), 3.90 (s, 2H), 4.08-4.13 (m, 2H), 4.37-4.42 (m, 2H), 7.03 (dd, J = 8.2, 1.2 Hz, 1H), 7.11-7.16 (m, 2H), 7.23 (dd, J = 8.0, 1.2 Hz, 1H), 7.29 (d, J = 7.8 Hz, 1H), 7.46 (d, J = 7.8 Hz, 1H), 8.23 (s, 1H); 461.2 |
| 5 | | Ex 1[2] | 7-(4-methyl-1H-imidazol-1-yl)-2-{2-[4-(trifluoromethyl)phenoxy]propyl}-3,4-dihydro-2H-pyrido[1,2-a]pyrazine-1,6-dione | 2.51 min[49]; 447.2 |
| 6 | | Method A | 2-{2-[(4-chloro-2-naphthyl)oxy]ethyl}-7-(4-methyl-1H-imidazol-1-yl)-3,4-dihydro-2H-pyrido[1,2-a]pyrazine-1,6-dione | 2.62 min[49]; 449.2, 451.2 |

TABLE 1-continued

| Ex #* | Structure R | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 7 | (7-methoxy-1-naphthyl)oxyethyl | Method A | 2-{2-[(7-methoxy-1-naphthyl)oxy]ethyl}-7-(4-methyl-1H-imidazol-1-yl)-3,4-dihydro-2H-pyrido[1,2-a]pyrazine-1,6-dione | 2.42 min[49]; 445.2 |
| 8 | (4-methoxy-1-naphthyl)oxyethyl | Method A | 2-{2-[(4-methoxy-1-naphthyl)oxy]ethyl}-7-(4-methyl-1H-imidazol-1-yl)-3,4-dihydro-2H-pyrido[1,2-a]pyrazine-1,6-dione | 2.19 min[49]; 445.2 |
| 9 | (7-chloro-2,3-dihydro-1H-inden-4-yl)oxyethyl | Method A[3] | 2-{2-[(7-chloro-2,3-dihydro-1H-inden-4-yl)oxy]ethyl}-7-(4-methyl-1H-imidazol-1-yl)-3,4-dihydro-2H-pyrido[1,2-a]pyrazine-1,6-dione | 2.34 min[49]; 439.2, 441.2 |
| 10 | (2,3,5-trichlorophenoxy)ethyl | Method A | 7-(4-methyl-1H-imidazol-1-yl)-2-[2-(2,3,5-trichlorophenoxy)ethyl]-3,4-dihydro-2H-pyrido[1,2-a]pyrazine-1,6-dione | 2.42 min[49]; 466.9 |
| 11 | (7-fluoro-1-benzofuran-4-yl)oxyethyl | Method A[4] | 2-{2-[(7-fluoro-1-benzofuran-4-yl)oxy]ethyl}-7-(4-methyl-1H-imidazol-1-yl)-3,4-dihydro-2H-pyrido[1,2-a]pyrazine-1,6-dione | 2.12 min[49]; 423.0 |
| 12 | [4-chloro-3-(trifluoromethyl)phenoxy]ethyl | Method A | 2-{2-[4-chloro-3-(trifluoromethyl)phenoxy]ethyl}-7-(4-methyl-1H-imidazol-1-yl)-3,4-dihydro-2H-pyrido[1,2-a]pyrazine-1,6-dione | 2.41 min[49]; 466.9, 468.9 |

TABLE 1-continued

| Ex #* | Structure R | Method of Preparation; Non-commercial Starting Materials | IUPAC Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|
| 13 | (2-tert-butylphenoxy)ethyl | Method A | 2-[2-(2-tert-butylphenoxy)ethyl]-7-(4-methyl-1H-imidazol-1-yl)-3,4-dihydro-2H-pyrido[1,2-a]pyrazine-1,6-dione | 2.33 min[49]; 421.3 |
| 14 | (5,6,7,8-tetrahydronaphthalen-1-yloxy)ethyl | Method A | 7-(4-methyl-1H-imidazol-1-yl)-2-[2-(5,6,7,8-tetrahydronaphthalen-1-yloxy)ethyl]-3,4-dihydro-2H-pyrido[1,2-a]pyrazine-1,6-dione | 2.38 min[49]; 419.0 |
| 15 | 2-(trifluoromethoxy)phenoxyethyl | Method A | 7-(4-methyl-1H-imidazol-1-yl)-2-{2-[2-(trifluoromethoxy)phenoxy]ethyl}-3,4-dihydro-2H-pyrido[1,2-a]pyrazine-1,6-dione | 2.37 min[49]; 449.2 |
| 16 | (2,3-dihydro-1H-inden-4-yloxy)ethyl | Method A | 2-[2-(2,3-dihydro-1H-inden-4-yloxy)ethyl]-7-(4-methyl-1H-imidazol-1-yl)-3,4-dihydro-2H-pyrido[1,2-a]pyrazine-1,6-dione | 2.16 min[49]; 405.2 |
| 17 | (2-chloro-4-methylphenoxy)ethyl | Method A | 2-[2-(2-chloro-4-methylphenoxy)ethyl]-7-(4-methyl-1H-imidazol-1-yl)-3,4-dihydro-2H-pyrido[1,2-a]pyrazine-1,6-dione | 2.18 min[49]; 413.0, 415.0 |
| 18 | (biphenyl-3-yloxy)ethyl | Method A | 2-[2-(biphenyl-3-yloxy)ethyl]-7-(4-methyl-1H-imidazol-1-yl)-3,4-dihydro-2H-pyrido[1,2-a]pyrazine-1,6-dione | 2.38 min[49]; 441.0 |

TABLE 1-continued

| Ex #* | Structure R | Method of Preparation; Non-commercial Starting Materials | IUPAC Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|
| 19 | (3-phenoxyphenoxy)ethyl group | Method A | 7-(4-methyl-1H-imidazol-1-yl)-2-[2-(3-phenoxyphenoxy)ethyl]-3,4-dihydro-2H-pyrido[1,2-a]pyrazine-1,6-dione | 2.62 min[49]; 457.3 |
| 20 | 2-[2-chloro-3-(trifluoromethyl)phenoxy]ethyl group | Method A | 2-[2-[2-chloro-3-(trifluoromethyl)phenoxy]ethyl]-7-(4-methyl-1H-imidazol-1-yl)-3,4-dihydro-2H-pyrido[1,2-a]pyrazine-1,6-dione | 2.47 min[49]; 467.2, 469.1 |
| 21 | 2-(2-cyclopropyl-4-fluorophenoxy)ethyl group | Method A[5] | 2-[2-(2-cyclopropyl-4-fluorophenoxy)ethyl]-7-(4-methyl-1H-imidazol-1-yl)-3,4-dihydro-2H-pyrido[1,2-a]pyrazine-1,6-dione | 2.43 min[49]; 423.2 |
| 22 | 2-[4-chloro-2-(trifluoromethyl)phenoxy]ethyl group | Preparation 8[6] | 2-{2-[4-chloro-2-(trifluoromethyl)phenoxy]ethyl}-7-(4-methyl-1H-imidazol-1-yl)-3,4-dihydro-2H-pyrido[1,2-a]pyrazine-1,6-dione | ¹H NMR (400 MHz, CD₃OD) δ 2.24 (d, J = 0.9 Hz, 3H), 3.90-3.94 (m, 2H), 4.01 (dd, J = 5.1, 5.0 Hz, 2H), 4.32-4.39 (m, 4H), 7.21-7.27 (m, 2H), 7.30-7.32 (m, 1H), 7.56-7.60 (m, 2H), 7.76 (d, J = 7.7 Hz, 1H), 8.30 (d, J = 1.3 Hz, 1H); 467.1 |
| 23 | 2-(2,3-dichloro-4-fluorophenoxy)ethyl group | Method A[7] | 2-[2-(2,3-dichloro-4-fluorophenoxy)ethyl]-7-(4-methyl-1H-imidazol-1-yl)-3,4-dihydro-2H-pyrido[1,2-a]pyrazine-1,6-dione | 2.44 min[49]; 451.1, 453.1 |

TABLE 1-continued

| Ex #* | Structure R | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 24 |  | Method A[8] | 7-(4-methyl-1H-imidazol-1-yl)-2-{2-[2-(3-methylisothiazol-5-yl)phenoxy]ethyl}-3,4-dihydro-2H-pyrido[1,2-a]pyrazine-1,6-dione | 2.04 min[49]; 462.0 |
| 25 | 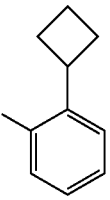 | Method A[9] | 2-[2-(2-cyclobutylphenoxy)ethyl]-7-(4-methyl-1H-imidazol-1-yl)-3,4-dihydro-2H-pyrido[1,2-a]pyrazine-1,6-dione | 2.36 min[49]; 419.0 |
| 26 | 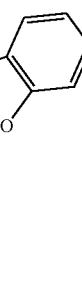 | Method A[10] | 2-[2-(dibenzo[b,d]furan-4-yloxy)ethyl]-7-(4-methyl-1H-imidazol-1-yl)-3,4-dihydro-2H-pyrido[1,2-a]pyrazine-1,6-dione | 2.35 min[49]; 454.9 |
| 27 | 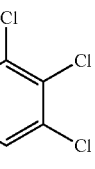 | Method A | 7-(4-methyl-1H-imidazol-1-yl)-2-[2-(2,3,4-trichlorophenoxy)ethyl]-3,4-dihydro-2H-pyrido[1,2-a]pyrazine-1,6-dione | $^1$H NMR (500 MHz, CDCl$_3$) δ 2.29 (s, 3H), 4.01-4.06 (m, 4H), 4.30 (dd, J = 4.9, 4.6 Hz, 2H), 4.40-4.44 (m, 2H), 6.79 (d, J = 8.8 Hz, 1H), 7.13-7.14 (m, 1H), 7.24-7.26 (m, 1H, assumed; partially obscured by solvent peak), 7.35 (d, J = 9.0 Hz, 1H), 7.44 (d, J = 7.8 Hz, 1H), 8.23 (br s, 1H); 467 |

TABLE 1-continued

| Ex #* | Structure R | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 28 | 3,5-dimethyl-4-chlorophenoxy group with propyl linker | Ex 1 | 2-[3-(4-chloro-3,5-dimethylphenoxy)propyl]-7-(4-methyl-1H-imidazol-1-yl)-3,4-dihydro-2H-pyrido[1,2-a]pyrazine-1,6-dione | 2.68 min[49]; 441.2, 443.2 |
| 29 | 2,4-bis(trifluoromethyl)phenoxy group with ethyl linker | Method A[11] | 2-{2-[2,4-bis(trifluoromethyl)phenoxy]ethyl}-7-(4-methyl-1H-imidazol-1-yl)-3,4-dihydro-2H-pyrido[1,2-a]pyrazine-1,6-dione | 2.62 min[49]; 501.2 |
| 30 | 2,4,5-trichlorophenoxy group with ethyl linker | Method A | 7-(4-methyl-1H-imidazol-1-yl)-2-[2-(2,4,5-trichlorophenoxy)ethyl]-3,4-dihydro-2H-pyrido[1,2-a]pyrazine-1,6-dione | 2.62 min[49]; 467.1, 469.1, 471.1 |
| 31 | 2,6-bis(trifluoromethyl)pyridin-3-yloxy group with ethyl linker | Method A | 2-(2-{[2,6-bis(trifluoromethyl)pyridin-3-yl]oxy}ethyl)-7-(4-methyl-1H-imidazol-1-yl)-3,4-dihydro-2H-pyrido[1,2-a]pyrazine-1,6-dione | 2.46 min[49]; 502.3 |
| 32 | 2-tert-butylphenoxy group with propyl linker | Ex 1 | 2-[3-(2-tert-butylphenoxy)propyl]-7-(4-methyl-1H-imidazol-1-yl)-3,4-dihydro-2H-pyrido[1,2-a]pyrazine-1,6-dione, trifluoroacetate salt | 2.76 min[49]; 435.2 |

TABLE 1-continued

| Ex #* | Structure R | Method of Preparation; Non-commercial Starting Materials | IUPAC Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|
| 33 | 2,3-dichlorophenoxy with ethyl linker | Ex 1 | 2-[2-(2,3-dichlorophenoxy)ethyl]-7-(4-methyl-1H-imidazol-1-yl)-3,4-dihydro-2H-pyrido[1,2-a]pyrazine-1,6-dione, trifluoroacetate salt | 2.11 min[49]; 433.1, 435.1 |
| 34 | biphenyl-2-yloxy with ethyl linker | Ex 1 | 2-[2-(biphenyl-2-yloxy)ethyl]-7-(4-methyl-1H-imidazol-1-yl)-3,4-dihydro-2H-pyrido[1,2-a]pyrazine-1,6-dione, trifluoroacetate salt | 0.85 min[50]; 441.5 |
| 35 | 2-chloro-4-fluoro-3-(trifluoromethyl)phenoxy with ethyl linker | Method A[12] | 2-{2-[2-chloro-4-fluoro-3-(trifluoromethyl)phenoxy]ethyl}-7-(4-methyl-1H-imidazol-1-yl)-3,4-dihydro-2H-pyrido[1,2-a]pyrazine-1,6-dione, trifluoroacetate salt | 2.53 min[49]; 485.2, 487.2 |
| 36 | 2-(2-methyl-1,3-thiazol-4-yl)phenoxy with ethyl linker | Method A | 7-(4-methyl-1H-imidazol-1-yl)-2-{2-[2-(2-methyl-1,3-thiazol-4-yl)phenoxy]ethyl}-3,4-dihydro-2H-pyrido[1,2-a]pyrazine-1,6-dione, trifluoroacetate salt | 2.33 min[51]; 462.2 |
| 37 | 2-(4-methylisothiazol-5-yl)phenoxy with ethyl linker | Method A[13] | 7-(4-methyl-1H-imidazol-1-yl)-2-{2-[2-(4-methylisothiazol-5-yl)phenoxy]ethyl}-3,4-dihydro-2H-pyrido[1,2-a]pyrazine-1,6-dione, trifluoroacetate salt | 2.28 min[49]; 462.2 |

TABLE 1-continued

| Ex #* | Structure R | Method of Preparation; Non-commercial Starting Materials | IUPAC Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|
| 38 | (F₃C-isoxazol-3-yl)-(4-methylphenoxy)propyl | Method A[14] | 7-(4-methyl-1H-imidazol-1-yl)-2-(2-{4-methyl-2-[5-(trifluoromethyl)isoxazol-3-yl]phenoxy}ethyl)-3,4-dihydro-2H-pyrido[1,2-a]pyrazine-1,6-dione, trifluoroacetate salt | 2.61 min[49]; 514.3 |
| 39 | (F₃C-isoxazol-3-yl)-phenoxypropyl | Method A[14] | 7-(4-methyl-1H-imidazol-1-yl)-2-(2-{2-[5-(trifluoromethyl)isoxazol-3-yl]phenoxy}ethyl)-3,4-dihydro-2H-pyrido[1,2-a]pyrazine-1,6-dione, trifluoroacetate salt | 2.45 min[49]; 500.3 |
| 40 | (CF₃-thiazol-4-yl)-phenoxypropyl | Ex 1; P3 | 7-(4-methyl-1H-imidazol-1-yl)-2-(2-{2-[2-(trifluoromethyl)-1,3-thiazol-4-yl]phenoxy}ethyl)-3,4-dihydro-2H-pyrido[1,2-a]pyrazine-1,6-dione | 2.28 (br s, 3H), 3.69-3.73 (m, 2H), 4.09 (dd, J = 5, 5 Hz, 2H), 4.20-4.24 (m, 2H), 4.38 (dd, J = 5, 5 Hz, 2H), 7.02 (d, J = 8.6 Hz, 1H), 7.09-7.14 (m, 2H), 7.24-7.27 (m, 1H, assumed; partially obscured by solvent peak), 7.35-7.40 (m, 1H), 7.44 (d, J = 7.6 Hz, 1H), 8.03 (s, 1H), 8.05 (dd, J = 7.7, 1.7 Hz, 1H), 8.21 (d, J = 1.4 Hz, 1H); 516.2 |
| 41 | (2-methyl-oxazol-4-yl)-phenoxypropyl | Method A[15] | 7-(4-methyl-1H-imidazol-1-yl)-2-{2-[2-(2-methyl-1,3-oxazol-4-yl)phenoxy]ethyl}-3,4-dihydro-2H-pyrido[1,2-a]pyrazine-1,6-dione, trifluoroacetate salt | 2.21 min[51]; 446.3 |

TABLE 1-continued

| Ex #* | Structure 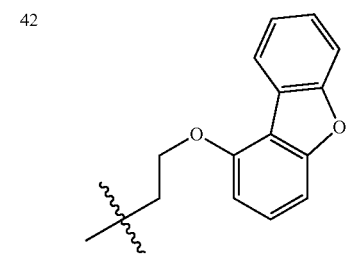 R | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 42 | 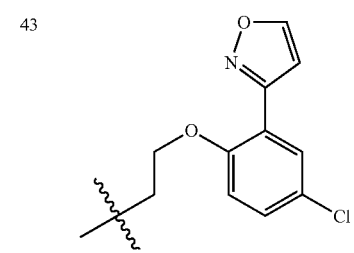 | Method A | 2-[2-(dibenzo[b,d]furan-1-yloxy)ethyl]-7-(4-methyl-1H-imidazol-1-yl)-3,4-dihydro-2H-pyrido[1,2-a]pyrazine-1,6-dione, trifluoroacetate salt | 2.57 min$^{49}$; 455.3 |
| 43 | 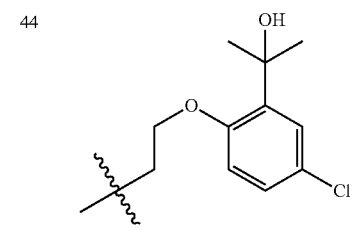 | Method A$^{16}$ | 2-[2-(4-chloro-2-isoxazol-3-ylphenoxy)ethyl]-7-(4-methyl-1H-imidazol-1-yl)-3,4-dihydro-2H-pyrido[1,2-a]pyrazine-1,6-dione, trifluoroacetate salt | 2.39 min$^{49}$; 466.2, 468.2 |
| 44 | 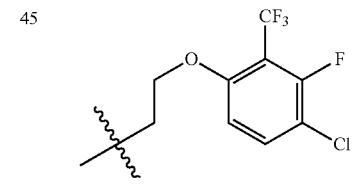 | Method A$^{17}$ | 2-{2-[4-chloro-2-(1-hydroxy-1-methyl-ethyl)phenoxy]ethyl}-7-(4-methyl-1H-imdiazol-1-yl)-3,4-dihydro-2H-pyrido[1,2-a]pyrazine-1,6-dione, trifluoroacetate salt | 2.19 min$^{49}$; 457.3, 459.3 |
| 45 | 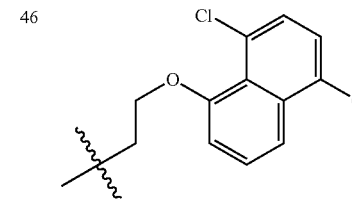 | Method A$^{18}$ | 2-{2-[4-chloro-3-fluoro-2-(trifluoromethyl)phenoxy]ethyl}-7-(4-methyl-1H-imidazol-1-yl)-3,4-dihydro-2H-pyrido[1,2-a]pyrazine-1,6-dione, trifluoroacetate salt | 2.59 min$^{49}$; 485.2, 487.3 |
| 46 | | Method A | 2-{2-[(5,8-dichloro-1-naphthyl)oxy]ethyl}-7-(4-methyl-1H-imidazol-1-yl)-3,4-dihydro-2H-pyrido[1,2-a]pyrazine-1,6-dione, trifluoroacetate salt | 2.73 min$^{49}$; 483.2, 485.2 |

TABLE 1-continued

[Core structure: 7-(4-methyl-1H-imidazol-1-yl)-3,4-dihydro-2H-pyrido[1,2-a]pyrazine-1,6-dione with N-R substituent]

| Ex #* | Structure R | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 47 | 6-chloro-7-(trifluoromethyl)quinolin-2-yloxy propyl group | Method A | 2-(2-{[6-chloro-7-(trifluoromethyl)quinolin-2-yl]oxy}ethyl)-7-(4-methyl-1H-imidazol-1-yl)-3,4-dihydro-2H-pyrido[1,2-a]pyrazine-1,6-dione | 2.04 min[49]; 518.3 |
| 48 | 4-fluoro-2-[2-(trifluoromethyl)pyridin-4-yl]phenoxy propyl group | Method A[19] | 2-(2-{4-fluoro-2-[2-(trifluoromethyl)pyridin-4-yl]phenoxy}ethyl)-7-(4-methyl-1H-imidazol-1-yl)-3,4-dihydro-2H-pyrido[1,2-a]pyrazine-1,6-dione | 2.30 min[49]; 528.2 |
| 49 | 2-[5-(trifluoromethyl)-1H-pyrazol-3-yl]phenoxy propyl group | Method A | 7-(4-methyl-1H-imidazol-1-yl)-2-(2-{2-[5-(trifluoromethyl)-1H-pyrazol-3-yl]phenoxy}ethyl)-3,4-dihydro-2H-pyrido[1,2-a]pyrazine-1,6-dione | 2.45 min[49]; 499.1 |
| 50 | 4-chloro-2-[3-(trifluoromethyl)-1H-pyrazol-1-yl]phenoxy propyl group | Method A[20] | 2-(2-{4-chloro-2-[3-(trifluoromethyl)-1H-pyrazol-1-yl]phenoxy}ethyl)-7-(4-methyl-1H-imidazol-1-yl)-3,4-dihydro-2H-pyrido[1,2-a]pyrazine-1,6-dione, trifluoroacetate salt | 3.63 min[49]; 533.0, 535.0 |

TABLE 1-continued

| Ex #* | Structure R | Method of Preparation; Non-commercial Starting Materials | IUPAC Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|
| 51 | | Method A | 2-(2-{[5-chloro-8-methyl-2-(trifluoromethyl)quinolin-4-yl]oxy}ethyl)-7-(4-methyl-1H-imidazol-1-yl)-3,4-dihydro-2H-pyrido[1,2-a]pyrazine-1,6-dione | 2.87 min[49]; 532.3, 534.3 |
| 52 | | Ex 1, Preparation 3 | 2-(2-{4-fluoro-2-[2-(trifluoromethyl)-1,3-thiazol-4-yl]phenoxy}ethyl)-7-(4-methyl-1H-imidazol-1-yl)-3,4-dihydro-2H-pyrido[1,2-a]pyrazine-1,6-dione | 2.29 (br s, 3H), 3.71-3.75 (m, 2H), 4.11 (dd, J = 5, 5 Hz, 2H), 4.26-4.30 (m, 2H), 4.34 (dd, J = 5, 5 Hz, 2H), 6.96 (dd, J = 9.3, 4.3 Hz, 1H), 7.03-7.09 (m, 1H), 7.12 (br s, 1H), 7.25-7.27 (m, 1H, assumed; partially obscured by solvent peak), 7.44 (d, J = 7.5 Hz, 1H), 7.88 (dd, J = 9.3, 3.1 Hz, 1H), 8.17 (s, 1H), 8.22 (d, J = 1 Hz, 1H); 534.2 |
| 53 | | Method A | 2-{2-[(6-fluoro-1-naphthyl)oxy]ethyl}-7-(4-methyl-1H-imidazol-1-yl)-3,4-dihydro-2H-pyrido[1,2-a]pyrazine-1,6-dione, trifluoroacetate salt | 2.47 min[49]; 433.3 |
| 54 | | Method A[21] | 2-(2-{5-methoxy-2-[5-(trifluoromethyl)-1H-pyrazol-3-yl]phenoxy}ethyl)-7-(4-methyl-1H-imidazol-1-yl)-3,4-dihydro-2H-pyrido[1,2-a]pyrazine-1,6-dione | 2.47 min[49]; 529.1 |

TABLE 1-continued

| Ex #* | Structure (R) | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 55 | (4-fluoro-2-(trifluoromethyl)phenoxymethyl isobutyl group) | Ex 1[22] | 2-{2-[4-fluoro-2-(trifluoromethyl)phenoxy]-1-methylethyl}-7-(4-methyl-1H-imidazol-1-yl)-3,4-dihydro-2H-pyrido[1,2-a]pyrazine-1,6-dione, formate salt | $^1$H NMR (400 MHz, CD$_3$OD) δ 1.41 (d, J = 7.0 Hz, 3H), 2.28 (br s, 3H), 3.73-3.85 (m, 2H), 4.19-4.38 (m, 4H), 5.01-5.11 (m, 1H), 7.20-7.25 (m, 1H), 7.25 (d, J = 7.7 Hz, 1H), 7.30-7.37 (m, 2H), 7.42 (br s, 1H), 7.83 (d, J = 7.8 Hz, 1H), 8.14 (s, 1H), 8.61 (br s, 1H); 465.0 |
| 56 | (4-fluoro-2-methylphenyl pyrazole CF$_3$ group) | Method A[23] | 2-(2-{[1-(4-fluoro-2-methylphenyl)-3-(trifluoromethyl)-1H-pyrazol-5-yl]oxy}ethyl)-7-(4-methyl-1H-imidazol-1-yl)-3,4-dihydro-2H-pyrido[1,2-a]pyrazine-1,6-dione | 2.49 min[49]; 531.3 |
| 57 | (CF$_3$, 4-fluoro phenoxy methylethyl group) | Ex 1; P4 | 2-{(1S)-2-[4-fluoro-2-(trifluoromethyl)phenoxy]-1-methylethyl}-7-(4-methyl-1H-imidazol-1-yl)-3,4-dihydro-2H-pyrido[1,2-a]pyrazine-1,6-dione | $^1$H NMR (400 MHz, CD$_3$OD) δ 1.42 (d, J = 7.0 Hz, 3H), 2.24 (d, J = 1.0 Hz, 3H), 3.73-3.85 (m, 2H), 4.20-4.38 (m, 4H), 5.02-5.12 (m, 1H), 7.21-7.26 (m, 1H), 7.26 (d, J = 7.8 Hz, 1H), 7.31-7.37 (m, 3H), 7.78 (d, J = 7.7 Hz, 1H), 8.30 (d, J = 1.4 Hz, 1H); 465.2 |
| 58 | (3-(difluoromethyl)isoxazol-5-yl phenoxyethyl group) | Method A | 2-(2-{2-[3-(difluoromethyl)isoxazol-5-yl]phenoxy}ethyl)-7-(4-methyl-1H-imidazol-1-yl)-3,4-dihydro-2H-pyrido[1,2-a]pyrazine-1,6-dione, trifluoroacetate salt | 2.39 min[49]; 482.3 |

TABLE 1-continued

| Ex #* | Structure R | Method of Preparation; Non-commercial Starting Materials | IUPAC Name | 1H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 59 | | Method A[21] | 2-(2-{4-chloro-2-[5-(trifluoromethyl)-1H-pyrazol-3-yl]phenoxy}ethyl)-7-(4-methyl-1H-imidazol-1-yl)-3,4-dihydro-2H-pyrido[1,2-a]pyrazine-1,6-dione | 2.64 min[49]; 533.0, 535.0 |
| 60 | | Method A | 2-{2-[(5-methoxy-1-naphthyl)oxy]ethyl}-7-(4-methyl-1H-imidazol-1-yl)-3,4-dihydro-2H-pyrido[1,2-a]pyrazine-1,6-dione, trifluoroacetate salt | 2.47 min[49]; 445.3 |
| 61 | | Method A | 7-(4-methyl-1H-imidazol-1-yl)-2-(2-{[7-(trifluoromethyl)quinolin-4-yl]oxy}ethyl)-3,4-dihydro-2H-pyrido[1,2-a]pyrazine-1,6-dione | 2.24 min[51]; 484.1 |
| 62 | | Method A[24] | 2-(2-{[6-chloro-8-methyl-2-(trifluoromethyl)quinolin-4-yl]oxy}ethyl)-7-(4-methyl-1H-imidazol-1-yl)-3,4-dihydro-2H-pyrido[1,2-a]pyrazine-1,6-dione | 2.91 min[49]; 532.3, 534.3 |

TABLE 1-continued

| Ex #* | Structure R | Method of Preparation; Non-commercial Starting Materials | IUPAC Name | 1H NMR (400 MHz, CDCl3), δ (ppm); Mass spectrum, observed ion m/z (M + 1) or HPLC retention time (minutes); Mass spectrum m/z (M + 1) (unless otherwise indicated) |
|---|---|---|---|---|
| 63 | 8-chloro-2-(trifluoromethyl)quinolin-4-yl with ethoxy linker | Method A | 2-(2-{[8-chloro-2-(trifluoromethyl)quinolin-4-yl]oxy}ethyl)-7-(4-methyl-1H-imidazol-1-yl)-3,4-dihydro-2H-pyrido[1,2-a]pyrazine-1,6-dione | 2.63 min[49]; 518.3, 520.3 |
| 64 | 5-fluoro-6-methoxy-1-naphthyl with ethoxy linker | Method A[25] | 2-{2-[(5-fluoro-6-methoxy-1-naphthyl)oxy]ethyl}-7-(4-methyl-1H-imidazol-1-yl)-3,4-dihydro-2H-pyrido[1,2-a]pyrazine-1,6-dione, trifluoroacetate salt | 2.48 min[49]; 463.3 |
| 65 | 4'-cyano-3'-(trifluoromethyl)biphenyl with ethoxy linker | Method A[26] | 2'-{2-[7-(4-methyl-1H-imidazol-1-yl)-1,6-dioxo-1,3,4,6-tetrahydro-2H-pyrido[1,2-a]pyrazin-2-yl]ethoxy}-3-(trifluoromethyl)biphenyl-4-carbonitrile | 2.66 min[49]; 534.1 |
| 66 | 8-chloro-5-fluoro-2-(trifluoromethyl)quinolin-4-yl with ethoxy linker | Method A[24] | 2-(2-{[8-chloro-5-fluoro-2-(trifluoromethyl)quinolin-4-yl]oxy}ethyl)-7-(4-methyl-1H-imidazol-1-yl)-3,4-dihydro-2H-pyrido[1,2-a]pyrazine-1,6-dione | 2.65 min[49]; 536.3, 538.3 |

TABLE 1-continued

| Ex #* | Structure R | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 67 | (3-chloro-4-fluoro-2-(trifluoromethyl)phenoxy)ethyl | Method A[27] | 2-{2-[3-chloro-4-fluoro-2-(trifluoromethyl)phenoxy]ethyl}-7-(4-methyl-1H-imidazol-1-yl)-3,4-dihydro-2H-pyrido[1,2-a]pyrazine-1,6-dione | 2.27 min[49]; 484.9, 486.9 |
| 68 | 2-[(4-chloroisoquinolin-1-yl)oxy]ethyl | Ex 1[28] | 2-{2-[(4-chloroisoquinolin-1-yl)oxy]ethyl}-7-(4-methyl-1H-imidazol-1-yl)-3,4-dihydro-2H-pyrido[1,2-a]pyrazine-1,6-dione, trifluoroacetate salt | 2.48 min[49]; 450.3, 452.3 |
| 69 | 2-{[6-(trifluoromethyl)quinolin-4-yl]oxy}ethyl | Method A | 7-(4-methyl-1H-imidazol-1-yl)-2-(2-{[6-(trifluoromethyl)quinolin-4-yl]oxy}ethyl)-3,4-dihydro-2H-pyrido[1,2-a]pyrazine-1,6-dione | 2.14 min[51]; 484.0 |
| 70 | 2-{3-[4-(pent-4-yn-1-yloxy)benzoyl]phenoxy}ethyl | Ex 1[29] | 7-(4-methyl-1H-imidazol-1-yl)-2-(2-{3-[4-(pent-4-yn-1-yloxy)benzoyl]phenoxy}ethyl)-3,4-dihydro-2H-pyrido[1,2-a]pyrazine-1,6-dione | 1.99-2.09 (m, 3H), 2.29 (s, 3H), 2.42-2.48 (m, 2H), 3.91-3.96 (m, 2H), 3.98-4.03 (m, 2H), 4.15-4.20 (m, 2H), 4.30-4.34 (m, 2H), 4.36-4.42 (m, 2H), 6.95-7.00 (m, 2H), 7.07-7.12 (m, 1H), 7.14 (br s, 1H), 7.26-7.47 (m, 5H, assumed; partially obscured by solvent peak), 7.79-7.83 (m, 2H), 8.23 (br s, 1H); 551.3 |

TABLE 1-continued

| Ex # | Structure R | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 71 | (9-methyl-9H-carbazol-4-yloxy)ethyl group | Method A[30] | 2-{2-[(9-methyl-9H-carbazol-4-yl)oxy]ethyl}-7-(4-methyl-1H-imidazol-1-yl)-3,4-dihydro-2H-pyrido[1,2-a]pyrazine-1,6-dione, trifluoroacetate salt | 2.11 min[49]; 468.1 |
| 72 | 2-{2-[3-(trifluoromethyl)isoxazol-5-yl]phenoxy}ethyl group | Method A; P5 | 7-(4-methyl-1H-imidazol-1-yl)-2-(2-{2-[3-(trifluoromethyl)isoxazol-5-yl]phenoxy}ethyl)-3,4-dihydro-2H-pyrido[1,2-a]pyrazine-1,6-dione | 2.29 (d, J = 1.0 Hz, 3H), 3.79-3.84 (m, 2H), 4.12 (dd, J = 5.3, 4.9 Hz, 2H), 4.31-4.35 (m, 2H), 4.41 (dd, J = 5.3, 4.9 Hz, 2H), 7.00 (s, 1H), 7.06 (br d, J = 8.6 Hz, 1H), 7.12-7.17 (m, 2H), 7.28 (d, J = 7.8 Hz, 1H), 7.47 (d, J = 7.8 Hz, 1H), 7.49 (ddd, J = 8.5, 7.4, 1.7 Hz, 1H), 7.91 (dd, J = 7.8, 1.8 Hz, 1H), 8.30 (d, J = 1.2 Hz, 1H); 500.2 |
| 73 | 2-{[4-fluoro-2-(trifluoromethyl)-1,3-benzothiazol-7-yl]oxy}ethyl group | Method A; P6 | 2-(2-{[4-fluoro-2-(trifluoromethyl)-1,3-benzothiazol-7-yl]oxy}ethyl)-7-(4-methyl-1H-imidazol-1-yl)-3,4-dihydro-2H-pyrido[1,2-a]pyrazine-1,6-dione | 2.29 (d, J = 0.8 Hz, 3H), 3.94-3.99 (m, 2H), 4.07 (dd, J = 5.0, 4.8 Hz, 2H), 4.41-4.48 (m, 4H), 6.92 (dd, J = 8.7, 3.1 Hz, 1H), 7.12-7.14 (m, 1H), 7.23-7.29 (m, 2H), 7.45 (d, J = 7.7 Hz, 1H), 8.24 (d, J = 1.0 Hz, 1H); 508.2 |
| 74 | 2-([1]benzofuro[3,2-c]pyridin-1-yloxy)ethyl group | Ex 1[31] | 2-[2-([1]benzofuro[3,2-c]pyridin-1-yloxy)ethyl]-7-(4-methyl-1H-imidazol-1-yl)-3,4-dihydro-2H-pyrido[1,2-a]pyrazine-1,6-dione | 2.28 (d, J = 0.9 Hz, 3H), 3.85-3.89 (m, 2H), 4.15-4.19 (m, 2H), 4.31-4.35 (m, 2H), 4.89-4.92 (m, 2H), 7.11-7.13 (m, 1H), 7.22 (d, J = 5.9 Hz, 1H), 7.29 (d, J = 7.6 Hz, 1H), 7.41 (ddd, J = 7.5, 7.5, 1.1 Hz, 1H), 7.44 (d, J = 7.7 Hz, 1H), 7.50 (ddd, J = 8.2, 7.4, 1.4 Hz, 1H), 7.61 (ddd, J = 8.2, 0.9, 0.8 Hz, 1H), 8.01 (ddd, J = 7.7, 1.4 0.6 Hz, 1H), 8.15 (d, J = 6.9 Hz, 1H), 8.21 (br d, J = 1.3 Hz, 1H); 456.3 |

TABLE 1-continued

| Ex #* | Structure R | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 75 | [Thiazole-CF3/pyridine-F structure] | Ex 1[32] | 2-[2-({5-fluoro-3-[2-(trifluoromethyl)-1,3-thiazol-4-yl]pyridin-2-yl}oxy)ethyl]-7-(4-methyl-1H-imidazol-1-yl)-3,4-dihydro-2H-pyrido[1,2-a]pyrazine-1,6-dione | 2.28 (d, J = 0.8 Hz, 3H), 3.72-3.77 (m, 2H), 4.14-4.18 (m, 2H), 4.30-4.35 (m, 2H), 4.71-4.75 (m, 2H), 7.11-7.12 (m, 1H), 7.24 (d, J = 7.6 Hz, 1H), 7.43 (d, J = 7.8 Hz, 1H), 7.99 (d, J = 2.9 Hz, 1H), 8.21 (d, J = 1.2 Hz, 1H), 8.38 (dd, J = 8.7, 3.0 Hz, 1H), 8.42 (s, 1H); 535.1 |
| 76 | [3,3-difluorocyclobutyl/4-fluorophenoxy structure] | Method A; P7 | 2-{2-[2-(3,3-difluorocyclobutyl)-4-fluorophenoxy]ethyl}-7-(4-methyl-1H-imidazol-1-yl)-3,4-dihydro-2H-pyrido[1,2-a]pyrazine-1,6-dione | 2.52 min[49]; 473.1 |
| 77 | [5-chloro-benzisothiazole structure] | Method A | 2-{2-[(5-chloro-1,2-benzisothiazol-3-yl)oxy]ethyl}-7-(4-methyl-1H-imidazol-1-yl)-3,4-dihydro-2H-pyrido[1,2-a]pyrazine-1,6-dione | 2.30 (d, J = 1.0 Hz, 3H), 3.85-3.89 (m, 2H), 4.08-4.11 (m, 2H), 4.35-4.39 (m, 2H), 4.82-4.86 (m, 2H), 7.13-7.15 (m, 1H), 7.28 (d, 1H, assumed; partially obscured by solvent peak), 7.46 (d, J = 7.7 Hz, 1H), 7.51 (dd, J = 8.6, 1.9 Hz, 1H), 7.72 (dd, J = 8.6, 0.5 Hz, 1H), 7.80 (dd, J = 2.0, 0.6 Hz, 1H), 8.28 (br d, J = 1.0 Hz, 1H); 456.2 |
| 78 | [6-methoxy-1-naphthyl structure] | Method A | 2-{2-[(6-methoxy-1-naphthyl)oxy]ethyl}-7-(4-methyl-1H-imidazol-1-yl)-3,4-dihydro-2H-pyrido[1,2-a]pyrazine-1,6-dione | 2.37 min[49]; 445.3 |

TABLE 1-continued

| Ex #* | Structure R | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 79 | | Method A[33] | 2-[2-(dibenzo[b,d]thien-1-yloxy)ethyl]-7-(4-methyl-1H-imidazol-1-yl)-3,4-dihydro-2H-pyrido[1,2-a]pyrazine-1,6-dione | 2.51 min[49]; 471.0 |
| 80 | | Method A[34] | 2-(2-{[7-fluoro-2-(trifluoromethyl)-1,3-benzothiazol-4-yl]oxy}ethyl)-7-(4-methyl-1H-imidazol-1-yl)-3,4-dihydro-2H-pyrido[1,2-a]pyrazine-1,6-dione | 2.50 min[49]; 508.0 |
| 81 | | Method A[35] | 7-(4-methyl-1H-imidazol-1-yl)-2-(2-{3-[3-(trifluoromethyl)-1H-pyrazol-1-yl]phenoxy}ethyl)-3,4-dihydro-2H-pyrido[1,2-a]pyrazine-1,6-dione, trifluoroacetate salt | 2.44 min[49]; 499.0 |
| 82 | | Method A | 2-{2-[(5-chloro-1,2-benzisoxazol-3-yl)oxy]ethyl}-7-(4-methyl-1H-imidazol-1-yl)-3,4-dihydro-2H-pyrido[1,2-a]pyrazine-1,6-dione | 2.30 (d, J = 0.8 Hz, 3H), 3.86-3.90 (m, 2H), 4.10 (dd, J = 5.1, 5.1 Hz, 2H), 4.38-4.42 (m, 2H), 4.75 (dd, J = 5.3, 5.1 Hz, 2H), 7.14 (br s, 1H), 7.28 (d, J = 8 Hz, 1H, assumed; partially obscured by solvent peak), 7.40 (br d, J = 8.8 Hz, 1H), 7.46 (d, J = 7.8 Hz, 1H), 7.52 (dd, J = 8.9, 2.0 Hz, 1H), 7.57 (br d, J = 2 Hz, 1H), 8.27 (br d, J = 1 Hz, 1H); 440.2, 442.2 |

TABLE 1-continued

| Ex #* | Structure R | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 83 | (7-fluoronaphthalen-1-yl)oxy-propyl | Method A; Example 2 for phenol | 2-{2-[(7-fluoronaphthalen-1-yl)oxy]ethyl}-7-(4-methyl-1H-imidazol-1-yl)-3,4-dihydro-2H-pyrido[1,2-a]pyrazine-1,6-dione | 2.27 (d, J = 1.0 Hz, 3H), 3.96-4.01 (m, 2H), 4.13 (dd, J = 5.1, 4.6 Hz, 2H), 4.36-4.41 (m, 2H), 4.43 (dd, J = 5.1, 4.7 Hz, 2H), 6.84 (br d, J = 7.7 Hz, 1H), 7.10-7.12 (m, 1H), 7.25-7.30 (m, 1H), 7.28 (d, J = 7.7 Hz, 1H), 7.33 (dd, J = 8.1, 7.8 Hz, 1H), 7.42 (d, J = 7.7 Hz, 1H), 7.45 (br d, J = 8.3 Hz, 1H), 7.70 (br dd, J = 10.4, 2.7 Hz, 1H), 7.80 (dd, J = 9.0, 5.6 Hz, 1H), 8.21 (d, J = 1.3 Hz, 1H); 433 |
| 84 | 7-chloro-2-(trifluoromethyl)quinolin-4-yloxy-propyl | Method A | 2-(2-{[7-chloro-2-(trifluoromethyl)quinolin-4-yl]oxy}ethyl)-7-(4-methyl-1H-imidazol-1-yl)-3,4-dihydro-2H-pyrido[1,2-a]pyrazine-1,6-dione | 2.31 (s, 3H), 3.97-4.02 (m, 2H), 4.19 (dd, J = 5.1, 4.9 Hz, 2H), 4.40-4.45 (m, 2H), 4.57 (dd, J = 5.1, 4.9 Hz, 2H), 7.07 (s, 1H), 7.16 (br s, 1H), 7.32 (d, J = 7.8 Hz, 1H), 7.56 (d, J = 7.8 Hz, 1H), 7.59 (dd, J = 9.0, 2.1 Hz, 1H), 8.07 (d, J = 8.8 Hz, 1H), 8.15 (d, (d, J = 2.0 Hz, 1H), 8.55 (br s, 1H); 518.2 |
| 85 | 4-fluoro-2-[3-(trifluoromethyl)-1H-pyrazol-1-yl]phenoxy-propyl | Method A$^{35}$ | 2-(2-{4-fluoro-2-[3-(trifluoromethyl)-1H-pyrazol-1-yl]phenoxy}ethyl)-7-(4-methyl-1H-imidazol-1-yl)-3,4-dihydro-2H-pyrido[1,2-a]pyrazine-1,6-dione | 2.13 min$^{49}$; 517.0 |
| 86 | [1-(trifluoromethyl)isoquinolin-4-yl]oxy-propyl | Method A$^{36}$ | 7-(4-methyl-1H-imidazol-1-yl)-2-(2-{[1-(trifluoromethyl)isoquinolin-4-yl]oxy}ethyl)-3,4-dihydro-2H-pyrido[1,2-a]pyrazine-1,6-dione, trifluoroacetate salt | 2.41 min$^{49}$; 484.3 |

TABLE 1-continued

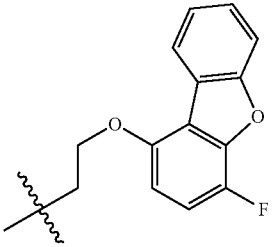 [SMILES: *CCOc1ccc(F)c2oc3ccccc3c12]

| Ex #* | Structure R | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 87 | 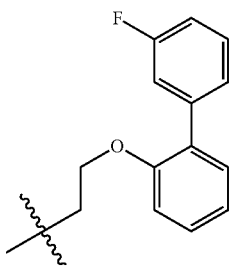 [SMILES: *CCOc1ccccc1-c1cccc(F)c1] | Method A[37] | 2-{2-[(4-fluorodibenzo[b,d]furan-1-yl)oxy]ethyl}-7-(4-methyl-1H-imidazol-1-yl)-3,4-dihydro-2H-pyrido[1,2-a]pyrazine-1,6-dione | 2.28 (d, J = 0.8 Hz, 3H), 3.94-3.99 (m, 2H), 4.17 (dd, J = 5.1, 4.9 Hz, 2H), 4.35-4.39 (m, 2H), 4.49 (dd, J = 5.1, 4.9 Hz, 2H), 6.68 (dd, J = 8.8, 2.7 Hz, 1H), 7.10-7.17 (m, 2H), 7.31 (d, J = 7.8 Hz, 1H), 7.38 (ddd, J = 7.6, 7.4, 0.8 Hz, 1H), 7.44 (d, J = 7.8 Hz, 1H), 7.50 (ddd, J = 8.4, 7.2, 1.3 Hz, 1H), 7.63 (br d, J = 8.4 Hz, 1H), 8.05 (ddd, J = 7.8, 1.4, 0.6 Hz, 1H), 8.21 (d, J = 1.4 Hz, 1H); 473 |
| 88 | 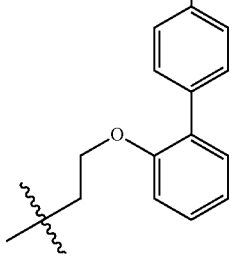 | Method B | 2-{2-[(3'-fluorobiphenyl-2-yl)oxy]ethyl}-7-(4-methyl-1H-imidazol-1-yl)-3,4-dihydro-2H-pyrido[1,2-a]pyrazine-1,6-dione, formate salt | 2.78 min[52]; 459 |
| 89 |  | Method B | 2-{2-[(4'-fluorobiphenyl-2-yl)oxy]ethyl}-7-(4-methyl-1H-imidazol-1-yl)-3,4-dihydro-2H-pyrido[1,2-a]pyrazine-1,6-dione, formate salt | 2.76 min[52]; 459 |

TABLE 1-continued

| Ex #* | Structure R | Method of Preparation; Non-commercial Starting Materials | IUPAC Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|
| 90 | (structure with 4-cyanobiphenyl-2-yloxypropyl) | Method B | 2'-{2-[7-(4-methyl-1H-imidazol-1-yl)-1,6-dioxo-1,3,4,6-tetrahydro-2H-pyrido[1,2-a]pyrazin-2-yl]ethoxy}biphenyl-4-carbonitrile, formate salt | 2.65 min⁵²; 466 |
| 91 | (structure with 2-(1,3-benzodioxol-5-yl)phenoxypropyl) | Method B | 2-{2-[2-(1,3-benzodioxol-5-yl)phenoxy]ethyl}-7-(4-methyl-1H-imidazol-1-yl)-3,4-dihydro-2H-pyrido[1,2-a]pyrazine-1,6-dione, formate salt | 2.74 min⁵²; 485 |
| 92 | (structure with 2-(1-benzofuran-2-yl)phenoxypropyl) | Method B | 2-{2-[2-(1-benzofuran-2-yl)phenoxy]ethyl}-7-(4-methyl-1H-imidazol-1-yl)-3,4-dihydro-2H-pyrido[1,2-a]pyrazine-1,6-dione, formate salt | 2.92 min⁵²; 481 |

TABLE 1-continued

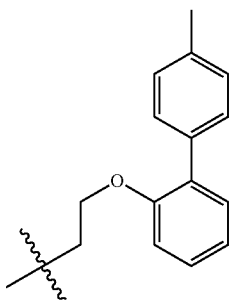 [SMILES: *CCOc1ccccc1-c1ccc(C)cc1]

| Ex #* | Structure 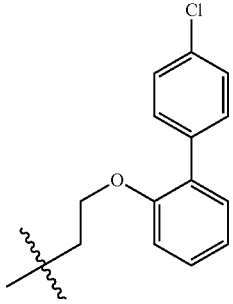 [SMILES: *CCOc1ccccc1-c1ccc(Cl)cc1] | Method of Preparation; Non-commercial Starting Materials | IUPAC Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|
| 93 | 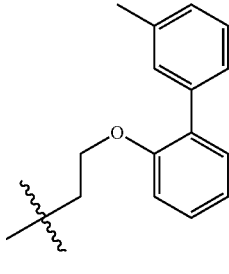 [SMILES: *CCOc1ccccc1-c1cccc(C)c1] | Method B | 2-{2-[(4'-methylbiphenyl-2-yl)oxy]ethyl}-7-(4-methyl-1H-imidazol-1-yl)-3,4-dihydro-2H-pyrido[1,2-a]pyrazine-1,6-dione, formate salt | 2.86 min[52]; 455 |
| 94 |  | Method B | 2-{2-[(4'-chlorobiphenyl-2-yl)oxy]ethyl}-7-(4-methyl-1H-imidazol-1-yl)-3,4-dihydro-2H-pyrido[1,2-a]pyrazine-1,6-dione, formate salt | 2.85 min[52]; 475 |
| 95 |  | Method B | 2-{2-[(3'-methylbiphenyl-2-yl)oxy]ethyl}-7-(4-methyl-1H-imidazol-1-yl)-3,4-dihydro-2H-pyrido[1,2-a]pyrazine-1,6-dione, formate salt | 2.86 min[52]; 455 |
| 96 | 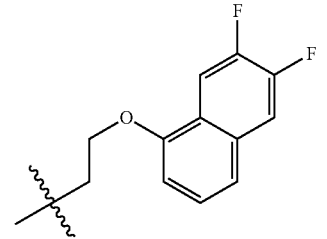 [SMILES: *CCOc1cccc2cc(F)c(F)cc12] | Method A[38] | 2-{2-[(6,7-difluoronaphthalen-1-yl)oxy]ethyl}-7-(4-methyl-1H-imidazol-1-yl)-3,4-dihydro-2H-pyrido[1,2-a]pyrazine-1,6-dione, trifluoroacetate salt | 2.53 min[49]; 451.2 |

TABLE 1-continued

| Ex #* | Structure R | Method of Preparation; Non-commercial Starting Materials | IUPAC Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|
| 97 | [benzothiazole with CF₃, linked via O-propyl] | Method A; P9 | 7-(4-methyl-1H-imidazol-1-yl)-2-(2-{[2-(trifluoromethyl)-1,3-benzothiazol-7-yl]oxy}ethyl)-3,4-dihydro-2H-pyrido[1,2-a]pyrazine-1,6-dione, trifluoroacetate salt | 2.31 min⁴⁹; 490.0 |
| 98 | [4,7-difluoronaphthalen-1-yloxy ethyl] | Method A³⁹ | 2-{2-[(4,7-difluoronaphthalen-1-yl)oxy]ethyl}-7-(4-methyl-1H-imidazol-1-yl)-3,4-dihydro-2H-pyrido[1,2-a]pyrazine-1,6-dione | 2.28 (br s, 3H), 3.96-4.02 (m, 2H), 4.12 (dd, J = 4.9, 4.9 Hz, 2H), 4.37-4.44 (m, 4H), 6.73 (dd, J = 8.3, 3.8 Hz, 1H), 6.99 (dd, J = 10.0, 8.4 Hz, 1H), 7.12 (br s, 1H), 7.30 (d, J = 7.6 Hz, 1H), 7.35 (ddd, J = 8.8, 8.6, 2.5 Hz, 1H), 7.44 (d, J = 7.6 Hz, 1H), 7.67-7.72 (m, 1H), 8.06 (dd, J = 9.2, 5.5 Hz, 1H), 8.22 (br s, 1H); 451.5 |
| 99 | [4-chloro-7-fluoroisoquinolinyloxy propyl] | Ex 1²⁸ | 2-{2-[(4-chloro-7-fluoroisoquinolin-1-yl)oxy]ethyl}-7-(4-methyl-1H-imidazol-1-yl)-3,4-dihydro-2H-pyrido[1,2-a]pyrazine-1,6-dione, trifluoroacetate salt | 2.51 min⁴⁹; 468.2, 470.2 |
| 100 | [4-chloro-2-(trifluoromethyl)phenoxy butan-2-yl] | Ex 1⁴⁰ | 2-{1-[4-chloro-2-(trifluoromethyl)phenoxy]butan-2-yl}-7-(4-methyl-1H-imidazol-1-yl)-3,4-dihydro-2H-pyrido[1,2-a]pyrazine-1,6-dione, trifluoroacetate salt | 2.70 min⁴⁹; 495.3, 497.3 |

TABLE 1-continued

| Ex #* | Structure R | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 101 | | Preparation 3[41], Ex 1 | 7-(4-methyl-1H-imidazol-1-yl)-2-(2-{[2-(trifluoromethyl)-1H-indol-4-yl]oxy}ethyl)-3,4-dihydro-2H-pyrido[1,2-a]pyrazine-1,6-dione | 2.34 min[49]; 472.2 |
| 102 | | Method A[42] | 7-(4-methyl-1H-imidazol-1-yl)-2-(2-{[1-methyl-2-(trifluoromethyl)-1H-indol-4-yl]oxy}ethyl)-3,4-dihydro-2H-pyrido[1,2-a]pyrazine-1,6-dione | 2.60 min[49]; 486.2 |
| 103 | | Ex 1[40] | 2-{1-[4-fluoro-2-(trifluoromethyl)phenoxy]butan-2-yl}-7-(4-methyl-1H-imidazol-1-yl)-3,4-dihydro-2H-pyrido[1,2-a]pyrazine-1,6-dione | 1.04 (t, J = 7.3 Hz, 3H), 1.82-2.02 (m, 2H), 2.35 (s, 3H), 3.71-3.79 (m ,1H), 3.83-3.91 (m, 1H), 4.18-4.28 (m, 2H), 4.29-4.38 (m, 2H), 4.75-4.83 (m, 1H), 6.95 (dd, J = 9.1, 4.0 Hz, 1H), 7.19-7.26 (m, 2H), 7.29-7.34 (m, 2H), 7.62 (d, J = 7.8 Hz, 1H), 8.54 (br s, 1H); 479.2 |
| 104 | | Method A[43] | 7-(4-methyl-1H-imidazol-1-yl)-2-(2-{2-[3-(trifluoromethyl)-1,2,4-thiadiazol-5-yl]phenoxy}ethyl)-3,4-dihydro-2H-pyrido[1,2-a]pyrazine-1,6-dione | 2.36 (s, 3H), 3.86-3.91 (m, 2H), 4.19 (dd, J = 5.5, 5.5 Hz, 2H), 4.33-4.38 (m, 2H), 4.67 (dd, J = 5.5, 5.4 Hz, 2H), 7.15-7.20 (m, 2H), 7.24 (br ddd, J = 8.7, 1 Hz, 1H), 7.29 (d, J = 7.7 Hz, 1H), 7.54 (d, J = 7.6 Hz, 1H), 7.59 (ddd, J = 8.4, 7.4, 1.7 Hz, 1H), 8.48-8.53 (m, 2H); 517.2 |

TABLE 1-continued

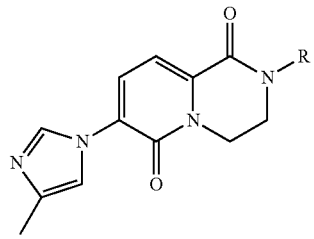

| Ex #* | Structure [R] | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 105 | (3-[2-(1,1,1-trifluoro-2-methylpropan-2-yl)-4-fluorophenoxy]propyl) | Method A[44] | 2-{2-[4-fluoro-2-(1,1,1-trifluoro-2-methylpropan-2-yl)phenoxy]ethyl}-7-(4-methyl-1H-imidazol-1-yl)-3,4-dihydro-2H-pyrido[1,2-a]pyrazine-1,6-dione | characteristic peaks: 1.67 (br s, 6H), 2.57 (d, J = 1.1 Hz, 3H), 4.01-4.06 (m, 2H), 4.24-4.28 (dd, J = 5, 5 Hz, 2H), 6.87-6.91 (m, 1H), 7.15 (dd, J = 11, 3 Hz, 1H), 7.30-7.32 (m, 1H), 7.38 (d, J = 7.7 Hz, 1H), 7.82 (d, J = 7.7 Hz, 1H); 493.1 |
| 106 | (3-[2-(bicyclo[1.1.1]pent-1-yl)phenoxy]propyl) | Method A[45] | 2-{2-[2-(bicyclo[1.1.1]pent-1-yl)phenoxy]ethyl}-7-(4-methyl-1H-imidazol-1-yl)-3,4-dihydro-2H-pyrido[1,2-a]pyrazine-1,6-dione | 2.14 (s, 6H), 2.32 (s, 3H), 2.56 (s, 1H), 3.86-3.91 (m, 2H), 4.03 (dd, J = 5.2, 5.0 Hz, 2H), 4.28 (dd, J = 5.2, 4.9 Hz, 2H), 4.34-4.39 (m, 2H), 6.82 (dd, J = 8.2, 0.7 Hz, 1H), 6.92 (ddd, J = 7.4, 7.4, 1.0 Hz, 1H), 7.09 (dd, J = 7.4, 1.8 Hz, 1H), 7.15-7.20 (m, 2H), 7.30 (d, J = 7.6 Hz, 1H), 7.50 (d, J = 7.7 Hz, 1H), 8.37 (br s, 1H); 431.1 |
| 107 | ((2S)-1-[4-chloro-2-(trifluoromethyl)phenoxy]propan-2-yl) | Ex 1[46] | 2-[(2S)-1-[4-chloro-2-(trifluoromethyl)phenoxy]propan-2-yl}-7-(4-methyl-1H-imidazol-1-yl)-3,4-dihydro-2H-pyrido[1,2-a]pyrazine-1,6-dione | 2.46 min[49]; 481.0 |
| 108 | (3-[(2,2-difluoro-2,3-dihydro-1H-inden-4-yl)oxy]propyl) | Method A[47] | 2-{2-[(2,2-difluoro-2,3-dihydro-1H-inden-4-yl)oxy]ethyl}-7-(4-methyl-1H-imidazol-1-yl)-3,4-dihydro-2H-pyrido[1,2-a]pyrazine-1,6-dione | 2.00 min[49]; 441.0 |
| 109 | (3-[(2,2-difluoro-1,3-benzodioxol-4-yl)oxy]propyl) | Method A[48] | 2-{2-[(2,2-difluoro-1,3-benzodioxol-4-yl)oxy]ethyl}-7-(4-methyl-1H-imidazol-1-yl)-3,4-dihydro-2H-pyrido[1,2-a]pyrazine-1,6-dione | 2.49 (s, 3H), 3.95-4.03 (m, 4H), 4.38-4.45 (m, 4H), 6.69 (br d, J = 8.6 Hz, 1H), 6.74-6.77 (m, 1H), 7.02 (dd, J = 8.4, 8.2 Hz, 1H), 7.26-7.29 (m, 1H, assumed; partially obscured by solvent peak), 7.34 (d, J = 7.6 Hz, 1H), 7.73 (d, J = 7.8 Hz, 1H), 9.08 (br s, 1H); 445.0 |

TABLE 1-continued

| Ex #* | Structure R | Method of Preparation; Non-commercial Starting Materials | IUPAC Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|
| 110 | | Method A[53] | 2-{2-[2-(bicyclo[1.1.1]pent-1-yl)-4-chlorophenoxy]ethyl}-7-(4-methyl-1H-imidazol-1-yl)-3,4-dihydro-2H-pyrido[1,2-a]pyrazine-1,6-dione | 2.47 min[49]; 465.1, 467.1 |
| 120 | | C54[54] | 7-(4-methyl-1H-imidazol-1-yl)-2-{(2S)-1-[2-pentafluoro-λ⁶-sulfanyl)phenoxy]propan-2-yl}-3,4-dihydro-2H-pyrido[1,2-a]pyrazine-1,6-dione | 1.50 (d, J = 7.0 Hz, 3H), 2.29 (s, 3H), 3.75 (ddd, half of ABXY pattern, J = 13.6, 8.0, 4.0 Hz, 1H), 3.86 (ddd, half of ABXY pattern, J = 13.3, 7.0, 3.8 Hz, 1H), 4.15 (dd, J = 9.5, 5.5 Hz, 1H), 4.24-4.35 (m, 2H), 4.39 (ddd, half of ABXY pattern, J = 14.6, 7.0, 4.0 Hz, 1H), 5.00-5.11 (m, 1H), 7.00-7.10 (m, 2H), 7.14 (br s, 1H), 7.27 (d, J = 8.0 Hz, 1H), 7.42-7.51 (m, 2H), 7.76 (br d, J = 8 Hz, 1H), 8.23 (br s, 1H); 505.0 |
| 121 | | P1[55] | 7-(4-methyl-1H-imidazol-1-yl)-2-{2-[2-(trimethylsilyl)phenoxy]ethyl}-3,4-dihydro-2H-pyrido[1,2-a]pyrazine-1,6-dione | 2.74 minutes[49]; 437.2 |
| 122 | | Method A; P2[56] | 2-(2-{4-fluoro-2-[2-(trifluoromethyl)oxetan-2-yl]phenoxy}ethyl)-7-(4-methyl-1H-imidazol-1-yl)-3,4-dihydro-2H-pyrido[1,2-a]pyrazine-1,6-dione, trifluoroacetate salt | 2.38 minutes[49]; 507.2 |

TABLE 1-continued

| Ex #* | Structure <br> ⤳R | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 123 | 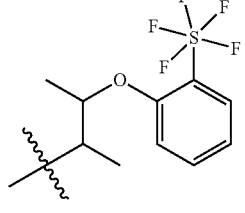 | Example 120; P14[57] | 7-(4-methyl-1H-imidazol-1-yl)-2-{3-[2-(pentafluoro-λ$^6$-sulfanyl)phenoxy]butan-2-yl}-3,4-dihydro-2H-pyrido[1,2-a]pyrazine-1,6-dione | $^1$H NMR (400 MHz, CD$_3$OD), mixture of diastereomers at the two methyl groups: δ 1.27-1.35 and 1.41-1.50 (2 m, total 6H), 2.24 (br s, 3H), 3.76-3.94 (m, 2H), 4.15-4.25 (m, 1H), 4.32-4.43 (m, 1H), 4.88-5.06 (m, 2H), 7.03-7.11 (m, 1H), 7.25-7.40 (m, 3H), 7.50-7.60 (m, 1H), 7.75-7.82 (m, 2H), 8.34 (br s, 1H); 519.6 |
| 124 | 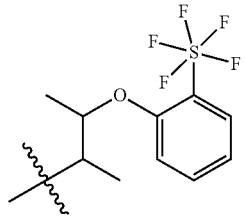 [SMILES: *C(C)C(C)Oc1ccccc1S(F)(F)(F)(F)F] | Example 123[58] | 7-(4-methyl-1H-imidazol-1-yl)-2-{3-[2-(pentafluoro-λ$^6$-sulfanyl)phenoxy]butan-2-yl}-3,4-dihydro-2H-pyrido[1,2-a]pyrazine-1,6-dione | 2.01 minutes[59]; 519.3 |
| 125 | 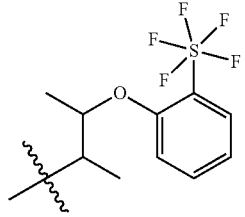 [SMILES: *C(C)C(C)Oc1ccccc1S(F)(F)(F)(F)F] | Example 123[58] | 7-(4-methyl-1H-imidazol-1-yl)-2-{3-[2-(pentafluoro-λ$^6$-sulfanyl)phenoxy]butan-2-yl}-3,4-dihydro-2H-pyrido[1,2-a]pyrazine-1,6-dione | 2.78 minutes[59]; 519.8 |
| 126 | | Example 123[58] | 7-(4-methyl-1H-imidazol-1-yl)-2-{3-[2-(pentafluoro-λ$^6$-sulfanyl)phenoxy]butan-2-yl}-3,4-dihydro-2H-pyrido[1,2-a]pyrazine-1,6-dione | 7.02 minutes[60]; 519.2 |

TABLE 1-continued

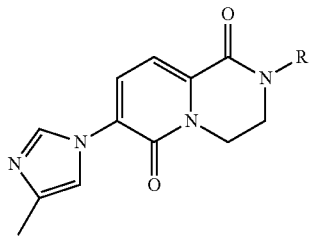

| Ex #* | Structure | Method of Preparation; Non-commercial Starting Materials | IUPAC Name | $^1$H NMR (400 MHz, CDCl[3]), δ (ppm); Mass spectrum, observed ion m/z (M + 1) or HPLC retention time (minutes); Mass spectrum m/z (M + 1) (unless otherwise indicated) |
|---|---|---|---|---|
| 127 | | Example 123[58] | 7-(4-methyl-1H-imidazol-1-yl)-2-{3-[2-(pentafluoro-λ[6]-sulfanyl)phenoxy]butan-2-yl}-3,4-dihydro-2H-pyrido[1,2-a]pyrazine-1,6-dione | 9.19 minutes[60]; 519.2 |

[1]Potassium hydroxide-mediated reaction of ethyl 2-bromo-2-methylpropanoate with 2,3-dichlorophenol provided ethyl 2-(2,3-dichlorophenoxy)-2-methylpropanoate. After reduction to the corresponding aldehyde with diisobutylaluminum hydride, reductive amination with 2-aminoethanol provided the requisite 2-aminoethanol derivative.
[2]Ethyl 2-[4-(trifluoromethyl)phenoxy]propanoate (D-i. Kato et al., J. Org. Chem. 2003, 68, 7234-7242) was subjected to ammonolysis to provide 2-[4-(trifluoromethyl)phenoxy]propanamide. Lithium aluminum hydride reduction gave the corresponding amine, which was converted to the requisite 2-aminoethanol derivative according to Preparation 4.
[3]4-Hydroxy-2,3-dihydro-1H-inden-1-one (W. Liu et al., Org. Lett. 2007, 9, 2915-2918) was reduced with sodium cyanoborohydride/trimethylsilyl chloride to provide 2,3-dihydro-1H-inden-4-ol. This was chlorinated with N-chlorosuccinimide to generate 7-chloro-2,3-dihydro-1H-inden-4-ol.
[4]2-Fluoro-5-methoxybenzaldehyde was subjected to a Baeyer-Villiger reaction, followed by basic ester hydrolysis. The resulting phenol was reacted with 2-bromo-1,1-dimethoxyethane and potassium carbonate to provide 2-(2,2-dimethoxyethoxy)-1-fluoro-4-methoxybenzene. Cyclization was effected with Amberlyst 15 (see A. Goel and M. Dixit, Synlett 2004, 1990-1994) to afford 7-fluoro-4-methoxy-1-benzofuran, which was demethylated using boron tribromide.
[5]2-Bromo-1-ethoxy-4-fluorobenzene was coupled with cyclopropylmagnesium bromide under [1,1'-bis(diphenylphosphino)ferrocene]dichloropalladium (II) catalysis. The resulting 2-cyclopropyl-1-ethoxy-4-fluorobenzene was converted to the phenol with boron trichloride.
[6]The requisite (2-bromoethoxy)benzene was prepared via Mitsunobu reaction of 2-bromoethanol with the appropriate phenol.
[7]2-Chloro-4-fluoro-1-methoxybenzene was treated with n-butyllithium and hexachloroethane; the resulting 2,3-dichloro-1-fluoro-4-methoxybenzene was demethylated with boron tribromide to provide the requisite phenol.
[8]The requisite phenol may be prepared either from 1-(2-methoxyphenyl)ethanone by the method of Y-i. Lin et al., J. Org. Chem. 1980, 45, 4857-60, or from 1-ethynyl-2-methoxybenzene according to L. Shen et al., Bioorg. Med. Chem. 2008, 16, 3321-3341.
[9]Benzyl 2-bromophenyl ether was metalated with n-butyllithium and reacted with cyclobutanone; hydrogenation of the resulting 1-[2-(benzyloxy)phenyl]cyclobutanol afforded the requisite phenol.
[10]The requisite phenol was prepared as described by D. A. Shultz et al., J. Org. Chem. 2006, 71, 9104-9113.
[11][2,4-Bis(trifluoromethyl)phenyl]boronic acid was oxidized with hydrogen peroxide to provide the requisite phenol.
[12]4-Fluoro-3-(trifluoromethyl)phenol was chlorinated with thionyl chloride to afford 2-chloro-4-fluoro-3-(trifluoromethyl)phenol.
[13]2-Methyl-4H-chromen-4-one was reacted with Lawesson's reagent, and the product was treated with 1,1'-sulfinimidoyldibenzene to provide 2-(4-methyl-1,2-thiazol-5-yl)phenol.
[14]The appropriately substituted 4,4,4-trifluoro-1-(2-methoxyphenyl)butane-1,3-dione was reacted with hydroxylamine, and the resulting oxime was cyclized under acidic conditions to yield the corresponding 3-(2-methoxyphenyl)-5-(trifluoromethyl)isoxazole. Demethylation with boron trichloride provided the requisite phenol.
[15]See J. C. Lee et al., Synth. Commun. 2003, 33, 1611-1614 for the construction of a similar 1,3-oxazole.
[16]6-Chloro-4H-chromen-4-one was treated with hydroxylamine hydrochloride in ethanol to provide a separable mixture of 4-chloro-2-isoxazol-3-ylphenol and 4-chloro-2-isoxazol-5-ylphenol.
[17]4-Chloro-2-(2-hydroxypropan-2-yl)phenol may be synthesized via reaction of methyl 5-chloro-2-hydroxybenzoate with a methyl Grignard reagent.
[18]1-Chloro-2-fluoro-4-methoxybenzene was converted to 1-chloro-2-fluoro-3-iodo-4-methoxybenzene (see G. L. Gunewald et al., J. Med. Chem. 1986, 29, 1972-1982). 1-Chloro-2-fluoro-3-iodo-4-methoxybenzene was treated with methyl difluoro(fluorosulfonyl)acetate in the presence of copper iodide (A. Khilevich et al., U.S. Pat. Appl. Publ. 2010, US 20100016373) to provide 1-chloro-2-fluoro-4-methoxy-3-(trifluoromethyl)benzene. 4-Chloro-3-fluoro-2-(trifluoromethyl)phenol was then obtained by demethylation using boron trichloride.
[19](5-Fluoro-2-hydroxyphenyl)boronic acid and 4-iodo-2-(trifluoromethyl)pyridine were reacted under Suzuki conditions to produce 4-fluoro-2-[2-(trifluoromethyl)pyridin-4-yl]phenol.
[20]A mixture of 4-chloro-2-iodophenol and 3-(trifluoromethyl)-1H-pyrazole was treated with copper oxide, cesium carbonate and 2-hydroxybenzaldehyde oxime to produce 4-chloro-2-[3-(trifluoromethyl)-1H-pyrazol-1-yl]phenol.
[21]Substituted 2-[5-(trifluoromethyl)-1H-pyrazol-3-yl]phenols may be prepared by sodium hydride-mediated reaction of the appropriate 1-(2-methoxyphenyl)ethanone with ethyl trifluoroacetate, followed by cyclization with hydrazine and deprotection of the aryl methyl ether. See S. X. Cao et al., PCT Int. Appl. 2007, WO 2007061923 A2 20070531.
[22]Alkylation of 4-fluoro-2-(trifluoromethyl)phenol with 1-chloroacetone afforded 1-[4-fluoro-2-(trifluoromethyl)phenoxy]acetone, which was subjected to reductive amination with 2-aminoethanol.
[23]4-Fluoro-2-methylaniline was converted to the diazonium salt and reduced with tin(II) chloride to provide (4-fluoro-2-methylphenyl)hydrazine; this was condensed with ethyl 4,4,4-trifluoro-3-oxobutanoate to afford 2-(4-fluoro-2-methylphenyl)-5-(trifluoromethyl)-2,4-dihydro-3H-pyrazol-3-one.
[24]A mixture of the appropriate aniline and ethyl 4,4,4-trifluoro-3-oxobutanoate may be treated with polyphosphoric acid to afford the requisite 2-(trifluoromethyl)quinolin-4-ol (see British Pat. Appl. GB 1419789 A 19751231).
[25]5-Fluoro-6-methoxynaphthalen-1-ol may be prepared according to J. Liu et al., Bioorg. Med. Chem. Lett. 2001, 11, 2903-2905.
[26]2'-Hydroxy-3-(trifluoromethyl)biphenyl-4-carbonitrile was prepared by the method of J. A. Van Camp et al., Bioorg. Med. Chem. Lett. 2007, 17, 5529-5532.
[27]Iodination of 2-chloro-1-fluoro-4-methoxybenzene (see R. Sanz et al., J. Org. Chem. 2007, 72, 5113-5118) followed by a copper-mediated coupling with methyl difluoro(fluorosulfonyl)acetate and demethylation with boron trichloride produced 3-chloro-4-fluoro-2-(trifluoromethyl)phenol.
[28]The appropriately substituted isoquinolin-1-ol was treated with N-chlorosuccinimide to provide the 4-chloroisoquinolin-1-ol, which was treated with phosphorus oxychloride to afford a 1,4-dichloroisoquinoline. This was treated with 2-aminoethanol followed by reductive amination of {[tert-butyl(dimethyl)silyl]oxy}acetaldehyde. Deprotection under acidic conditions yielded the requisite 2-{{2-[(4-chloroisoquinolin-1-yl)oxy]ethyl}amino}ethanol.
[29]Demethylation of (3-methoxyphenyl)(4-methoxyphenyl)methanone with pyridine hydrochloride followed by monoprotection provided 3-(4-hydroxybenzoyl)phenyl 2,2-dimethylpropanoate. Alkylation with 5-chloro-1-pentyne followed by basic hydrolysis gave (3-hydroxyphenyl)[4-(pent-4-yn-1-yloxy)phenyl]methanone, which was converted to the substituted 2-aminoethanol according to the method of Preparation 8.

TABLE 1-continued

| Ex #* | Structure | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|

[30] 9H-Carbazol-4-ol was O-protected using benzyl bromide, then N-methylated with iodomethane. Palladium-mediated deprotection provided 9-methyl-9H-carbazol-4-ol.

[31] A mixture of 1-benzofuran-2-carbaldehyde and propanedioic acid was treated with piperidine to give (2E)-3-(1-benzofuran-2-yl)prop-2-enoic acid. The resulting acid was converted to the acyl azide, then cyclized to [1]benzofuro[3,2-c]pyridin-1(2H)-one with tri-n-butylamine at 180° C. Treatment with phosphorus oxychloride provided 1-chloro[1]benzofuro[3,2-c]pyridine, which was converted to the requisite 2-aminoethanol according to the method of footnote 32.

[32] Base-mediated aryl substitution of 2-bromo-5-fluoro-3-[2-(trifluoromethyl)-1,3-thiazol-4-yl]pyridine with 2-aminoethanol followed by reductive amination of {[tert-butyl(dimethyl)silyl]oxy}acetaldehyde and deprotection under acidic conditions produced 2-{[2-{{[5-fluoro-3-[2-(trifluoromethyl)-1,3-thiazol-4-yl]pyridin-2-yl}oxy)ethyl]amino}ethanol.

[33] Dibenzo[b,d]thiophene-1-ol may be prepared by the method M. M. Oliveira et al, *Tetrahedron* 2002, 58, 1709-1718.

[34] 5-Fluoro-2-methoxyaniline was converted to 2,2,2-trifluoro-N-(5-fluoro-2-methoxyphenyl)ethanethioamide via treatment with trifluoroacetic anhydride followed by Lawesson's reagent. After cyclization to 7-fluoro-4-methoxy-2-(trifluoromethyl)-1,3-benzothiazole using the method of K. Inamoto et al., *Org. Lett.* 2008, 10, 5147-5150, methyl ether cleavage with boron trichloride afforded the requisite phenol.

[35] Copper-mediated coupling between the appropriately substituted bromo or iodo methoxybenzene and 3-(trifluoromethyl)-1H-pyrazole yielded a methoxyphenyl-substituted 3-(trifluoromethyl)-1H-pyrazole, which was demethylated with boron tribromide to produce the requisite [3-(trifluoromethyl)-1H-pyrazol-1-yl]phenol.

[36] 1-Chloroisoquinolin-4-ol was treated with tert-butyldimethylsilyl chloride to product 4-{[tert-butyl(dimethyl)silyl]oxy}-1-chloroisoquinoline. Halogen exchange gave 4-{[tert-butyl(dimethyl)silyl]oxy}-1-iodoisoquinoline, which was treated with copper iodide and methyl difluoro(fluorosulfonyl)acetate to produce 1-(trifluoromethyl)isoquinolin-4-ol.

[37] 3-Chloro-4-fluorophenol was acylated with diethylcarbamoyl chloride to produce 3-chloro-4-fluorophenyl diethylcarbamate, which was converted to 3-chloro-4-fluoro-2-iodophenyl diethylcarbamate via ortho-metalation followed by treatment with iodine. Basic hydrolysis provided 3-chloro-4-fluoro-2-iodophenol, which was coupled to (2-hydroxyphenyl)boronic acid under Suzuki conditions to give 6-chloro-5-fluorobiphenyl-2,2'-diol. Copper-mediated cyclization provided 4-fluorodibenzo[b,d]furan-1-ol.

[38] 1,2-Dibromo-4,5-difluorobenzene was treated with n-butyllithium followed by furan to give 6,7-difluoro-1,4-dihydro-1,4-epoxynaphthalene, which was treated with acid to produce 6,7-difluoronaphthalen-1-ol.

[39] 7-Fluoronaphthalen-1-ol was methylated to give 7-fluoro-1-methoxynaphthalene, which was brominated with N-bromosuccinimide to give 1-bromo-6-fluoro-4-methoxynaphthalene. Treatment with n-butyllithium and N-fluoro-N-(phenylsulfonyl)benzenesulfonamide, followed by demethylation with boron tribromide, afforded 4,7-difluoronaphthalen-1-ol.

[40] O-Alkylation of the appropriately substituted phenol with 1-bromobutan-2-one, followed by reductive amination with 2-aminoethanol, afforded the requisite 2-aminoethanol derivative.

[41] [4-(Benzyloxy)-1-(tert-butoxycarbonyl)-1H-indol-2-yl]boronic acid and trimethyl(trifluoromethyl)silane were combined to give tert-butyl 4-(benzyloxy)-2-(trifluoromethyl)-1H-indole-1-carboxylate, which was debenzylated via ammonium formate transfer hydrogenation to give tert-butyl 4-hydroxy-2-(trifluoromethyl)-1H-indole-1-carboxylate.

[42] 4-(Benzyloxy)-1-methyl-1H-indole and 3,3-dimethyl-1-(trifluoromethyl)-1,2-benziodoxole were treated with copper(I) acetate to give 4-(benzyloxy)-1-methyl-2-(trifluoromethyl)-1H-indole. Debenzylation via transfer hydrogenation with ammonium formate afforded 1-methyl-2-(trifluoromethyl)-1H-indol-4-ol.

[43] A Suzuki reaction between (2-hydroxyphenyl)boronic acid and 5-chloro-3-(trifluoromethyl)-1,2,4-thiadiazole provided the requisite phenol.

[44] 1-(5-Fluoro-2-methoxyphenyl)ethanone was converted to 4-fluoro-2-(2,2,2-trifluoro-1,1-dimethylethyl)phenol using the general method of R. M. Garbaccio et al., *ACS Med. Chem. Lett.* 2010, 1, 406-410. Cleavage of the methyl ether was carried out with boron tribromide to afford the requisite phenol.

[45] Reaction of 2-methoxyphenylmagnesium bromide with [1.1.1]propellane (see A. B. Shtarev et al., *J. Am. Chem. Soc.* 2001, 123, 3484-3492) afforded 1-(2-methoxyphenyl)bicyclo[1.1.1]pentane, which was treated with boron tribromide to provide the requisite phenol.

[46] tert-Butyl [(1S)-2-hydroxy-1-methylethyl]carbamate was O-acylated with benzoyl chloride, and the resulting compound was deprotected under acidic conditions. The resulting primary amine was converted to 2-aminoethanol derivative (2S)-2-[(2-hydroxyethyl)amino]propyl benzoate using the general procedure described in Preparation 4. Reaction with P1 under the conditions of Example 1 provided (2S)-2-[7-(4-methyl-1H-imidazol-1-yl)-1,6-dioxo-1,3,4,6-tetrahydro-2H-pyrido[1,2-a]pyrazin-2-yl]propyl benzoate, which was subjected to ester hydrolysis under basic conditions followed by Mitsunobu reaction with 4-chloro-2-(trifluoromethyl)phenol.

[47] 4-Bromo-1,3-dihydro-2H-inden-2-one was converted to 4-bromo-2,2-difluoroindane with (diethylamino)sulfur trifluoride. Palladium-catalyzed reaction with bis(pinacolato)diboron, followed by oxidation with peracetic acid, afforded 2,2-difluoroindan-4-ol.

[48] Treatment of (2,2-difluoro-1,3-benzodioxol-4-yl)boronic acid with hydrogen peroxide provided 2,2-difluoro-1,3-benzodioxol-4-ol.

[49] HPLC conditions. Column: Waters Atlantis dC18 4.6 × 50 mm, 5 μm; Mobile phase A: 0.05% trifluoroacetic acid in water (v/v); Mobile phase B: 0.05% trifluoroacetic acid in acetonitrile (v/v); Gradient: 5% to 95% B over 4.0 minutes, linear; Flow rate: 2 mL/minute.

[50] HPLC conditions. Column: Waters Acquity HSS T3 2.1 × 50 mm, 1.8 μm; Mobile phase A: 0.05% trifluoroacetic acid in water (v/v); Mobile phase B: 0.05% trifluoroacetic acid in acetonitrile (v/v); Gradient: 5% to 98% B over 1.6 minutes, linear; Flow rate: 1.3 mL/minute.

[51] HPLC conditions. Column: Waters XBridge C18 4.6 × 50 mm, 5 μm; Mobile phase A: 0.03% ammonium hydroxide in water (v/v); Mobile phase B: 0.03% ammonium hydroxide in acetonitrile (v/v); Gradient: 5% to 95% B over 4.0 minutes, linear; Flow rate: 2 mL/minute.

[52] HPLC conditions. Column: Water XBridge C18 2.1 × 50 mm, 5 μm; Mobile phase A: 0.0375% trifluoroacetic acid in wate r(v/v); Mobile phase B: 0.01875% trifluoroacetic acid in actonitrile (v/v); Gradient: 1% to 5% B over 0.6 minutes, then 5% to 100% B over 3.4 minutes; Flow rate: 0.8 mL/minute.

[53] 2-(Bicyclo[1.1.1]pent-1-yl)phenol (see footnote 45) was chlorinated according to the method of N. Narender et al., *Synth. Commun.* 2002, 32, 279-286 to provide the requisite 2-(bicyclo[1.1.1]pent-1-yl)-4-chlorophenol.

[54] Reaction of C54 with 1-fluoro-2-(pentafluoro-λ$^6$-sulfanyl)benzene was carried out using sodium hydride.

[55] P1 was converted to 2-(2-hydroxyethyl)-7-(4-methyl-1H-imidazol-1-yl)-3,4-dihydro-2H-pyrido[1,2-a]pyrazine-1,6-dione via reaction with 2-[(2-{[tert-butyl(dimethyl)silyl]oxy}ethyl)amino]ethanol according to the method described for preparation of P8 in Preparation 8, followed by protecting group removal with hydrogen chloride in methanol. 2-[(2-{[tert-Butyl(dimethyl)silyl]oxy}ethyl)amino]ethanol was synthesized via reductive amination of {[tert-butyl(dimethyl)silyl]oxy}acetaldehyde with 2-aminoethanol and sodium borohydride. Mitsunobu reaction of 2-(2-hydroxyethyl)-7-(4-methyl-1H-imidazol-1-yl)-3,4-dihydro-2H-pyrido[1,2-a]pyrazine-1,6-dione with 2-(trimethylsilyl)phenol using the method described by T. Tsunoda et al., *Tetrahedron Lett.* 1993, 34, 1639-1642 afforded this Example.

[56] Synthesis of the requisite 4-fluoro-2-[2-(trifluoromethyl)oxetan-2-yl]phenol may be carried out from 4-fluoro-2-(2,2,2-trifluoro-1-hydroxyethyl)phenol (see J. Zhang et al., *Synth. Commun.* 2011, 41, 3045-3052). Selective alkylation of the phanol, using allyl bromide and a base such as potassium carbonate, followed by a Swern oxidation of the benzylic alcohol, provides 2,2,2-trifluoro-1-[5-fluoro-2-(prop-2-en-1-yloxy)phenyl]ethanone. This material was reacted with trimethylsulfoxonium iodide and potassium tert-butoxide to afford 2-[5-fluoro-2-(prop-2-en-1-yloxy)phenyl]-2-(trifluoromethyl)oxetane; the allyl group was removed using tetrakis(triphenylphosphine)palladium(0) and morpholine.

[57] Intermediate 2-(3-hydroxybutan-2-yl)-7-(4-methyl-1H-imidazol-1-yl)-3,4-dihydro-2H-pyrido[1,2-a]pyrazine-1,6-dione was prepared from P14 using the method described for synthesis of C54 in Example 119, except that 3-aminobutan-2-ol was used in place of (2S)-2-aminopropan-1-ol. Example 123 is a mixture of four diastereomers, which were separated to provide Examples 124-127.

TABLE 1-continued

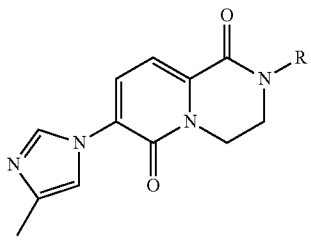

| Ex #* | Structure <br> ![R structure] | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|

[58]Example 123 was separated into its diastereomers (Examples 124-127) via the following sequence: Example 123 was subjected to HPLC separation (Column: Phenomenex Silica, 5 μm; Mobile phase A: heptane; Mobile phase B: ethanol; Gradient: 5% to 100% B) to afford a mixture of the two higher R$_f$ compounds (Mixture A) and a mixture of the two lower R$_f$ compounds (Mixture B). Mixture A was separated via supercritical fluid chromatography (Column: Chiralpak AS-H, 5 μm; Mobile phase: 75:25 carbon dioxide/ethanol). Example 124 was the first-eluting isomer, and the second-eluting isomer was Example 125. Mixture B was separated via supercritical fluid chromatography (Column: Chiralpak AS-H, 5 μm; Mobile phase: 80:20 carbon dioxide/methanol, containing 0.2% isopropylamine). Example 126 was the first-eluting isomer, and second-eluting isomer was Example 127.
[59]Supercritical fluid chromatography conditions. Column: Chiralpak AS-H, 4.6 × 250 mm, 5 μm; Mobile phase: 80:20 carbon dioxide/ethanol; Flow rate: 2.5 mL/minute.
[60]Supercritical fluid chromatography conditions. Column: Chiralpak AS-H, 4.6 × 250 mm, 5 μm; Mobile phase: 75:25 carbon dioxide/methanol; Flow rate: 2.5 mL/minute.

TABLE 2

| Ex # | Structure | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 111 | [structure] | Ex 1 | 2-{2-[4-chloro-2-(trifluoromethyl)phenoxy]ethyl}-8-(4-methyl-1H-imidazol-1-yl)-2,3,4,5-tetrahydropyrido[1,2-a][1,4]diazepine-1,7-dione | 2.51 min$^3$; 481.1, 483.1 |
| 112 | [structure] | Ex 1$^1$ | (4S)-2-{2-[4-fluoro-2-(trifluoromethyl)phenoxy]ethyl}-4-methyl-7-(4-methyl-1H-imidazol-1-yl)-3,4-dihydro-2H-pyrido[1,2-a]pyrazine-1,6-dione | 1.43 (d, J = 6.6 Hz, 3H), 2.29 (br s, 3H), 3.67 (dd, J = 13.6, 1.4 Hz, 1H), 3.89-3.96 (m, 1H), 4.08-4.16 (m, 2H), 4.32 (br dd, J = 4.7, 4.6 Hz, 2H), 5.23-5.30 (m, 1H), 6.95 (dd, J = 9.0, 4.2 Hz, 1H), 7.15 (br s, 1H), 7.19-7.25 (m, 1H), 7.27 (d, J = 7.7 Hz, 1H), 7.33 (dd, J = 8.0, 3.1 Hz, 1H), 7.44 (d, J = 7.7 Hz, 1H), 8.25 (br s, 1H); 465.2 |

TABLE 2-continued

| Ex # | Structure | Method of Preparation; Non-commercial Starting Materials | IUPAC Name | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|---|
| 113 | 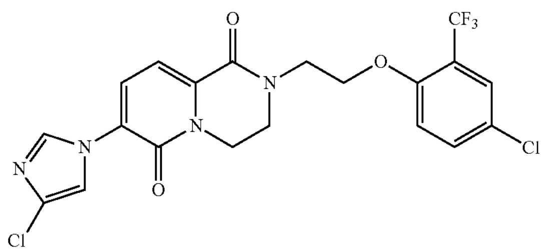 [SMILES: O=C1c2ccc(-n3cnc(Cl)c3)c(=O)n2CCN1CCOc1ccc(Cl)cc1C(F)(F)F] | Ex 1; P11[2] | 7-(4-chloro-1H-imidazol-1-yl)-2-{2-[4-chloro-2-(trifluoromethyl)phenoxy]ethyl}-3,4-dihydro-2H-pyrido[1,2-a]pyrazine-1,6-dione | 3.14 min[3]; 487.1, 489.1// $^1$H NMR (400 MHz, CD$_3$OD) δ 3.89-3.94 (m, 2H), 4.01 (dd, J = 5.1, 5.0 Hz, 2H), 4.31-4.38 (m, 4H), 7.22 (br d, J = 9.7 Hz, 1H), 7.23 (d, J = 7.8 Hz, 1H), 7.54-7.58 (m, 2H), 7.60 (d, J = 1.6 Hz, 1H), 7.81 (d, J = 7.8 Hz, 1H), 8.26 (d, J = 1.6 Hz, 1H) |
| 114 | 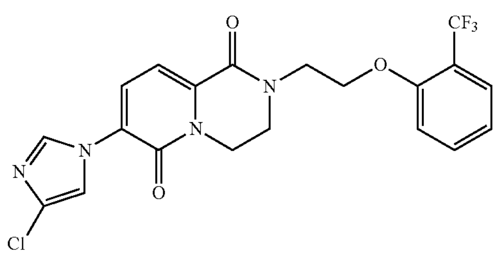 [SMILES: O=C1c2ccc(-n3cnc(Cl)c3)c(=O)n2CCN1CCOc1ccccc1C(F)(F)F] | Ex 1; P11 | 7-(4-chloro-1H-imidazol-1-yl)-2-{2-[2-(trifluoromethyl)phenoxy]ethyl}-3,4-dihydro-2H-pyrido[1,2-a]pyrazine-1,6-dione | 2.89 min[3]; 452.9, 454.9 |
| 115 | 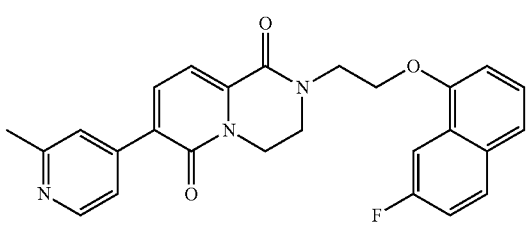 [SMILES: Cc1cc(-c2ccc3n(c2=O)CCN(CCOc2cccc4ccc(F)cc24)C3=O)ccn1] | Ex 1; P10, C41 | 2-{2-[(7-fluoronaphthalen-1-yl)oxy]ethyl}-7-(2-methylpyridin-4-yl)-3,4-dihydro-2H-pyrido[1,2-a]pyrazine-1,6-dione | 2.38 min[3]; 444.0 |
| 116 | 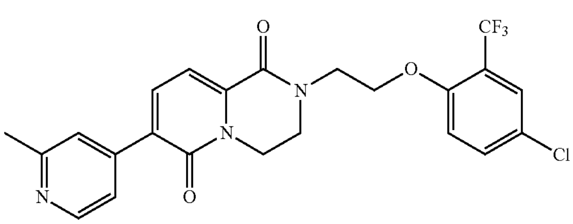 [SMILES: Cc1cc(-c2ccc3n(c2=O)CCN(CCOc2ccc(Cl)cc2C(F)(F)F)C3=O)ccn1] | Ex 1; P10[2] | 2-{2-[4-chloro-2-(trifluoromethyl)phenoxy]ethyl}-7-(2-methylpyridin-4-yl)-3,4-dihydro-2H-pyrido[1,2-a]pyrazine-1,6-dione | 2.61 (br s, 3H), 3.90-3.95 (m, 2H), 3.98-4.03 (m, 2H), 4.29-4.38 (m, 4H), 6.93 (br d, J = 8.8 Hz, 1H), 7.24-7.28 (m, 1H, assumed; partially obscured by solvent peak), 7.43 (br d, J = 5 Hz, 1H), 7.48 (br d, J = 9 Hz, 1H), 7.54-7.59 (m, 2H), 7.68 (d, J = 7.2 Hz, 1H), 8.55 (br d, J = 5 Hz, 1H); 478.1 |

[1](2R)-1-Aminopropan-2-ol was used in place of 2-aminoethanol.
[2]See Example 22 for preparation of the requisite 2-aminoethanol.
[3]HPLC conditions: see footnote 49 in Table 1.

ADDITIONAL EXAMPLES

Additional compounds within the scope of this invention, such as those listed below, may be prepared by one of ordinary skill in the art, using the methods illustrated in these Examples, either alone or in combination with techniques generally known in the art.

2-{2-[4-chloro-2-(trifluoromethyl)phenoxy]ethyl}-7-(1-methyl-1H-pyrazol-4-yl)-3,4-dihydro-2H-pyrido[1,2-a]pyrazine-1,6-dione;

2-{2-[4-chloro-2-(trifluoromethyl)phenoxy]ethyl}-7-(3-methyl-1H-1,2,4-triazol-1-yl)-3,4-dihydro-2H-pyrido[1,2-a]pyrazine-1,6-dione;

7-(3-chloro-1H-1,2,4-triazol-1-yl)-2-{2-[4-chloro-2-(trifluoromethyl)phenoxy]ethyl}-3,4-dihydro-2H-pyrido[1,2-a]pyrazine-1,6-dione;

2-{2-[4-chloro-2-(trifluoromethyl)phenoxy]ethyl}-7-(3-methylisothiazol-5-yl)-3,4-dihydro-2H-pyrido[1,2-a]pyrazine-1,6-dione;

2-{2-[4-chloro-2-(trifluoromethyl)phenoxy]ethyl}-7-(2-methyl-1,3-thiazol-5-yl)-3,4-dihydro-2H-pyrido[1,2-a]pyrazine-1,6-dione;

2-{2-[4-chloro-2-(trifluoromethyl)phenoxy]ethyl}-7-(3-methylisoxazol-5-yl)-3,4-dihydro-2H-pyrido[1,2-a]pyrazine-1,6-dione;

2-(2-{4-fluoro-2-[1-(trifluoromethyl)cyclopropyl]phenoxy}ethyl)-7-(4-methyl-1H-imidazol-1-yl)-3,4-dihydro-2H-pyrido[1,2-a]pyrazine-1,6-dione;

2-[(1S)-2-{4-fluoro-2-[1-(trifluoromethyl)cyclopropyl]phenoxy}-1-methylethyl]-7-(4-methyl-1H-imidazol-1-yl)-3,4-dihydro-2H-pyrido[1,2-a]pyrazine-1,6-dione;

2-{2-[2-(2,2-difluoro-1-methylcyclopropyl)-4-fluorophenoxy]ethyl}-7-(4-methyl-1H-imidazol-1-yl)-3,4-dihydro-2H-pyrido[1,2-a]pyrazine-1,6-dione;

2-{2-[4-fluoro-2-(trimethylsilyl)phenoxy]ethyl}-7-(4-methyl-1H-imidazol-1-yl)-3,4-dihydro-2H-pyrido[1,2-a]pyrazine-1,6-dione;

2-{2-[2-(2,2-difluorocyclopropyl)-4-fluorophenoxy]ethyl}-7-(4-methyl-1H-imidazol-1-yl)-3,4-dihydro-2H-pyrido[1,2-a]pyrazine-1,6-dione;

2-(2-{[7-fluoro-2-(trifluoromethyl)-2,3-dihydro-1-benzofuran-4-yl]oxy}ethyl)-7-(4-methyl-1H-imidazol-1-yl)-3,4-dihydro-2H-pyrido[1,2-a]pyrazine-1,6-dione;

2-(2-{[7-fluoro-3-methyl-3-(trifluoromethyl)-2,3-dihydro-1H-inden-4-yl]oxy}ethyl)-7-(4-methyl-1H-imidazol-1-yl)-3,4-dihydro-2H-pyrido[1,2-a]pyrazine-1,6-dione;

2-(2-{[5-fluoro-8-methyl-8-(trifluoromethyl)bicyclo[4.2.0]octa-1,3,5-trien-2-yl]oxy}ethyl)-7-(4-methyl-1H-imidazol-1-yl)-3,4-dihydro-2H-pyrido[1,2-a]pyrazine-1,6-dione;

2-{(1S)-2-[2-(2,2-difluoro-1-methylcyclopropyl)-4-fluorophenoxy]-1-methylethyl}-7-(4-methyl-1H-imidazol-1-yl)-3,4-dihydro-2H-pyrido[1,2-a]pyrazine-1,6-dione;

2-{(1S)-2-[4-fluoro-2-(trimethylsilyl)phenoxy]-1-methylethyl}-7-(4-methyl-1H-imidazol-1-yl)-3,4-dihydro-2H-pyrido[1,2-a]pyrazine-1,6-dione;

2-{(1S)-2-[2-(2,2-difluorocyclopropyl)-4-fluorophenoxy]-1-methylethyl}-7-(4-methyl-1H-imidazol-1-yl)-3,4-dihydro-2H-pyrido[1,2-a]pyrazine-1,6-dione;

2-[(1S)-2-{[7-fluoro-2-(trifluoromethyl)-2,3-dihydro-1-benzofuran-4-yl]oxy}-1-methylethyl]-7-(4-methyl-1H-imidazol-1-yl)-3,4-dihydro-2H-pyrido[1,2-a]pyrazine-1,6-dione;

2-[(1S)-2-{[7-fluoro-3-methyl-3-(trifluoromethyl)-2,3-dihydro-1H-inden-4-yl]oxy}-1-methylethyl]-7-(4-methyl-1H-imidazol-1-yl)-3,4-dihydro-2H-pyrido[1,2-a]pyrazine-1,6-dione;

2-[(1S)-2-{[5-fluoro-8-methyl-8-(trifluoromethyl)bicyclo[4.2.0]octa-1,3,5-trien-2-yl]oxy}-1-methylethyl]-7-(4-methyl-1H-imidazol-1-yl)-3,4-dihydro-2H-pyrido[1,2-a]pyrazine-1,6-dione;

2-(2-{[7-fluoro-3-methyl-3-(trifluoromethyl)-1,3-dihydro-2-benzofuran-4-yl]oxy}ethyl)-7-(4-methyl-1H-imidazol-1-yl)-3,4-dihydro-2H-pyrido[1,2-a]pyrazine-1,6-dione;

2-[(1S)-2-{[7-fluoro-3-methyl-3-(trifluoromethyl)-1,3-dihydro-2-benzofuran-4-yl]oxy}-1-methylethyl]-7-(4-methyl-1H-imidazol-1-yl)-3,4-dihydro-2H-pyrido[1,2-a]pyrazine-1,6-dione;

2-(2-{[7-fluoro-2-methyl-2-(trifluoromethyl)-2,3-dihydro-1-benzofuran-4-yl]oxy}ethyl)-7-(4-methyl-1H-imidazol-1-yl)-3,4-dihydro-2H-pyrido[1,2-a]pyrazine-1,6-dione;

2-[(1S)-2-{[7-fluoro-2-methyl-2-(trifluoromethyl)-2,3-dihydro-1-benzofuran-4-yl]oxy}-1-methylethyl]-7-(4-methyl-1H-imidazol-1-yl)-3,4-dihydro-2H-pyrido[1,2-a]pyrazine-1,6-dione;

2-(2-{[7-fluoro-3-methyl-3-(trifluoromethyl)-2,3-dihydro-1-benzofuran-4-yl]oxy}ethyl)-7-(4-methyl-1H-imidazol-1-yl)-3,4-dihydro-2H-pyrido[1,2-a]pyrazine-1,6-dione;

2-[(1S)-2-{[7-fluoro-3-methyl-3-(trifluoromethyl)-2,3-dihydro-1-benzofuran-4-yl]oxy}-1-methylethyl]-7-(4-methyl-1H-imidazol-1-yl)-3,4-dihydro-2H-pyrido[1,2-a]pyrazine-1,6-dione;

2-(2-{[7-fluoro-3-(trifluoromethyl)-2,3-dihydro-1-benzofuran-4-yl]oxy}ethyl)-7-(4-methyl-1H-imidazol-1-yl)-3,4-dihydro-2H-pyrido[1,2-a]pyrazine-1,6-dione;

2-[(1S)-2-{[7-fluoro-3-(trifluoromethyl)-2,3-dihydro-1-benzofuran-4-yl]oxy}-1-methylethyl]-7-(4-methyl-1H-imidazol-1-yl)-3,4-dihydro-2H-pyrido[1,2-a]pyrazine-1,6-dione;

2-[2-(2-bicyclo[1.1.1]pent-1-yl-4-chlorophenoxy)ethyl]-7-(4-methyl-1H-imidazol-1-yl)-3,4-dihydro-2H-pyrido[1,2-a]pyrazine-1,6-dione;

2-[2-(2-bicyclo[1.1.1]pent-1-yl-4-fluorophenoxy)ethyl]-7-(4-methyl-1H-imidazol-1-yl)-3,4-dihydro-2H-pyrido[1,2-a]pyrazine-1,6-dione;

2-[(1S)-2-(2-bicyclo[1.1.1]pent-1-yl-4-chlorophenoxy)-1-methylethyl]-7-(4-methyl-1H-imidazol-1-yl)-3,4-dihydro-2H-pyrido[1,2-a]pyrazine-1,6-dione;

2-[(1S)-2-(2-bicyclo[1.1.1]pent-1-yl-4-fluorophenoxy)-1-methylethyl]-7-(4-methyl-1H-imidazol-1-yl)-3,4-dihydro-2H-pyrido[1,2-a]pyrazine-1,6-dione;

2-{2-[4-chloro-2-(3-fluorobicyclo[1.1.1]pent-1-yl)phenoxy]ethyl}-7-(4-methyl-1H-imidazol-1-yl)-3,4-dihydro-2H-pyrido[1,2-a]pyrazine-1,6-dione;

2-{2-[4-fluoro-2-(3-fluorobicyclo[1.1.1]pent-1-yl)phenoxy]ethyl}-7-(4-methyl-1H-imidazol-1-yl)-3,4-dihydro-2H-pyrido[1,2-a]pyrazine-1,6-dione;

2-{(1S)-2-[4-chloro-2-(3-fluorobicyclo[1.1.1]pent-1-yl)phenoxy]-1-methylethyl}-7-(4-methyl-1H-imidazol-1-yl)-3,4-dihydro-2H-pyrido[1,2-a]pyrazine-1,6-dione;

2-{(1S)-2-[4-fluoro-2-(3-fluorobicyclo[1.1.1]pent-1-yl)phenoxy]-1-methylethyl}-7-(4-methyl-1H-imidazol-1-yl)-3,4-dihydro-2H-pyrido[1,2-a]pyrazine-1,6-dione;

2-(2-{4-fluoro-2-[3-(trifluoromethyl)bicyclo[1.1.1]pent-1-yl]phenoxy}ethyl)-7-(4-methyl-1H-imidazol-1-yl)-3,4-dihydro-2H-pyrido[1,2-a]pyrazine-1,6-dione;

2-[(1S)-2-{4-fluoro-2-[3-(trifluoromethyl)bicyclo[1.1.1]pent-1-yl]phenoxy}-1-methylethyl]-7-(4-methyl-1H-imidazol-1-yl)-3,4-dihydro-2H-pyrido[1,2-a]pyrazine-1,6-dione;

7-(4-methyl-1H-imidazol-1-yl)-2-{2-[(2,2,7-trifluoro-2,3-dihydro-1H-inden-4-yl)oxy]ethyl}-3,4-dihydro-2H-pyrido[1,2-a]pyrazine-1,6-dione;

7-(4-methyl-1H-imidazol-1-yl)-2-{2-[(2,2,7-trifluoro-2,3-dihydro-1-benzofuran-4-yl)oxy]ethyl}-3,4-dihydro-2H-pyrido[1,2-a]pyrazine-1,6-dione;

2-{2-[(2,2-difluoro-2,3-dihydro-1-benzofuran-4-yl)oxy]ethyl}-7-(4-methyl-1H-imidazol-1-yl)-3,4-dihydro-2H-pyrido[1,2-a]pyrazine-1,6-dione;

7-(4-methyl-1H-imidazol-1-yl)-2-{2-[(2,2,3,3,7-pentafluoro-2,3-dihydro-1-benzofuran-4-yl)oxy]ethyl}-3,4-dihydro-2H-pyrido[1,2-a]pyrazine-1,6-dione;

7-(4-methyl-1H-imidazol-1-yl)-2-{2-[(2,2,3,3-tetrafluoro-2,3-dihydro-1-benzofuran-4-yl)oxy]ethyl}-3,4-dihydro-2H-pyrido[1,2-a]pyrazine-1,6-dione;

2-{2-[4-fluoro-2-(2,2,2-trifluoro-1-hydroxy-1-methylethyl)phenoxy]ethyl}-7-(4-methyl-1H-imidazol-1-yl)-3,4-dihydro-2H-pyrido[1,2-a]pyrazine-1,6-dione;

2-{2-[4-fluoro-2-(2,2,2-trifluoro-1-methylethyl)phenoxy]ethyl}-7-(4-methyl-1H-imidazol-1-yl)-3,4-dihydro-2H-pyrido[1,2-a]pyrazine-1,6-dione;

2-{2-[(7-chloro-2,2-difluoro-2,3-dihydro-1H-inden-4-yl)oxy]ethyl}-7-(4-methyl-1H-imidazol-1-yl)-3,4-dihydro-2H-pyrido[1,2-a]pyrazine-1,6-dione;

7-(4-methyl-1H-imidazol-1-yl)-2-{2-[(2,2,8-trifluoro-3,4-dihydro-2H-chromen-5-yl)oxy]ethyl}-3,4-dihydro-2H-pyrido[1,2-a]pyrazine-1,6-dione;

7-(4-methyl-1H-imidazol-1-yl)-2-{2-[(2,2,8-trifluoro-2H-chromen-5-yl)oxy]ethyl}-3,4-dihydro-2H-pyrido[1,2-a]pyrazine-1,6-dione;

7-(4-methyl-1H-imidazol-1-yl)-2-{2-[(2,2,5-trifluoro-3,4-dihydro-2H-chromen-8-yl)oxy]ethyl}-3,4-dihydro-2H-pyrido[1,2-a]pyrazine-1,6-dione;

7-(4-methyl-1H-imidazol-1-yl)-2-{2-[(2,2,5-trifluoro-2H-chromen-8-yl)oxy]ethyl}-3,4-dihydro-2H-pyrido[1,2-a]pyrazine-1,6-dione;

7-(4-methyl-1H-imidazol-1-yl)-2-{2-[(4,4,8-trifluoro-3,4-dihydro-2H-chromen-5-yl)oxy]ethyl}-3,4-dihydro-2H-pyrido[1,2-a]pyrazine-1,6-dione;

7-(4-methyl-1H-imidazol-1-yl)-2-{2-[(3,3,8-trifluoro-3,4-dihydro-2H-chromen-5-yl)oxy]ethyl}-3,4-dihydro-2H-pyrido[1,2-a]pyrazine-1,6-dione;

7-(4-methyl-1H-imidazol-1-yl)-2-{(1S)-1-methyl-2-[(2,2,7-trifluoro-2,3-dihydro-1H-inden-4-yl)oxy]ethyl}-3,4-dihydro-2H-pyrido[1,2-a]pyrazine-1,6-dione;

7-(4-methyl-1H-imidazol-1-yl)-2-{(1S)-1-methyl-2-[(2,2,7-trifluoro-2,3-dihydro-1-benzofuran-4-yl)oxy]ethyl}-3,4-dihydro-2H-pyrido[1,2-a]pyrazine-1,6-dione;

2-{(1S)-2-[(2,2-difluoro-2,3-dihydro-1-benzofuran-4-yl)oxy]-1-methylethyl}-7-(4-methyl-1H-imidazol-1-yl)-3,4-dihydro-2H-pyrido[1,2-a]pyrazine-1,6-dione;

7-(4-methyl-1H-imidazol-1-yl)-2-{(1S)-1-methyl-2-[(2,2,3,3,7-pentafluoro-2,3-dihydro-1-benzofuran-4-yl)oxy]ethyl}-3,4-dihydro-2H-pyrido[1,2-a]pyrazine-1,6-dione;

7-(4-methyl-1H-imidazol-1-yl)-2-{(1S)-1-methyl-2-[(2,2,3,3-tetrafluoro-2,3-dihydro-1-benzofuran-4-yl)oxy]ethyl}-3,4-dihydro-2H-pyrido[1,2-a]pyrazine-1,6-dione;

2-{(1S)-2-[4-fluoro-2-(2,2,2-trifluoro-1-hydroxy-1-methylethyl)phenoxy]-1-methylethyl}-7-(4-methyl-1H-imidazol-1-yl)-3,4-dihydro-2H-pyrido[1,2-a]pyrazine-1,6-dione;

2-{(1S)-2-[4-fluoro-2-(2,2,2-trifluoro-1-methylethyl)phenoxy]-1-methylethyl}-7-(4-methyl-1H-imidazol-1-yl)-3,4-dihydro-2H-pyrido[1,2-a]pyrazine-1,6-dione;

2-{(1S)-2-[(7-chloro-2,2-difluoro-2,3-dihydro-1H-inden-4-yl)oxy]-1-methylethyl}-7-(4-methyl-1H-imidazol-1-yl)-3,4-dihydro-2H-pyrido[1,2-a]pyrazine-1,6-dione;

7-(4-methyl-1H-imidazol-1-yl)-2-{(1S)-1-methyl-2-[(2,2,8-trifluoro-3,4-dihydro-2H-chromen-5-yl)oxy]ethyl}-3,4-dihydro-2H-pyrido[1,2-a]pyrazine-1,6-dione;

7-(4-methyl-1H-imidazol-1-yl)-2-{(1S)-1-methyl-2-[(2,2,8-trifluoro-2H-chromen-5-yl)oxy]ethyl}-3,4-dihydro-2H-pyrido[1,2-a]pyrazine-1,6-dione;

7-(4-methyl-1H-imidazol-1-yl)-2-{(1S)-1-methyl-2-[(2,2,5-trifluoro-3,4-dihydro-2H-chromen-8-yl)oxy]ethyl}-3,4-dihydro-2H-pyrido[1,2-a]pyrazine-1,6-dione;

7-(4-methyl-1H-imidazol-1-yl)-2-{(1S)-1-methyl-2-[(2,2,5-trifluoro-2H-chromen-8-yl)oxy]ethyl}-3,4-dihydro-2H-pyrido[1,2-a]pyrazine-1,6-dione;

7-(4-methyl-1H-imidazol-1-yl)-2-{(1S)-1-methyl-2-[(4,4,8-trifluoro-3,4-dihydro-2H-chromen-5-yl)oxy]ethyl}-3,4-dihydro-2H-pyrido[1,2-a]pyrazine-1,6-dione;

7-(4-methyl-1H-imidazol-1-yl)-2-{(1S)-1-methyl-2-[(3,3,8-trifluoro-3,4-dihydro-2H-chromen-5-yl)oxy]ethyl}-3,4-dihydro-2H-pyrido[1,2-a]pyrazine-1,6-dione;

7-(4-methyl-1H-imidazol-1-yl)-2-{2-[(3,3,7-trifluoro-2,3-dihydro-1H-inden-4-yl)oxy]ethyl}-3,4-dihydro-2H-pyrido[1,2-a]pyrazine-1,6-dione;

2-{2-[(3,3-difluoro-2,3-dihydro-1H-inden-4-yl)oxy]ethyl}-7-(4-methyl-1H-imidazol-1-yl)-3,4-dihydro-2H-pyrido[1,2-a]pyrazine-1,6-dione;

7-(4-methyl-1H-imidazol-1-yl)-2-{2-[(2,2,3,3,7-pentafluoro-2,3-dihydro-1H-inden-4-yl)oxy]ethyl}-3,4-dihydro-2H-pyrido[1,2-a]pyrazine-1,6-dione;

7-(4-methyl-1H-imidazol-1-yl)-2-{2-[(2,2,3,3-tetrafluoro-2,3-dihydro-1H-inden-4-yl)oxy]ethyl}-3,4-dihydro-2H-pyrido[1,2-a]pyrazine-1,6-dione;

2-{2-[(2,2-difluoro-3,4-dihydro-2H-chromen-5-yl)oxy]ethyl}-7-(4-methyl-1H-imidazol-1-yl)-3,4-dihydro-2H-pyrido[1,2-a]pyrazine-1,6-dione;

2-{2-[(2,2-difluoro-2H-chromen-5-yl)oxy]ethyl}-7-(4-methyl-1H-imidazol-1-yl)-3,4-dihydro-2H-pyrido[1,2-a]pyrazine-1,6-dione;

2-{2-[(2,2-difluoro-3,4-dihydro-2H-chromen-8-yl)oxy]ethyl}-7-(4-methyl-1H-imidazol-1-yl)-3,4-dihydro-2H-pyrido[1,2-a]pyrazine-1,6-dione;

2-{2-[(2,2-difluoro-2H-chromen-8-yl)oxy]ethyl}-7-(4-methyl-1H-imidazol-1-yl)-3,4-dihydro-2H-pyrido[1,2-a]pyrazine-1,6-dione;

2-{2-[(4,4-difluoro-3,4-dihydro-2H-chromen-5-yl)oxy]ethyl}-7-(4-methyl-1H-imidazol-1-yl)-3,4-dihydro-2H-pyrido[1,2-a]pyrazine-1,6-dione;

2-{2-[(3,3-difluoro-3,4-dihydro-2H-chromen-5-yl)oxy]ethyl}-7-(4-methyl-1H-imidazol-1-yl)-3,4-dihydro-2H-pyrido[1,2-a]pyrazine-1,6-dione;

2-{2-[(4,4-difluoro-4H-chromen-5-yl)oxy]ethyl}-7-(4-methyl-1H-imidazol-1-yl)-3,4-dihydro-2H-pyrido[1,2-a]pyrazine-1,6-dione;

2-{2-[(8,8-difluoro-5,6,7,8-tetrahydronaphthalen-1-yl)oxy]ethyl}-7-(4-methyl-1H-imidazol-1-yl)-3,4-dihydro-2H-pyrido[1,2-a]pyrazine-1,6-dione;

7-(4-methyl-1H-imidazol-1-yl)-2-{2-[(4,8,8-trifluoro-5,6,7,8-tetrahydronaphthalen-1-yl)oxy]ethyl}-3,4-dihydro-2H-pyrido[1,2-a]pyrazine-1,6-dione;

2-{2-[(7,7-difluoro-5,6,7,8-tetrahydronaphthalen-1-yl)oxy]ethyl}-7-(4-methyl-1H-imidazol-1-yl)-3,4-dihydro-2H-pyrido[1,2-a]pyrazine-1,6-dione;

7-(4-methyl-1H-imidazol-1-yl)-2-{(1S)-1-methyl-2-[(3,3,7-trifluoro-2,3-dihydro-1H-inden-4-yl)oxy]ethyl}-3,4-dihydro-2H-pyrido[1,2-a]pyrazine-1,6-dione;

2-{(1S)-2-[(3,3-difluoro-2,3-dihydro-1H-inden-4-yl)oxy]-1-methylethyl}-7-(4-methyl-1H-imidazol-1-yl)-3,4-dihydro-2H-pyrido[1,2-a]pyrazine-1,6-dione;

7-(4-methyl-1H-imidazol-1-yl)-2-{(1S)-1-methyl-2-[(2,2,3,3,7-pentafluoro-2,3-dihydro-1H-inden-4-yl)oxy]ethyl}-3,4-dihydro-2H-pyrido[1,2-a]pyrazine-1,6-dione;

7-(4-methyl-1H-imidazol-1-yl)-2-{(1S)-1-methyl-2-[(2,2,3,3-tetrafluoro-2,3-dihydro-1H-inden-4-yl)oxy]ethyl}-3,4-dihydro-2H-pyrido[1,2-a]pyrazine-1,6-dione;

2-{(1S)-2-[(2,2-difluoro-3,4-dihydro-2H-chromen-5-yl)oxy]-1-methylethyl}-7-(4-methyl-1H-imidazol-1-yl)-3,4-dihydro-2H-pyrido[1,2-a]pyrazine-1,6-dione;

2-{(1S)-2-[(2,2-difluoro-2H-chromen-5-yl)oxy]-1-methylethyl}-7-(4-methyl-1H-imidazol-1-yl)-3,4-dihydro-2H-pyrido[1,2-a]pyrazine-1,6-dione;

2-{(1S)-2-[(2,2-difluoro-3,4-dihydro-2H-chromen-8-yl)oxy]-1-methylethyl}-7-(4-methyl-1H-imidazol-1-yl)-3,4-dihydro-2H-pyrido[1,2-a]pyrazine-1,6-dione;

2-{(1S)-2-[(2,2-difluoro-2H-chromen-8-yl)oxy]-1-methylethyl}-7-(4-methyl-1H-imidazol-1-yl)-3,4-dihydro-2H-pyrido[1,2-a]pyrazine-1,6-dione;

2-{(1S)-2-[(4,4-difluoro-3,4-dihydro-2H-chromen-5-yl)oxy]-1-methylethyl}-7-(4-methyl-1H-imidazol-1-yl)-3,4-dihydro-2H-pyrido[1,2-a]pyrazine-1,6-dione;

2-{(1S)-2-[(3,3-difluoro-3,4-dihydro-2H-chromen-5-yl)oxy]-1-methylethyl}-7-(4-methyl-1H-imidazol-1-yl)-3,4-dihydro-2H-pyrido[1,2-a]pyrazine-1,6-dione;

2-{(1S)-2-[(4,4-difluoro-4H-chromen-5-yl)oxy]-1-methylethyl}-7-(4-methyl-1H-imidazol-1-yl)-3,4-dihydro-2H-pyrido[1,2-a]pyrazine-1,6-dione;

2-{(1S)-2-[(8,8-difluoro-5,6,7,8-tetrahydronaphthalen-1-yl)oxy]-1-methylethyl}-7-(4-methyl-1H-imidazol-1-yl)-3,4-dihydro-2H-pyrido[1,2-a]pyrazine-1,6-dione;

7-(4-methyl-1H-imidazol-1-yl)-2-{(1S)-1-methyl-2-[(4,8,8-trifluoro-5,6,7,8-tetrahydronaphthalen-1-yl)oxy]ethyl}-3,4-dihydro-2H-pyrido[1,2-a]pyrazine-1,6-dione;

2-{(1S)-2-[(7,7-difluoro-5,6,7,8-tetrahydronaphthalen-1-yl)oxy]-1-methylethyl}-7-(4-methyl-1H-imidazol-1-yl)-3,4-dihydro-2H-pyrido[1,2-a]pyrazine-1,6-dione;

7-(4-methyl-1H-imidazol-1-yl)-2-{(1S)-1-methyl-2-[(2,2,4-trifluoro-2,3-dihydro-1-benzofuran-7-yl)oxy]ethyl}-3,4-dihydro-2H-pyrido[1,2-a]pyrazine-1,6-dione;

2-{(1S)-2-[(2,2-difluoro-2,3-dihydro-1-benzofuran-7-yl)oxy]-1-methylethyl}-7-(4-methyl-1H-imidazol-1-yl)-3,4-dihydro-2H-pyrido[1,2-a]pyrazine-1,6-dione;

7-(4-methyl-1H-imidazol-1-yl)-2-{2-[(2,2,4-trifluoro-2,3-dihydro-1-benzofuran-7-yl)oxy]ethyl}-3,4-dihydro-2H-pyrido[1,2-a]pyrazine-1,6-dione;

2-{2-[(2,2-difluoro-2,3-dihydro-1-benzofuran-7-yl)oxy]ethyl}-7-(4-methyl-1H-imidazol-1-yl)-3,4-dihydro-2H-pyrido[1,2-a]pyrazine-1,6-dione;

pentafluoro(5-fluoro-2-{2-[7-(4-methyl-1H-imidazol-1-yl)-1,6-dioxo-1,3,4,6-tetrahydro-2H-pyrido[1,2-a]pyrazin-2-yl]ethoxy}phenyl)sulfur;

pentafluoro[5-fluoro-2-({(2S)-2-[7-(4-methyl-1H-imidazol-1-yl)-1,6-dioxo-1,3,4,6-tetrahydro-2H-pyrido[1,2-a]pyrazin-2-yl]propyl}oxy)phenyl]sulfur;

pentafluoro(2-{2-[7-(4-methyl-1H-imidazol-1-yl)-1,6-dioxo-1,3,4,6-tetrahydro-2H-pyrido[1,2-a]pyrazin-2-yl]ethoxy}phenyl)sulfur; and pentafluoro[2-({(2S)-2-[7-(4-methyl-1H-imidazol-1-yl)-1,6-dioxo-1,3,4,6-tetrahydro-2H-pyrido[1,2-a]pyrazin-2-yl]propyl}oxy)phenyl]sulfur.

Cell-Based γ-Secretase Assay with ELISA Readout

The ability of compounds to modulate production of amyloid beta protein Aβ(1-42) was determined using human WT-APP overexpressing CHO cells. Cells were plated at 22,000 cells/100 μL well in 96 well tissue culture treated, clear plates (Falcon) in DMEM/F12 based medium and incubated for 24 hours at 37° C. Compounds for testing were diluted in 100% DMSO to achieve an eleven points, half log, dose response for IC$_{50}$ determinations. Compounds were added in fresh medium to achieve 1% final DMSO. Appropriate vehicle or inhibitor controls were added into control wells individually to obtain minimum or maximum inhibition values, respectively, for the assay signal window before the plates were incubated for ~24 hours at 37° C. This procedure produces conditioned media in each well which is tested for Aβ(1-42) levels in the ELISA detection step described next. The remaining cell cultures in each well are also tested for cell toxicity as described below.

Coating of ELISA assay plates was initiated by addition of 50 μL/well of an in-house Aβ(1-42) specific antibody at (3 μg/mL) in 0.1 M NaHCO$_3$ (pH 9.0) into black 384-well Maxisorp® plates (Nunc) and incubated overnight at 4° C. The capture antibody was then aspirated from the ELISA assay plates and plates were washed 4×100 μL with Wash Buffer (Dulbecco's PBS, 0.05% Tween 20). 90 μL/well of Blocking Buffer (Dulbecco's PBS, 1.0% BSA (Sigma A7030)) was then added to plates. Ambient temperature incubation was allowed to proceed for a minimum of two hours. Blocking buffer was then removed and 20 μL/well Assay Buffer (Dulbecco's PBS, 1.0% BSA (Sigma A7030), 0.05% Tween 20) was then added. At this point, 40 μL (in duplicate) of experimental conditioned media (described above) were transferred into wells of the blocked ELISA plates containing the capture antibody, followed by overnight incubation at 4° C. Cell toxicity was also measured in the corresponding remaining cells after removal of the conditioned media for the Aβ(1-42) assay by a colorimetric cell proliferation assay (CellTiter 96®AQ$_{ueous}$ One Solution Cell Proliferation Assay, Promega) according to the manufacturer's instructions.

After overnight incubation of the ELISA assay plates at 4° C., unbound Aβ peptides were removed via (4×100 μL) washes with Wash Buffer. Europium (Eu) labeled (custom labeled, Perkin Elmer) Aβ(1-16) 6e10 Monoclonal Antibody (Covance #SIG-39320) was added, (50 μL/well Eu-6e10 @ 1:10,000, 20 uM EDTA) in Assay Buffer. Incubation at ambient temperature for a minimum of 2 hours was followed by (4×100 μL) washes with Wash Buffer, before 30 μL/well of Delfia Enhancement Solution (Perkin Elmer) was added. Following an one hour ambient temperature incubation, the plates were read on an EnVision plate reader (Perkin Elmer) using standard DELFIA TRF settings. Data analysis including inhibitory IC$_{50}$ determination was performed using non-linear regression fit analysis (in-house software) and the appropriate plate mean values for the maximum and minimum inhibition

TABLE 3

| Example number | Aβ 42B IC$_{50}$ (nM) (Geometric Mean of 2-6 Determinations) |
|---|---|
| 1 | 256[a] |
| 2 | 434 |
| 3 | 86 |
| 4 | 146 |
| 5 | 996 |
| 6 | 36.5 |
| 7 | 42[b] |
| 8 | 93 |
| 9 | 83.9 |
| 10 | 127 |
| 11 | 536 |
| 12 | 196 |
| 13 | 108 |
| 14 | 197[b] |
| 15 | 275 |
| 16 | 234 |

TABLE 3-continued

| Example number | Aβ 42B IC$_{50}$ (nM) (Geometric Mean of 2-6 Determinations) |
|---|---|
| 17 | 153 |
| 18 | 151[b] |
| 19 | 203 |
| 20 | 157 |
| 21 | 262 |
| 22 | 103[a] |
| 23 | 173 |
| 24 | 104[b] |
| 25 | 73.2 |
| 26 | 95.7 |
| 27 | 103 |
| 28 | 31.9 |
| 29 | 154[b] |
| 30 | 132 |
| 31 | 96.8[b] |
| 32 | 143 |
| 33 | 194 |
| 34 | 262 |
| 35 | 133 |
| 36 | 302 |
| 37 | 219 |
| 38 | 293 |
| 39 | 525 |
| 40 | 19.6 |
| 41 | 156 |
| 42 | 5.31 |
| 43 | 283 |
| 44 | 142 |
| 45 | 66.3 |
| 46 | 9.38 |
| 47 | 9.48 |
| 48 | 143 |
| 49 | 178 |
| 50 | 29.3 |
| 51 | 20 |
| 52 | 23.5 |
| 53 | 26.2 |
| 54 | 215 |
| 55 | 168 |
| 56 | 399 |
| 57 | 113 |
| 58 | 72.1 |
| 59 | 530[b] |
| 60 | 33.3 |
| 61 | 108 |
| 62 | 39.7 |
| 63 | 76.6[b] |
| 64 | 42.4 |
| 65 | 46.1 |
| 66 | 52.4[b] |
| 67 | 58.4 |
| 68 | 59.4 |
| 69 | 58.3 |
| 70 | 135 |
| 71 | 4.22 |
| 72 | 14.8 |
| 73 | 43.7 |
| 74 | 38.5 |
| 75 | 62.3[b] |
| 76 | 58.6 |
| 77 | 66.2 |
| 78 | 87.5[b] |
| 79 | 7.23 |
| 80 | 152 |
| 81 | 384 |
| 82 | 209 |
| 83 | 12.3 |
| 84 | 71.5 |
| 85 | 106 |
| 86 | 107 |
| 87 | 22.8 |
| 88 | 75.4 |
| 89 | 101 |
| 90 | 147 |
| 91 | 120 |
| 92 | 4.87 |
| 93 | 75.8[b] |
| 94 | 108 |
| 95 | 143 |
| 96 | 48.2 |
| 97 | 21.3 |
| 98 | 19.4 |
| 99 | 25.3 |
| 100 | 135 |
| 101 | 456 |
| 102 | 33.7 |
| 103 | 596[b] |
| 104 | 7.2 |
| 105 | 25.2[b] |
| 106 | 27.4 |
| 107 | 34.4 |
| 108 | 46.8 |
| 109 | 275 |
| 110 | 14.5 |
| 111 | 138 |
| 112 | 340 |
| 113 | 292 |
| 114 | 1320[b] |
| 115 | 489 |
| 116 | 3490[b] |
| 117 | 3.54 |
| 118 | <6.64[c] |
| 119 | 7.49 |
| 120 | 17.8 |
| 121 | 30.2 |
| 122 | 85.6 |
| 123 | 106 |
| 124 | 2310[b] |
| 125 | 653 |
| 126 | 20.1 |
| 127 | 1070[b] |

[a]IC$_{50}$ value represents the geometric mean of >15 determinations.
[b]IC$_{50}$ value is from a single determination.
[c]IC$_{50}$ value represents the geometric mean of 7-15 determinations.

We claim:
1. A compound having the structure of Formula I:

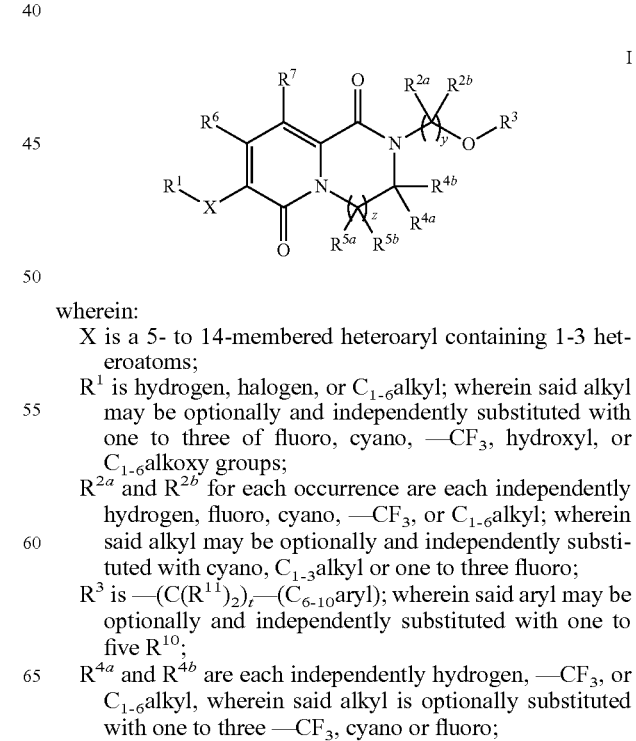

wherein:
X is a 5- to 14-membered heteroaryl containing 1-3 heteroatoms;
$R^1$ is hydrogen, halogen, or $C_{1-6}$alkyl; wherein said alkyl may be optionally and independently substituted with one to three of fluoro, cyano, —$CF_3$, hydroxyl, or $C_{1-6}$alkoxy groups;
$R^{2a}$ and $R^{2b}$ for each occurrence are each independently hydrogen, fluoro, cyano, —$CF_3$, or $C_{1-6}$alkyl; wherein said alkyl may be optionally and independently substituted with cyano, $C_{1-3}$alkyl or one to three fluoro;
$R^3$ is —$(C(R^{11})_2)_t$—$(C_{6-10}aryl)$; wherein said aryl may be optionally and independently substituted with one to five $R^{10}$;
$R^{4a}$ and $R^{4b}$ are each independently hydrogen, —$CF_3$, or $C_{1-6}$alkyl, wherein said alkyl is optionally substituted with one to three —$CF_3$, cyano or fluoro;

$R^{5a}$ and $R^{5b}$ for each occurrence are each independently hydrogen, —$CF_3$, or $C_{1-6}$alkyl, wherein said alkyl is optionally substituted with one to three —$CF_3$, cyano or fluoro;

$R^6$ and $R^7$ are each independently hydrogen, —$CF_3$, cyano, halogen, $C_{1-6}$alkyl or —$OR^9$; provided that $R^6$ and $R^7$ cannot both be —OH;

$R^9$ is hydrogen, or $C_{1-6}$alkyl, wherein said alkyl may be optionally and independently substituted with cyano, or one to three fluoro;

each $R^{10}$ is independently hydrogen, halogen, cyano, —$CF_3$, $C_{1-6}$alkyl, —$(C(R^{11})_2)_m$—$OR^{12}$, —$C(O)R^{13}$, —$SF_5$ or —$Si(CH_3)_3$; wherein said alkyl, may be optionally and independently substituted with one to three $R^{14}$;

each $R^{11}$ is independently hydrogen, $C_{1-6}$alkyl, fluoro, —$CF_3$, —$CHF_2$ or —$OR^{12}$; wherein said alkyl may be optionally independently substituted with one to three fluoro or cyano;

each $R^{12}$ is independently hydrogen, $C_{1-6}$alkyl, or —$CF_3$; wherein said alkyl may be optionally independently substituted with one to three $R^{16}$;

each $R^{13}$ is independently $C_{1-6}$alkyl; wherein said alkyl may be optionally and independently substituted with one to three $R^{16}$;

each $R^{14}$ is independently hydrogen, $C_{1-6}$alkyl, halogen, cyano, —$CF_3$, —$CHF_2$, —$OR^9$ or —$OCF_3$;

$R^{16}$ is independently hydrogen, —$CF_3$, cyano, halogen, $C_{1-6}$alkyl or —$OR^9$ and t and m are each an integer independently selected from 0, 1, 2, 3 and 4;

z is the integer 1;

y is an integer selected from 1, 2, 3 and 4;

or a pharmaceutically acceptable salts thereof.

2. The compound according to claim 1 wherein X is imidazolyl, pyrazolyl, isothiazolyl, thiazolyl, isoxazolyl, oxazolyl or pyridyl.

3. The compound according to claim 2 wherein X is imidazolyl.

4. The compound according to claim 3 wherein $R^1$ is $C_{1-6}$alkyl.

5. The compound according to claim 4 wherein $R^1$ is methyl optionally substituted with one hydroxyl or $C_{1-6}$alkoxy or one to three fluoro; and y is two or three.

6. The compound according to claim 5 wherein $R^{10}$ is independently hydrogen, halogen, cyano, —$CF_3$, $C_{1-6}$alkyl, —$(C(R^{11})_2)_m$—$OR^{12}$ or —$C(O)R^{13}$; wherein the alkyl may be independently substituted with one to three $R^{14}$.

7. The compound according to claim 5 wherein $R^3$ is phenyl.

8. The compound according to claim 7 wherein $R^{10}$ is hydrogen, chloro, fluoro, bromo, cyano, —$CF_3$, —$OCF_3$, methyl, ethyl, propyl, isopropyl, butyl, tert-butyl, hydroxyl, or methoxy.

9. The compound according to claim 8 wherein $R^{2a}$ and $R^{2b}$ are hydrogen or $C_{1-6}$alkyl.

10. A compound selected from the group consisting of:
- 2-{(1S)-2-[4-fluoro-2-(trifluoromethyl)phenoxy]-1-methylethyl}-7-(4-methyl-1H-imidazol-1-yl)-3,4-dihydro-2H-pyrido[1,2-a]pyrazine-1,6-dione;
- 2-{2-[4-fluoro-2-(1,1,1-trifluoro-2-methylpropan-2-yl)phenoxy]ethyl}-7-(4-methyl-1H-imidazol-1-yl)-3,4-dihydro-2H-pyrido[1,2-a]pyrazine-1,6-dione;
- 2-{(2S)-1-[4-chloro-2-(trifluoromethyl)phenoxy]propan-2-yl}-7-(4-methyl-1H-imidazol-1-yl)-3,4-dihydro-2H-pyrido[1,2-a]pyrazine-1,6-dione; or a pharmaceutically acceptable salt of any of the above.

11. A method for treating a mammal having Alzheimer's Disease comprising administering to the mammal a therapeutically effective amount of the compound of claim 1 or a pharmaceutically acceptable salt thereof.

12. A pharmaceutical composition comprising a compound of claim 1, or a pharmaceutically acceptable salt thereof, and a pharmaceutically acceptable vehicle, diluent or carrier.

* * * * *